(12) United States Patent
Savarese

(10) Patent No.: US 8,592,451 B2
(45) Date of Patent: Nov. 26, 2013

(54) REVERSIBLE NONDEPOLARIZING NEUROMUSCULAR BLOCKADE AGENTS AND METHODS FOR THEIR USE

(75) Inventor: John J. Savarese, Southbury, CT (US)

(73) Assignee: Cornell University, Ithaca, NY (US)

(*) Notice: Subject to any disclaimer, the term of this patent is extended or adjusted under 35 U.S.C. 154(b) by 13 days.

(21) Appl. No.: 13/257,214

(22) PCT Filed: Mar. 17, 2010

(86) PCT No.: PCT/US2010/000796
§ 371 (c)(1),
(2), (4) Date: Dec. 13, 2011

(87) PCT Pub. No.: WO2010/107488
PCT Pub. Date: Sep. 23, 2010

(65) Prior Publication Data
US 2012/0095041 A1    Apr. 19, 2012

Related U.S. Application Data

(60) Provisional application No. 61/160,915, filed on Mar. 17, 2009.

(51) Int. Cl.
*A61K 31/472* (2006.01)
*C07D 217/12* (2006.01)
*C07D 217/20* (2006.01)

(52) U.S. Cl.
USPC ............ 514/308; 546/140; 546/144; 546/147; 546/149

(58) Field of Classification Search
USPC .................. 514/308; 546/140, 144, 147, 149
See application file for complete search history.

(56) References Cited

U.S. PATENT DOCUMENTS

| | | | |
|---|---|---|---|
| 3,004,031 A | 10/1961 | Taylor et al. |
| 4,036,959 A | 7/1977 | Green et al. |
| 4,039,682 A | 8/1977 | Ausman et al. |
| 4,179,507 A | 12/1979 | Stenlake et al. |
| 4,192,877 A | 3/1980 | Savarese et al. |
| 4,235,906 A | 11/1980 | Savarese et al. |
| 4,491,665 A | 1/1985 | El-Sayad et al. |
| 4,556,712 A | 12/1985 | Rice |
| 4,666,918 A | 5/1987 | Ivanova et al. |
| 4,686,228 A | 8/1987 | Campbell et al. |
| 4,701,460 A | 10/1987 | El-Sayad et al. |
| 4,707,485 A | 11/1987 | Kaiser et al. |
| 4,727,146 A | 2/1988 | Rice |
| 4,727,147 A | 2/1988 | Wintermeyer et al. |
| 4,761,418 A | 8/1988 | Swaringen, Jr. et al. |
| 5,240,939 A | 8/1993 | Demko |
| 5,438,140 A | 8/1995 | Oftring et al. |
| 5,453,510 A | 9/1995 | Hill et al. |
| 5,556,978 A | 9/1996 | Hill et al. |
| 5,684,154 A | 11/1997 | Chamberlin et al. |
| 6,177,445 B1 | 1/2001 | Bigham et al. |
| 6,187,789 B1 | 2/2001 | Bigham et al. |
| 6,194,421 B1 | 2/2001 | Cohen et al. |
| 6,548,521 B1 | 4/2003 | Cohen et al. |
| 6,562,836 B1 | 5/2003 | Szarek et al. |
| 6,858,750 B2 | 2/2005 | Joshi |
| 7,037,489 B2 | 5/2006 | Uchiwa et al. |
| 8,148,398 B2 | 4/2012 | Savarese |
| 2003/0149082 A1 | 8/2003 | Makriyannis et al. |
| 2003/0191115 A1 | 10/2003 | Pinto et al. |
| 2004/0054001 A1 | 3/2004 | Joshi et al. |
| 2004/0180925 A1 | 9/2004 | Matsuno et al. |
| 2005/0192243 A1 | 9/2005 | Savarese |
| 2006/0177408 A1 | 8/2006 | Uchiwa et al. |
| 2006/0205659 A1 | 9/2006 | Joshi et al. |
| 2008/0139482 A1 | 6/2008 | Savarese |
| 2012/0214873 A1 | 8/2012 | Savarese et al. |

FOREIGN PATENT DOCUMENTS

| | | |
|---|---|---|
| CN | 101366695 A | 2/2009 |
| EP | 0008824 A1 | 3/1980 |
| EP | 1380573 A2 | 1/2004 |
| EP | 1526130 A1 | 4/2005 |
| EP | 1676580 A1 | 7/2006 |
| JP | 54-055577 A | 5/1979 |
| JP | 61-087666 A | 5/1986 |
| JP | 5-017431 A | 1/1993 |
| WO | WO-98/42674 A1 | 10/1998 |
| WO | WO-98/42675 A1 | 10/1998 |
| WO | WO-98/47534 A1 | 10/1998 |
| WO | WO-2004/035869 A1 | 4/2004 |

(Continued)

OTHER PUBLICATIONS

"Chinese Application Serial No. 201080047362.6, Response filed May 19, 2013 to Office Action mailed Dec. 25, 2012", (w/ English Translation of Amendments), 19 pgs.

(Continued)

*Primary Examiner* — Sreeni Padmanabhan
*Assistant Examiner* — Irina Neagu
(74) *Attorney, Agent, or Firm* — Schwegmen, Lundberg & Woessner, P.A.

(57) ABSTRACT

The invention provides neuromuscular blockade agents of the non-depolarizing type with few if any circulatory effects. Compounds of the invention include bis(isoquinolylalkanol) diesters of fumaric, maleic, succinic, and acetylenedicarboxylic acids; compositions suitable for parenteral administration of these compounds as a surgical adjunct to anesthesia, and methods of preparation of the compounds. Compounds of the invention can produce neuromuscular blockade of short or intermediate duration, which for various compounds can be reversed by administration of a thiol compound such as L-cysteine, D-cysteine or glutathione. For various compounds of the invention, the neuromuscular blockade effect can be reversed quickly, efficiently, and without notable side-effects.

58 Claims, 3 Drawing Sheets

(56) References Cited

FOREIGN PATENT DOCUMENTS

| WO | WO-2005/041960 A2 | 5/2005 |
|---|---|---|
| WO | WO-2007/074454 A2 | 7/2007 |
| WO | WO-2008/070121 A1 | 6/2008 |
| WO | WO-2010/107488 A1 | 9/2010 |
| WO | WO-2011/0022491 A1 | 2/2011 |

OTHER PUBLICATIONS

"U.S. Appl. No. 10/975,197, Advisory Action mailed Jan. 24, 2007", 3 pgs.

"U.S. Appl. No. 10/975,197, Final Office Action mailed Sep. 26, 2006", 16 pgs.

"U.S. Appl. No. 10/975,197, Final Office Action mailed Oct. 18, 2007", 15 pgs.

"U.S. Appl. No. 10/975,197, Interview Summary mailed Sep. 17, 2008", 2 pgs.

"U.S. Appl. No. 10/975,197, Non-Final Office Action mailed Feb. 24, 2006", 9 pgs.

"U.S. Appl. No. 10/975,197, Non-Final Office Action mailed May 2, 2007", 13 pgs.

"U.S. Appl. No, 10/975,197, Response and Declaration filed Jul. 24, 2006 to Non-Final Office Action mailed Feb. 24, 2006", 23 pgs.

"U.S. Appl. No. 10/975,197, Response filed Jan. 13, 2006 to Restriction Requirement mailed Dec. 27, 2005", 10 pgs.

"U.S. Appl. No. 10/975,197, Response filed Jul. 30, 2007 to Non-Final Office Action mailed May 2, 2007", 17 pgs.

"U.S. Appl. No. 10/975,197, Response filed Oct. 30, 2007 to Final Office Action mailed Oct. 18, 2007", 17 pgs.

"U.S. Appl. No. 10/975,197, Response filed Dec. 22, 2006 to Final Office Action mailed Sep. 26, 2006", 13 pgs.

"U.S. Appl. No. 10/975,197, Restriction Requirement mailed Dec. 27,", 5 pgs.

"U.S. Appl. No. 10/975197, Non-Final Office Action mailed Feb. 4, 2008", 17 pgs.

"U.S. Appl. No. 11/951,114 Response filed Oct. 14, 2010 to Restriction Requirement mailed Jul. 16, 2010", 40 pgs.

"U.S. Appl. No. 11/951,114 Restriction Requirement mailed Jul. 16, 2010", 7 pgs.

"U.S. Appl. No. 11/951,114, Non Final Office Action mailed May 25, 2011", 7 pgs.

"U.S. Appl. No. 11/951,114, Non Final Office Action mailed Dec. 15, 2010", 6 pgs.

"U.S. Appl. No. 11/951,114, Notice of Allowance mailed Nov. 30, 2011", 9 pgs.

"U.S. Appl. No. 11/951,114, Preliminary Amendment filed Jan. 7, 2009", 16 pgs.

"U.S. Appl. No. 11/951,114, Response filed Mar. 15, 2011 to Non Final Office Action mailed Dec. 15, 2010", 12 pgs.

"U.S. Appl. No. 11/951,114, Response filed Sep. 26, 2011 to Non Final Office Action mailed May 25, 2011", 15 pgs.

"Australian Application Serial No. 2007328210, Examiner Report mailed Apr. 13, 2012", 2 pgs.

"Australian Application Serial. No. 2007328210, Response filed Oct. 22, 2012 to Office Action mailed Apr. 13, 2012", 15 pgs.

"Canadian Application Serial No. 2,671,904, Office Action mailed Jun. 15, 2011", 3 pgs.

"Canadian Application Serial No. 2,671,904, Response filed Sep. 14, 2011 to Office Action mailed Jun. 15, 2011", 30 pgs.

"Chinese Application Serial No. 200780050532.4, Office Action mailed May 18, 2012", (w/ English Translation), 7 pgs.

"Chinese Application Serial No. 200780050532.4, Office Action mailed Sep. 20, 2010", (w/ English Translation), 10 pgs.

"Chinese Application Serial No. 200780050532.4, Response filed Feg. 5, 2011 to Office Action mailed Sep. 20, 2010", (w/ English Translation of Claims), 15 pgs.

"Chinese Application Serial No. 200780050532.4, Response filed Jul. 31, 2012 to Office Action mailed May 18, 2012", (w/ English Translation of Amended Claims), 8 pgs.

"Chinese Application Serial No. 200780050532.4, Response filed Dec. 8, 2011 to Office Action mailed Sep. 26, 2011", (w/ English Translation of Claims), 22 pgs.

"Chinese Application Serial No. 200780050532,4, Second Office Action mailed Sep. 26, 2011", (w/ English Translation), 11 pgs.

"Chinese Application Serial No. 201080047362.6, Office Action mailed Dec. 25, 2012", (w/ English Translation), 17 pgs.

"Database WPI Week 199309", Thomson Scientific, London, GB; AN 1993-071085, JP 5 017431 A (Seiko Epson Corp), (Jan. 26, 1993), 2 pgs.

"Database WPI Week 200923", Thomson Scientific, London, GB; AN 2009-G02209, CN 101366695A (Jiangsu Sihuan Biological Co Ltd), (Feb. 18, 2009), 2 pgs.

"European Application Serial No. 07862551.4, Response filed Jun. 2, 2011 to Office Action dated Nov. 25, 2010", 9 pgs.

"European Application Serial No. 07862551,4, Supplemental European Search Report mailed Oct. 29, 2010", 7 pgs.

"Indian Application Serial No. 2432/KOLNP/2009 , Voluntary Amendment filed Nov. 22, 2010", 25 pgs.

"International Application U.S. Appl. No. PCT/US07/24914, International Search Report mailed Apr. 17, 2008", 3 pgs.

"International Application Serial No. PCT/US07/24914, Written Opinion mailed Apr. 17, 2008", 8 pgs.

"International Application Serial No. PCT/US2004/035869, International Preliminary Report on Patentability mailed May 11, 2006", 9 pgs.

"International Application Serial No. PCT/US2004/035869, International Search Report mailed May 3, 2005", 3 pgs.

"International Application Serial No. PCT/US2004/035869, Written Opinion mailed May 3, 2005", 9 pgs.

"International Application Serial No. PCT/US2010/000796, International Preliminary Report on Patentability mailed Sep. 29, 2011", 12 pgs.

"International Application Serial No. PCT/US2010/000796, International Search Report mailed Aug. 4, 2010", 2 pgs.

"International Application Serial No. PCT/US2010/000796, Written Opinion mailed Aug. 4, 2010", 13 pgs.

"International Application Serial No. PCT/US2010/045907, International Preliminary Report on Patentability mailed Mar. 1, 2010", 8 pgs.

"International Application Serial No. PCT/US2010/045907, International Search Report mailed Nov. 20, 2010", 4 pgs.

"International Application Serial No. PCT/US2010/045907, Written Opinion mailed Nov. 10, 2010", 8 pgs.

"Japanese Application U.S. Appl. No. 2009-540280, Amendment and Request for Examination filed Dec . 3, 2010", (w/ English Translation of Amended Claims), 83 pgs.

"Japanese Application Serial No. 2009-540280, Office Action mailed Nov. 16, 2012", With English Translation, 5 pgs.

"Japanese Application Serial No. 2009-540280, Response filed Jan. 30, 2013 to Office Action mailed Nov. 16, 2012", (w/ English Translastion of Claims), 15 pgs.

"Le Chatelier's Principle", [online]. © Jim Clark 2002. Retrieved from the Internet: <URL: http://www.chemguide.co.uk/physical/equilibria/echatelier.html>, (2002), 6 pgs.

"Rate equation", http://en.wikipedia.org/wiki/rRate_equation, *Wikipedia® The Free Encyclopedia*, (Aug. 8, 2006), 6 pgs.

Agoston, S., et al., "The Neuromuscular Blocking Action of Org NC 45, A New Pancuronium Derivative, in Anaesthetized Patients", *British Journal of Anaesthesia*, 52(Supplement 1), (1980), 53S-59S.

Baird, W. L. M., et al., "A New Neuromuscular Blocking Drug, Org NC 45", *British Journal of Anaesthesia*, 52(Supplement 1), (1980), 61S-62S.

Bedford, R. F., "From the FDA", *Anesthesiology*, 82, (1995), p. 33A.

Belmont, M. R., "Succinylcholine/Suxamethonium", *Current Opinion in Anaesthesiology*, 8, (1995), 362-366.

Bencini, A., et al., "Use of the Human "Isolated Arm" Preparation to Indicate Qualitative Aspects of a New Neuromuscular Blocking Agent, Org NC 45", *British Journal of Anaesthesia*, 52(Supplement 1), (1980), 43S-47S.

Bevan, D. R., "Newer Neuromuscular Blocking Agents", *Pharmacology & Toxicology*, 74(1), (1994), 3-9.

(56) References Cited

OTHER PUBLICATIONS

Boros, E. E, et al., "Bis- and Mixed-Tetrahydroisoquinolinium Short-Acting Nondepolarizing Neuromuscular Blockers", *J Med Chem.*, 42(2), (1999), 206-209.

Boros, E. E, et al., "Neuromuscular Blocking Activity and Therapeutic Potential of Mixed-Tetrahydroisoquinolinium Halofumarates and Halosuccinates in Rhesus Monkeys", *J Med Chem.*, 46(12), (Jun. 5, 2003), 2502-2015.

Buckett, W. R., et al., "Pancuronium Bromide and Other Steroidal Neuromuscular Blocking Agents Containing Acetylcholine Fragments", *Journal of Medicinal Chemistry*, 16(10), (1973), 1116-1124.

Buzello, W., "The New Non-Depolarizing Muscle Relaxant Org NC 45 in Clinical Anaesthesia: Preliminary Results", *British Journal of Anaesthesia*, 52(Supplement 1), (1980), 62S-64S.

Crul, J. F., et al., "First Clinical Experiences With Org NC 45", *British Journal of Anaesthesia*, 52(Supplement 1), (1980), 49S-52S.

De Rosa, S. C, "N-acetylcysteine Replenishes Glutathione in HIV Infection", European *Journal of Clinical Investigation*, 30, (2000), 915-929.

Dizdar, N., et al., "Comparison of N-acetylcysteine and $_L$-2-oxothiazolidine-4-carboxylate as cysteine deliverers and glutathione Precursors in Human Malignant Melanoma Transplants in Mice", *Cancer Chemother Pharmacol*, 45, (2000), 192-198.

Durant, N. N., et al., "Suxamethonium", *British Journal of Anaesthology*, 54, (1982), 195-208.

Fahey, M. R., et al., "Clinical Pharmacology of ORG NC45 (Norcuron™): A New Nondepolarizing Muscle Relaxant", *Anesthesiology*, 55(1), (1981), 6-11.

Foldes, F. F., et al., "Influence of Halothane and Enflurane on the Neuromuscular Effects of Org NC 45 in Man", *British Journal of Anaesthesia*, 52(Supplement 1), (1980), 64S-65S.

Huang, T. C., et al., "Mechanistic Studies on Thiazolidine Formation in Aldehyde/Cysteamine Model Systems", *J Agric Food Chem.*, 46(1), (Jan. 1998), 224-227.

Kharkevich, D. A. "New Curare-Like Agents", *J. Pharm. Pharmac.*, 26, (1974), 153-165.

Khromov-Borisov, N. V., et al., "Removal of a Curare-Like Effect by Direct Inactivation of the Myorelaxant Molecule by Disruption of the Disulfide Bond", *Doklady Biological Sciences, Proceedings of the Academy of Sciences of the USSR*, 186(1), (1968), 460-463.

Kreig, N., et al., "Preliminary Review of the Interactions of Org NC 45 With Anaesthetics and Antibiotics in Animals", *British Journal of Anaesthesia*, 52 (Supplement 1), (1980), 33S-36S.

Kulawska, M,, et al., "Kinetics of the esterification of maleic anhydride with octyl, decyl or dodecyl alcohol over dowex catalyst", Abstract Only), *Reaction Kinetics and Catalysis Letters*, vol. 85(1), (2005), 2 pgs.

Lee, C., "Structure, Conformation, and Action of Neuromuscular Blocking Drugs", *British Journal of Anaesthesia*, 87(5), (2001), 755-769.

Li, J., et al., "Dietary supplementation with cysteine prodrugs selectively restores tissue glutathione levels and redox status in protein-malnourished mice". *Journal of Nutritional Biochemistry*,13, (2002), 625-633.

Lien, C. A, "The Pharmacology of GW280430A: A New Nondepolarizing Neuromuscular Blocking Agent", *Seminars in Anesthesia: Perioperative Medicine and Pain*, 21(2), (Jun. 2002), 86-91.

Mahajan, R. P., "Focus on: Controversies in Anaesthesia—Is Suxamethonium Now Obsolete?", *Current Anaesthesia and Critical Care*, 7, (1996), 289-294.

Marshall, I. G., et al., "Pharmacology of Org NC 45 Compared With Other Non-Depolarizing Neuromuscular Blocking Drugs", *British Journal of Anaesthesia*, 52(Supplement 1), (1980), 11S-19S.

Marshall, R. J., et al., "Comparison of the Cardiovascular Actions of Org NC 45 With Those Produced by Other Non-Depolarizing Neuromuscular Blocking Agents in Experimental Animals", *British Journal of Anaesthesia*, 52(Supplement 1), (1980), 21S-32S.

McNulty, M., "The Ultra-Short Acting Nondepolarizing Relaxant GW280430A Undergoes Rapid Degradation by Chemical Mechanisms", *Anesthesiology Abstracts of Scientific Papers Annual Meeting—2002*, (2002), 1 pg.

Miller, R. D., "Org NC 45", *British Journal of Anaesthesia*, 52(Supplement 1), (1980), 71S-72S.

Morrison, R. T., et al., In: *Organic Chemistry* (Second Edition), Allyn and Bacon, Inc., Boston, MA, (1966), 290-293.

Murphy, G.S., "Residual neuromuscular blockade:incidence, assessment, and relevance in the postoperative period", *Minerva Anestesiol*, vol. 72(3), (2006), 97-109.

Naguib, M., et al., "Advances in Neurobiology of the Neuromuscular Junction", *Anesthesiology*, 96(1), (2002), 202-231.

Nebergall, W. H., "Chapter 7—Molecular Structure and Hybridization", In: *General Chemistry* (6th Edition), D. C. Heath and Company, (1980), 149-152.

Norman, J., et al., "Introduction", *British Journal of Anaesthesia*, 52(Supplement 1), (1980), S1-S2.

Rees, D. C. et al., "Chapter 5. Drugs in Anesthetic Practice", *Annual Reports in Medicinal Chemistry*, 31, (1994), 41-50.

Reese, M J, "Comparative Metabolic Profiles of the Neuromuscular Blocker GW280430 in Human, Monkey, and Dog, and Characterization of a Major Metabolite as an Unusal Cyclized Cysteine conjugate", (Abstract 282), Presented at the 9th North American ISSX Meeting (issx.org); Nashville, TN, (Oct. 1999), p. 142.

Saitoh, Y., et al., "Infusion of Amino Acid Enriched Solution Hastens Recovery From Neuromuscular Block Caused by Vecuronium", *British Journal of Anaesthesia*, 86, (2001), 814-821.

Sakuraba, H., et al,, "Asymmetric Michael Addition of Aromatic Thiols to 2-Cyclohexenone and Maleic Acid Esters Via Formation of Crysatiline Cyclodextrin Complexes", *Journal of Inclusion Phenomena and Molecular Recognition in Chemistry*, (1991), 195-204.

Savage, D. S., et al., "The Emergence of ORG NC 45, 1-[(2beta,3alpha,16beta,17beta)-3, 17-Bis(Acetylox)2-(1-Piperidinyl)-Androstan-16-YL]-1-Methylpiperidinium Bromide, From the Pancuronium Series", *British Journal of Anaesthesia*, 52(Supplement 1), (1980), 3S-9S.

Savarese, J. J., et al., "Chapter 14. Pharmacology of Muscle Relaxants and Their Antagonists", In: *Anestheisa*, vol. 1, (Fourth Edition), Miller, R. D., et al., Editors, Churchil Livingstone Inc. (1994), 417-487.

Savarese, J. J, et al., "Rapid chemical antagonism of neuromuscular blockade by L-cysteine adduction to and inactivation of the olefinic (double-bonded) isoquinolinium diester compounds gantacurium (AV430A), CW 002, and CW 011.", *Anesthesiology*, 113(1), (Jul. 2010), 58-73.

Schaer, H., et al., "Preliminary Clinical Observations With Org NC 45", *British Journal of Anaesthesia*, 52(Supplement 1), (1980), 65S-67S.

Son, S. L., et al., "A Comparison of the Neuromuscular Blocking and Vagolytic Effects of ORG NC45 and Pancuronium", *Anesthesiolog*, 55(1), (1981), 12-18.

Speight, T. M., et al., "Pancuronium Bromide: A Review of its Pharmacological Properties and Clinical Application", *Drugs*, 4(1-2), (1972), 163-226.

Sunaga, H., et al, "Cysteine reversal of the novel neuromuscular blocking drug CW002 in dogs: pharmacodynamics, acute cardiovascular effects, and preliminary toxicology.", *Anesthesiology*, 112(4), (Apr. 2010), 900-909.

Van Der Veen, F., et al., "Pharmacokinetics and Pharmacodynamics of Org NC 45 in Man", *British Journal of Anaesthesia*, 52(Supplement 1), (1980), 37S-41S.

Viby-Mogensen, J., et al., "On Org NC 45 and Halothane Anaesthesia", *British Journal of Anaesthesia*, 52(Supplement 1), (1980), 37S-41S.

Zhang, L. et al., "Thiazolidine formation as a general and site-specific conjugation method for synthetic peptides and proteins", *Anal Biochem.*, 233(1), (Jan. 1, 1996), 87-93.

REVERSIBLE NONDEPOLARIZING NEUROMUSCULAR BLOCKADE AGENTS AND METHODS FOR THEIR USE

RELATED APPLICATIONS

This application is a nationalization under 35 U.S.C. 371 of PCT/US2010/000796, filed Mar. 17, 2010 and published as WO 2010/107488 A1 on Sep. 23, 2010, which claims priority to U.S. provisional application Ser. No. 61/160,915, filed Mar. 17, 2009; which applications and publications are incorporated herein by reference in their entirety.

BACKGROUND

Neuromuscular blockade agents are molecular entities that interfere with nerve stimulation of skeletal muscles by action at the neuromuscular junction. They are particularly useful in surgery, acting to paralyze muscular movement, which is desirable particularly in intra-abdominal and intra-thoracic surgery. Given in conjunction with anesthetics, neuromuscular blockade agents aid in immobilization of the patient to facilitate delicate surgical operations. Historically, these drugs are derived from curare, an alkaloid found in South American plants and used as an arrow poison. Modern examples include succinylcholine, Atracurium, and Doxacurium. See, for example, the published PCT application WO2005/041960, by the inventor herein, and documents cited therein.

Because these agents can also cause paralysis of the diaphragm, tracheal intubation and mechanical respiration is typically required when neuromuscular blocking agents are used during surgery. When surgery is complete, there is generally no medical reason to continue the blockade, but the agents can take a period of time for their effects to cease.

SUMMARY

The present invention is directed to novel neuromuscular blockade agents, to methods of using the agents, and to methods of preparing the agents.

In various embodiments, the invention provides a compound of formula (I)

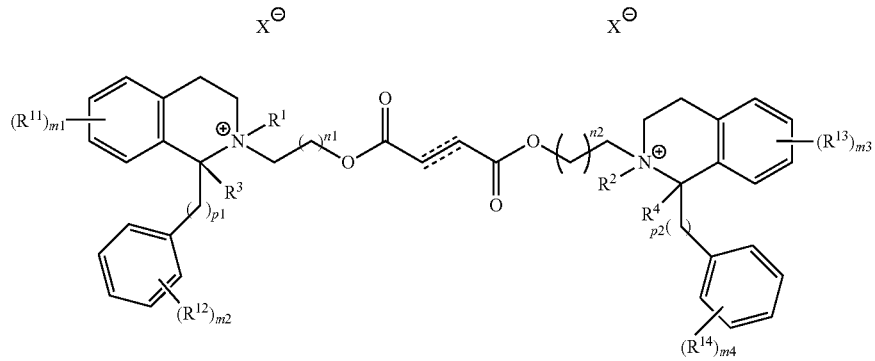

wherein a double dashed line indicates that a single bond or a double bond or a triple bond is present at that position; the double bond, when present, is of Z or E configuration and each carbon atom of the double bond is substituted with a single respective hydrogen atom; for the single bond, when present, each carbon atom bears two respective hydrogen atoms;

$R^1$ and $R^2$ are each independently $(C_1-C_4)$alkyl, $(C_1-C_4)$alkenyl, or $(C_1-C_4)$alkynyl;

$R^3$ and $R^4$ are each independently hydrogen or $(C_1-C_4)$alkyl, $(C_1-C_4)$alkenyl, or $(C_1-C_4)$alkynyl;

$R^{11}$, $R^{12}$, $R^{13}$, and $R^{14}$ are each independently $(C_1-C_4)$alkoxy or $(C_1-C_4)$acyloxy; or any two adjacent $R^{11}$, $R^{12}$, $R^{13}$, or $R^{14}$ are methylenedioxy;

m1 and m3 are each independently 2, 3, or 4;

m2 and m4 are each independently 2 or 3;

n1 and n2 are each independently 1 to about 4;

p1 and p2 are each independently 0 or 1;

X is independently at each occurrence a pharmaceutically acceptable anion;

including any stereoisomer thereof, or, any solvate, hydrate, metabolite or prodrug thereof.

In various embodiments, compounds of the invention can be diesters of maleic acid, fumaric acid, succinic acid, or acetylenedicarboxylic acid, including any stereoisomer thereof, or, any solvate, hydrate, metabolite or prodrug thereof.

In various embodiments of the invention, the compound produces, upon administration of an effective amount of the compound to a patient, a neuromuscular blockade. In various embodiments, the neuromuscular blockage is reversible by administration to the patient of an effective amount of a thiol compound.

In various embodiments, the invention provides a composition comprising a compound of the invention and a pharmaceutically acceptable excipient. In various embodiments the composition is adapted for parenteral administration.

In various embodiments, the invention provides a method of inducing neuromuscular blockade in a patient, comprising administering an effective amount of a compound of the invention to the patient. In various embodiments the invention further provides that the neuromuscular blockade can be reversed by administration, such as parenteral administration of a thiol compound, such as L-cysteine, D-cysteine, or glutathione.

In various embodiments, the invention provides a use of a compound of the invention for creating neuromuscular blockade.

In various embodiments, the invention provides a dosage form of a compound of the invention comprising an injectable solution of the compound in a suitable biocompatible solvent.

In various embodiments, the invention provides a kit comprising a compound of the invention in a first container and a thiol compound suitable for reversing the neuromuscular blockade effect on a patient in a second container.

Figure 1A:
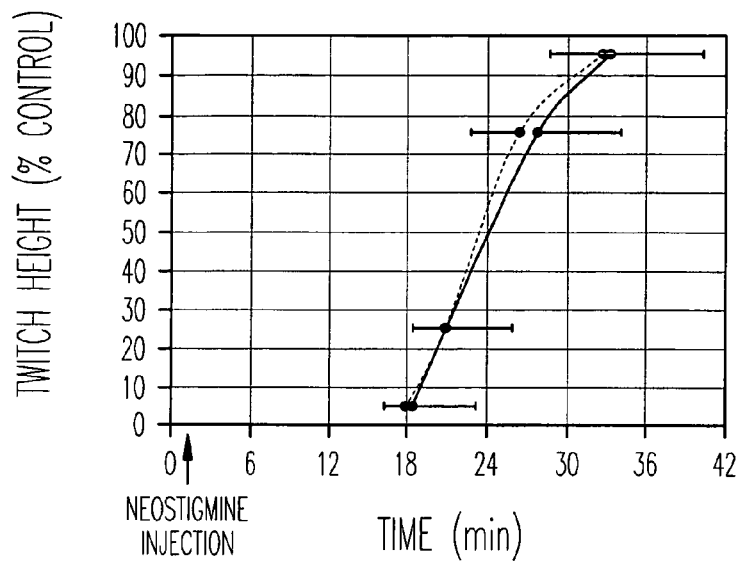
FIG. 1 is a graph showing the immediate antagonism of CW 002 blockade 1 min following CW 002 dosage of 0.15 mg/kg, or ~4× ED 95, injected at t=0. Neostigmine (0.05 mg/kg+atropine 0.05 mg/kg) or L-cysteine (10, 20, 30, or 50 mg/kg) was given at +1 min. Neostigmine did not shorten recovery (A), whereas L-cysteine produced a dose-related acceleration of recovery (B), peaking at 50 mg/kg. Data are from anesthetized rhesus monkeys. Twitch of the extensor digitorum was elicited at 0.15 Hz.

FIG. 2 is a graph showing immediate L-cysteine (50 mg/kg) antagonism of escalating dosage of CW 011 (4 to 64× ED95): comparison of spontaneous recoveries (A) versus recovery accelerated by L-cysteine given at +1 minute after CW 011 (B). CW 011 was injected at t=0. All paired comparisons $p<0.001$. Data are from groups of anesthetized monkeys; twitch of extensor digitorum was elicited at 0.15 Hz.

FIG. 3 is a graph showing the correlation of L-cysteine adduction reaction rate (t½) in vitro with total duration of action (recovery of twitch to 95% of control height) of gantacurium, CW 002 and CW 011 at ~4-5× ED 95 in anesthetized monkeys. $r^2=0.4883$; ($p<0.0001$). Twitch of the extensor digitorum was elicited at 0.15 Hz.

DETAILED DESCRIPTION

Definitions

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

All structures encompassed within a claim are "chemically feasible", by which is meant that the structure depicted by any combination or subcombination of optional substituents meant to be recited by the claim is physically capable of existence with at least some stability as can be determined by the laws of structural chemistry and by experimentation. Structures that are not chemically feasible are not within a claimed set of compounds.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboyxlate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, $CF_3$, $OCF_3$, R', O, S, C(O), S(O), methylenedioxy, ethylenedioxy, N(R')$_2$, SR', SOR', $SO_2$R', $SO_2$N(R')$_2$, $SO_3$R', C(O)R', C(O)C(O)R', C(O)$CH_2$C(O)R', C(S)R', C(O)OR', OC(O)R', C(O)N(R)$_2$, OC(O)N(R')$_2$, C(S)N(R')$_2$, $(CH_2)_{0-2}$NHC(O)R', N(R')N(R')C(O)R', N(R')N(R')C(O)OR', N(R')N(R')CON(R')$_2$, N(R')$SO_2$R', N(R')$SO_2$N(R')$_2$, N(R')C(O )OR', N(R')C(O)R', N(R')C(S)R', N(R)C(O )N(R')$_2$, N(R')C(S)N(R')$_2$, N(COR')COR', N(OR')R', N(R')C(=NR)N(R')$_2$, C(=NH)N(R')$_2$, N(R')C(=NH)N(R')$_2$, C(O)N(OR')R', or C(=NOR')R' wherein R' can be hydrogen or a carbon-based moiety, and wherein the carbon-based moiety can itself be further substituted. Further, any substituent can be bonded to a carbon or other atom by a linker, such as $(CH_2)_n$ or $(CR'_2)_n$ wherein n is 1, 2, 3, or more, and each R' is independently selected.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring systems such as substituted aryl, heterocyclyl and heteroaryl groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic.

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S(O)—R') and sulfones (R—S(O)$_2$-R'), unless the oxidation state is specified; thus, the term "sulfone" encompasses only the sulfone form of sulfur; the term "sulfide" encompasses only the sulfide (R—S—R') form of sulfur. When the phrases such as "heteroatoms selected from the group consisting of O, NH, NR' and S," or "[variable] is O, S . . . " are used, they are understood to encompass all of the sulfide, sulfoxide and sulfone oxidation states of sulfur.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups.

Cycloalkyl groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH(CH3), —CH═C(CH3)2, —C(CH3)═CH2, —C(CH3)═CH(CH3), —C(CH2CH3)═CH2, cyclohexenyl, cyclopentenyl, cyclohexadienyl, butadienyl, pentadienyl, and hexadienyl among others.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as, but not limited to, 2-, 3-, 4-, 5-, or 6-substituted phenyl or naphthyl groups, which can be substituted with groups including but not limited to those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. The aryl moiety or the alkyl moiety or both are optionally substituted with other groups, including but not limited to alkyl, halo, amino, hydroxy, cyano, carboxy, nitro, thio, or alkoxy groups. Aralkenyl group are alkenyl groups as defined above in which a hydrogen or carbon bond of an alkyl group is replaced with a bond to an aryl group as defined above.

Heterocyclyl groups include aromatic and non-aromatic ring compounds containing 3 or more ring members, of which one or more is a heteroatom such as, but not limited to, N, O, S, or P. In some embodiments, heterocyclyl groups include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms.

The phrase "heterocyclyl group" includes fused ring species including those having fused aromatic and non-aromatic groups. The phrase also includes polycyclic ring systems containing a heteroatom such as, but not limited to, quinuclidyl and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heterocyclyl groups can be substituted. Representative substituted heterocyclyl groups can be mono-substituted or substituted more than once, including but not limited to, rings containing at least one heteroatom which are mono, di, tri, tetra, penta, hexa, or higher-substituted with substituents such as those listed above, including but not limited to alkyl, halo, amino, hydroxy, cyano, carboxy, nitro, thio, and alkoxy groups.

Heteroaryl groups are aromatic ring compounds containing 5 or more ring members, of which, one or more is a heteroatom such as, but not limited to, N, O, and S. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl. The term also includes heteroaryl groups that have other groups bonded to one of the ring members, including but not limited to alkyl, halo, amino, hydroxy, cyano, carboxy, nitro, thio, or alkoxy groups. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (242,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-2-yl methyl ($\alpha$-picolyl), pyridine-3-yl methyl ($\beta$-picolyl), pyridine-4-yl methyl ($\gamma$-picolyl), tetrahydrofuran-2-yl ethyl, and indol-2-yl propyl. Heterocyclylalkyl groups can be substituted on the heterocyclyl moiety, the alkyl moiety, or both.

Heteroarylalkyl groups are alkyl groups as defined above in which a hydrogen or carbon bond of an alkyl group is replaced with a bond to a heteroaryl group as defined above. Heteroarylalkyl groups can be substituted on the heteroaryl moiety, the alkyl moiety, or both.

A "monocyclic, bicyclic or polycyclic, aromatic or partially aromatic ring" as the term is used herein refers to a ring system including an unsaturated ring possessing 4n+2 pi electrons, or a partially reduced (hydrogenated) form thereof. The aromatic or partially aromatic ring can include additional fused, bridged, or spiro rings that are not themselves aromatic or partially aromatic. For example, naphthalene and tetrahydronaphthalene are both a "monocyclic, bicyclic or polycyclic, aromatic or partially aromatic ring" within the meaning herein. Also, for example, a benzo-[2.2.2]-bicyclooctane is also a "monocyclic, bicyclic or polycyclic, aromatic or partially aromatic ring" within the meaning herein, containing a phenyl ring fused to a bridged bicyclic system.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

The term "amine" (or "amino"), where referring to a compound, includes primary, secondary, tertiary amines and quaternary ammonium salts, and to molecules containing one or more amino groups. When referring to a substituent group, the terms include functional groups having a basic nitrogen in free, salt, or quaternarized form, e.g., the formula —NR$_2$ or —NR$_3^+$ wherein each R can independently be hydrogen, alkyl, aryl, heterocyclyl, and the like.

Amino groups include, but are not limited to, —NH$_2$, alkylamino, dialkylamino, arylamino, alkylarylamino, diarylamino, aralkylamino, and heterocyclylamino groups and the like. Quarternary ammonium salts are amine or amino groups within the meaning herein, for example a trimethylammonium group bonded to a carbon moiety is an amino group. Thus, trimethylammonium hydrochloride and tetramethylammonium chloride are both ammonium ions, and amines, within the meaning herein.

The term "amide" ("carboxamido" or "amido") includes C- and N-amide groups, i.e., —C(O)NR$_2$, and —NRC(O)R groups, respectively. Amide groups therefore include but are not limited to primary amido groups (—C(O)NH$_2$) and formamido groups (—NHC(O)H).

The term "urethane" (or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$).

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$. "Halo," "halogen," and "halide" include fluorine, chlorine, bromine and iodine.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

In various embodiments, the compound or set of compounds, either per se or as are used in practice of embodiments of the inventive methods, can be any one of any of the combinations and/or sub-combinations of the various embodiments recited.

Detailed Description

In various embodiments, the invention provides a compound of formula (I)

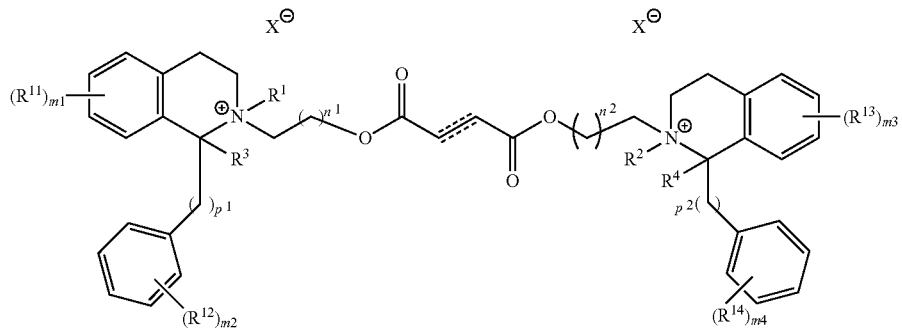

wherein
a double dashed line indicates that a single bond or a double bond or a triple bond is present at that position; the double bond, when present, is of Z or E configuration and each carbon atom of the double bond is substituted with a single respective hydrogen atom; for the single bond, when present, each carbon atom bears two respective hydrogen atoms;

$R^1$ and $R^2$ are each independently (C$_1$-C$_4$)alkyl, (C$_1$-C$_4$) alkenyl, or (C$_1$-C$_4$)alkynyl;

$R^3$ and $R^4$ are each independently hydrogen or (C$_1$-C$_4$) alkyl, (C$_1$-C$_4$)alkenyl, or (C$_1$-C$_4$)alkynyl;

$R^{11}$, $R^{12}$, $R^{13}$, and $R^{14}$ are each independently (C$_1$-C$_4$) alkoxy or (C$_1$-C$_4$)acyloxy; or any two adjacent $R^{11}$, $R^{12}$, $R^{13}$, or $R^{14}$ are methylenedioxy;

m1 and m3 are each independently 2, 3, or 4;

m2 and m4 are each independently 2 or 3;

n1 and n2 are each independently 1 to about 4;

p1 and p2 are each independently 0 or 1;

X is independently at each occurrence a pharmaceutically acceptable anion;

including any stereoisomer thereof, or, any solvate, hydrate, metabolite or prodrug thereof.

In various embodiments, compounds of the invention can be diesters of maleic acid, fumaric acid, succinic acid, or acetylenedicarboxylic acid, including any stereoisomer thereof, or, any solvate, hydrate, metabolite or prodrug thereof.

Accordingly, in various embodiments, compound of the invention can be compounds wherein the double dashed line indicates a double bond in the Z configuration of the maleate formula

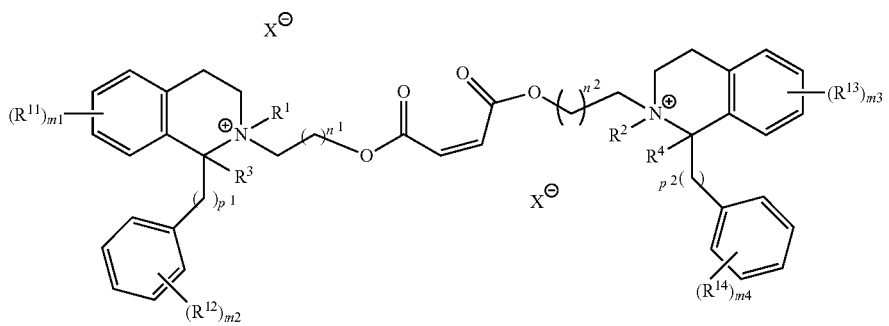

including any stereoisomer thereof, or, any solvate, hydrate, metabolite or prodrug thereof.

Or, compounds of the invention can be compounds wherein the double dashed line indicates a double bond in the E configuration, of the fumarate formula

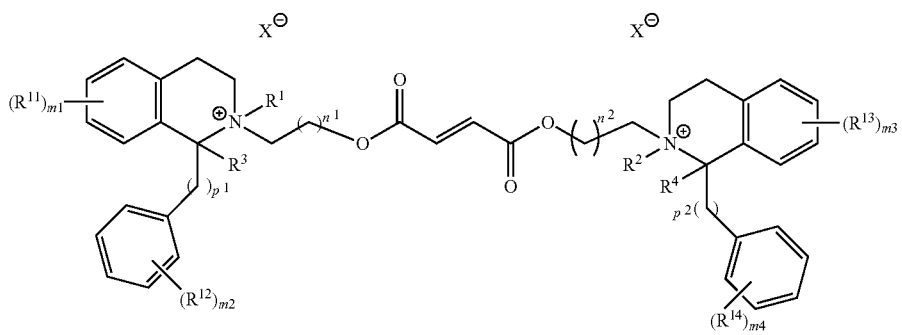

including any stereoisomer thereof, or, any solvate, hydrate, metabolite or prodrug thereof.

Or, compounds of the invention can be compounds wherein the double dashed line indicates a single bond of the succinate formula

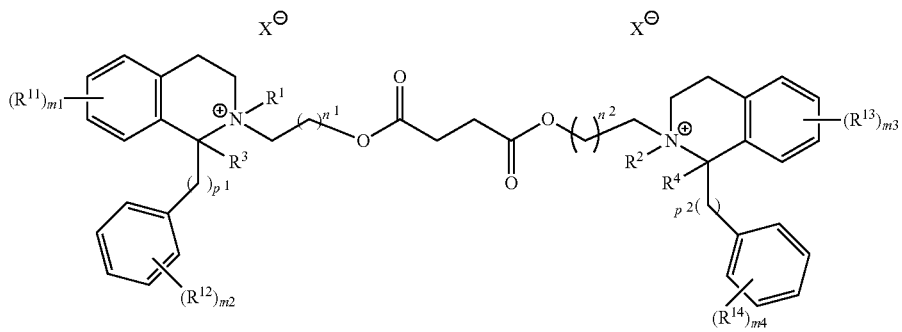

including any stereoisomer thereof, or, any solvate, hydrate, metabolite or prodrug thereof.

Or, compounds of the invention can be compounds wherein the double dashed line indicates a triple bond of the acetylenedicarboxylate formula

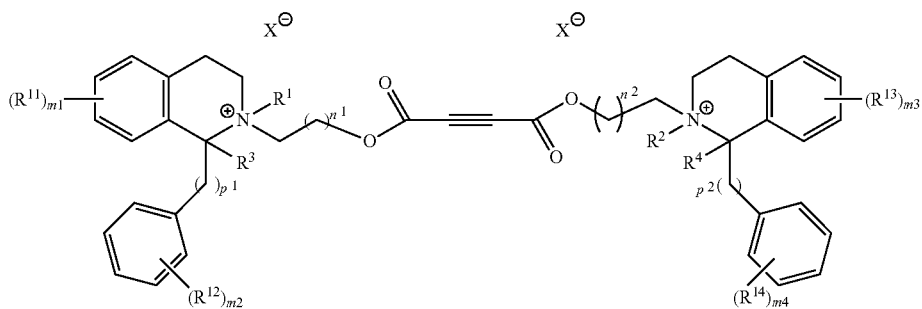

including any stereoisomer thereof, or, any solvate, hydrate, metabolite or prodrug thereof.

Various embodiments are now described wherein particular substituents are more narrowly defined. These embodiments are not intended to limit the invention, but only to provide illustrative examples.

In various embodiments, a compound of the invention can be a compound wherein $R^1$, $R^2$, or both, are methyl.

In various embodiments, a compound of the invention can be a compound wherein the nitrogen atom bearing $R^1$, the nitrogen atom bearing $R^2$, or both nitrogen atoms, are in the S absolute configuration.

In various embodiments, a compound of the invention can be a compound wherein both X are chloride.

In various embodiments, a compound of the invention can comprise an R-trans, R-trans compound of formula (II)

(II)

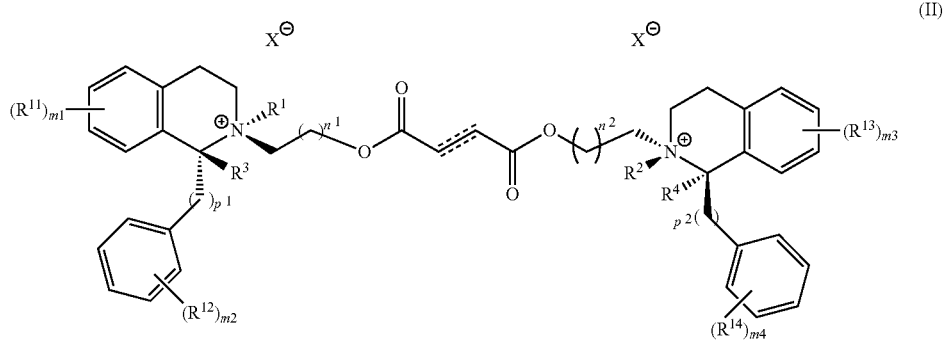

In various embodiments, a compound of the invention can be a compound wherein $R^3$, $R^4$, or both, are hydrogen.

In various embodiments, a compound of the invention can be a compound wherein n1 and n2 are both 2.

In various embodiments, a compound of the invention can be a compound wherein m1 and m3 are each independently 2 or 3.

In various embodiments, a compound of the invention can be a compound wherein m2 and m4 are each independently 2 or 3.

In various embodiments, a compound of the invention can be a compound wherein $R^{11}$, $R^{12}$, $R^{13}$, and $R^{14}$ are all methoxy, or wherein any two of $R^{11}$, any two of $R^{12}$, any two of $R^{13}$, or any two of $R^{14}$, are methylenedioxy, or any combination thereof.

In various embodiments, a compound of the invention can be a compound wherein $R^1$ and $R^3$ are in a trans configuration.

In various embodiments, a compound of the invention can be compounds wherein $R^2$ and $R^4$ are in a trans configuration.

In various embodiments, a compound of the invention can be a compound wherein the carbon atom bearing $R^3$, the carbon atom bearing $R^4$, or both carbon atoms, are in the R absolute configuration.

or any solvate, hydrate, metabolite, or prodrug thereof. By an "R-trans, R-trans" compound is meant a compound having an R absolute stereochemical configuration at each of the carbon atoms bearing groups $R^3$ and $R^4$, wherein the benzyl moieties bonded to those carbon atoms are both disposed trans to the alkanol substituent on the respective adjacent nitrogen atom. Similarly, an "R-cis, R-cis" compound refers to a compound wherein an absolute R stereochemical configuration exists at the two carbon atoms bearing the $R^3$ and $R^4$ groups, wherein the benzyl moieties bonded to those carbon atoms are both disposed cis to the alkanol substituent on the respective adjacent nitrogen atom. In this manner, the stereochemistry of the two isoquinolylalkanol moieties bonded to the two carboxylic acid groups of the fumarate, maleate, succinate, or acetylenedicarboxylate moieties can be fully defined. For example, for a maleate compound (the terminology of which defines the stereochemistry of the central double bond as opposed to a fumarate compound), isomers such as "S-trans, S-trans," "S-trans, R-cis," "R-cis, S-trans," and all the other possible permutations can be specified. The present invention includes all such isomers of the specified generic structures disclosed herein and of all specific structures in which the stereochemistry is otherwise unspecified, encompassing R and S stereoisomers and cis and trans ring configurations in all combinations.

In various embodiments, a compound of the invention can comprise an R-trans, R-trans compound of formula (IIA)

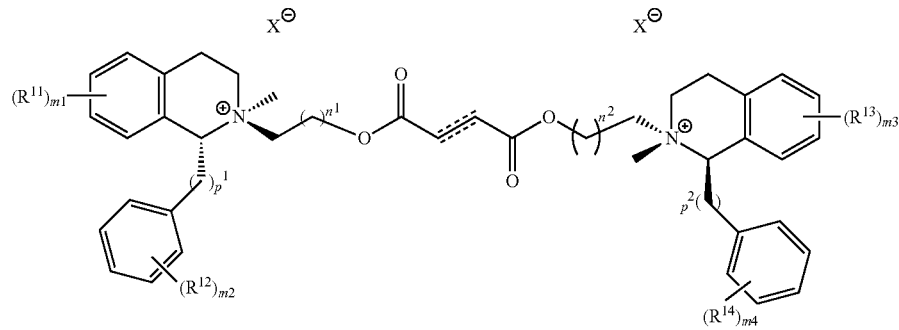

or any solvate, hydrate, metabolite, or prodrug thereof.

In various embodiments, a compound of the invention can be a compound comprising an R-trans, R-trans compound of formula (IIA), wherein n1 and n2 are both equal to 2. For example, an R-trans, R-trans compound of formula (IIA), wherein n1 and n2 are both equal to 2 can be a maleate diester, or a fumarate diester, or a succinate diester, or an acetylenedicarboxylate diester. In various embodiments, for any of these compound, p1 and p2 can both be 1, or one of p1 and p2 is 0 and one of p1 and p2 is 1, or, p1 and p2 are both 0.

In various embodiments, a compound of the invention can be any of the following maleates:

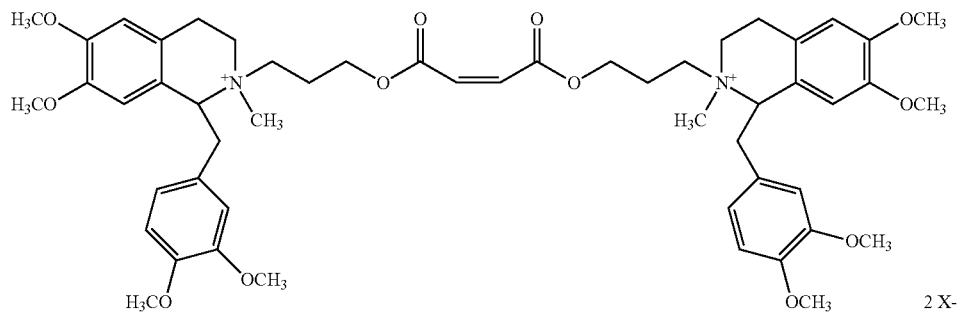

[R-trans, R-trans is NB 968-39]

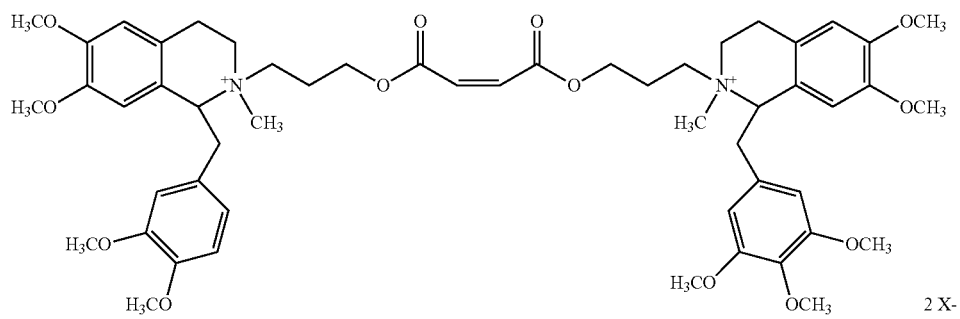

[R-trans, R-trans is NB 1043-46 (CW011)]

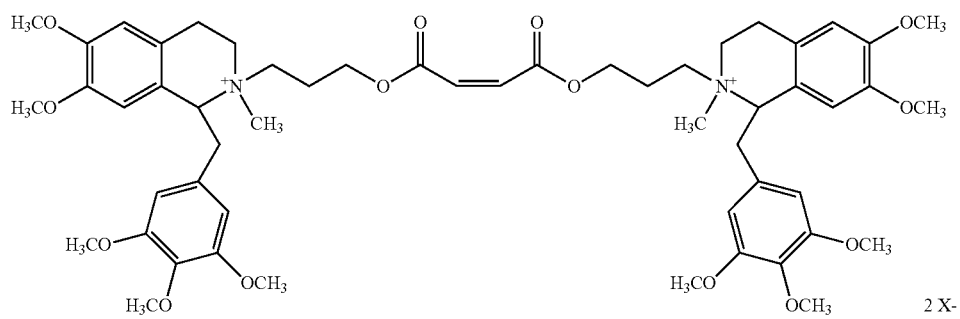

-continued
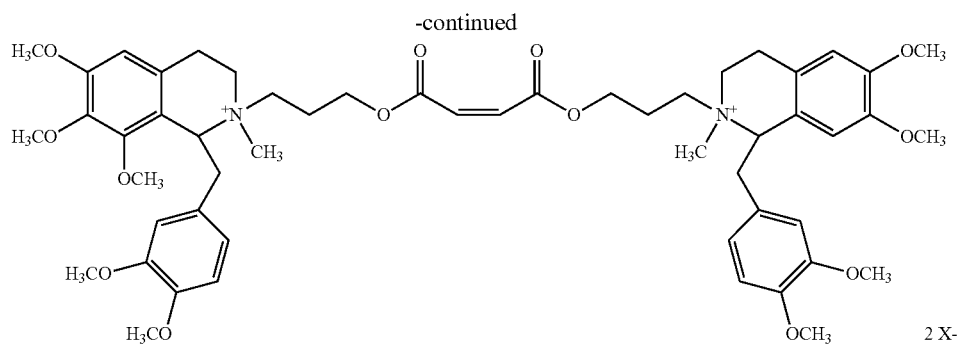
2 X-
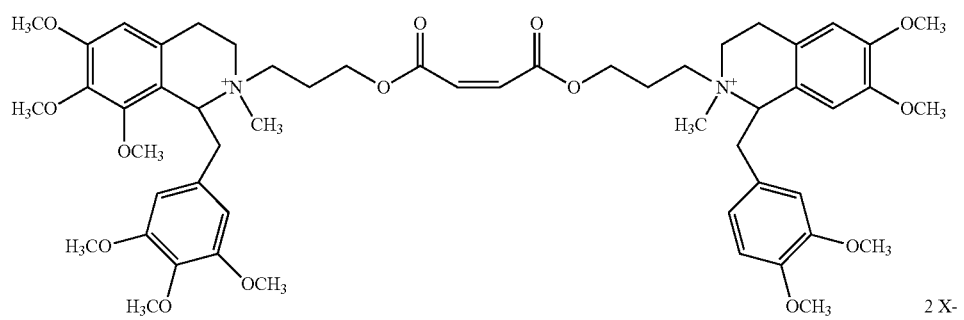
2 X-
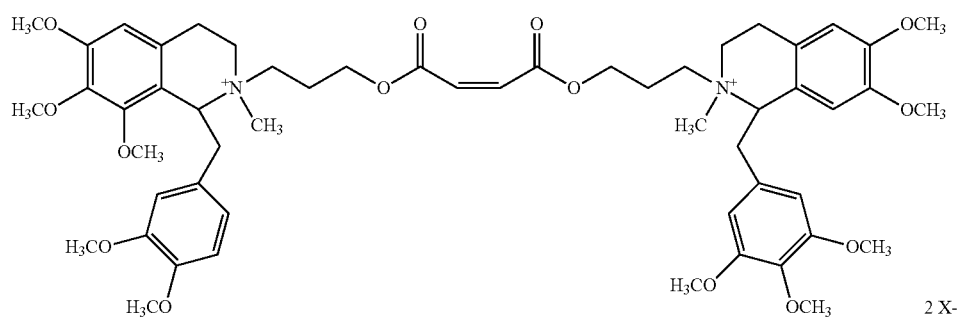
2 X-
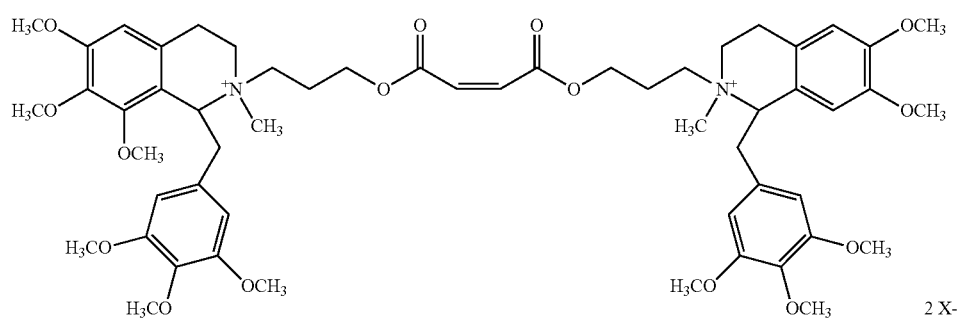
2 X-
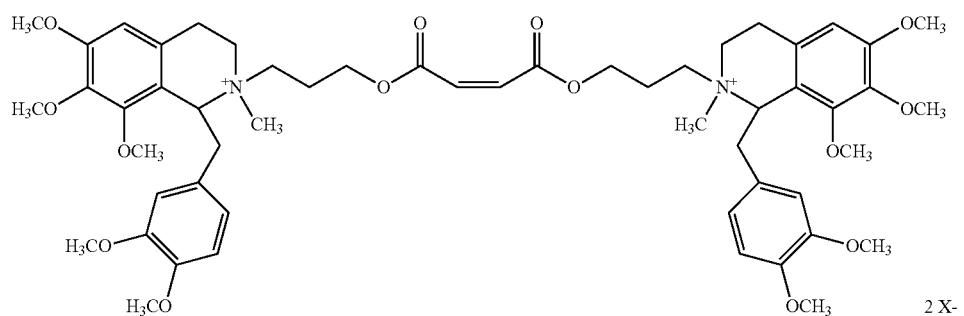
2 X-

-continued
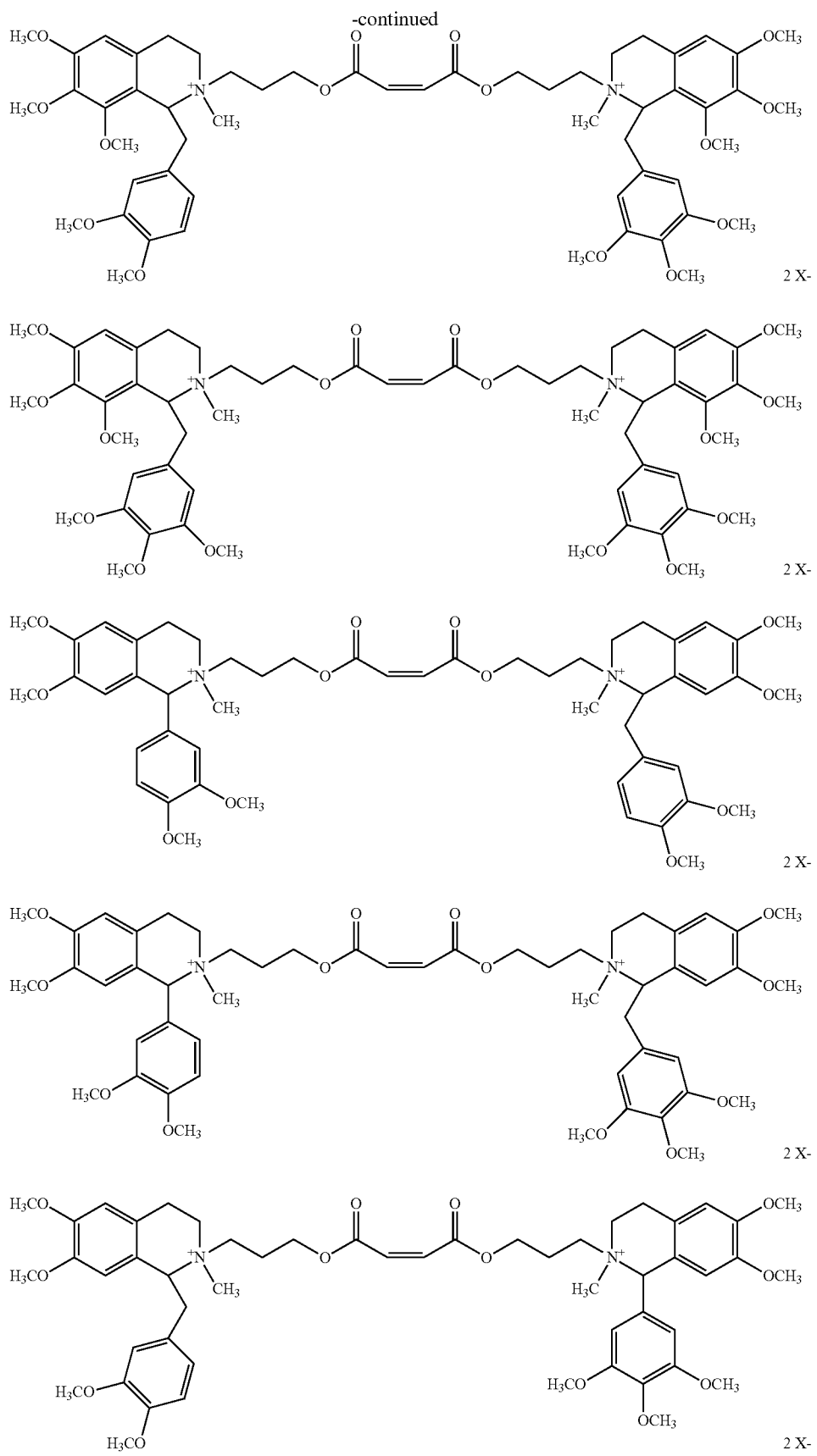
[R-trans, R-trans is NB 1064-81]

-continued
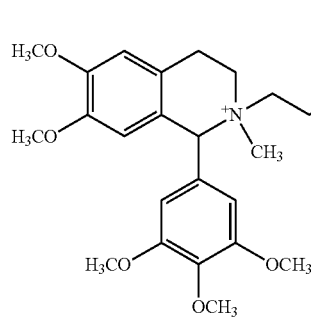 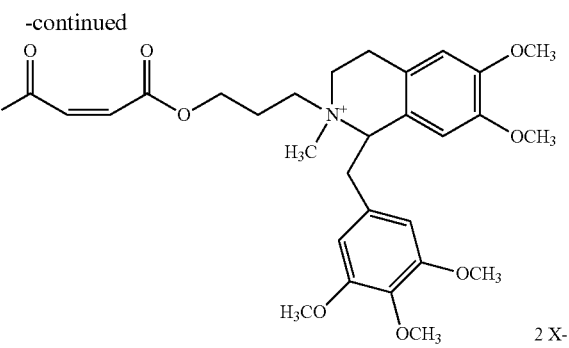
2 X⁻
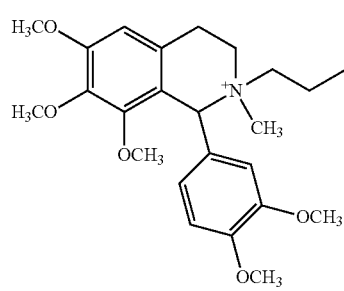 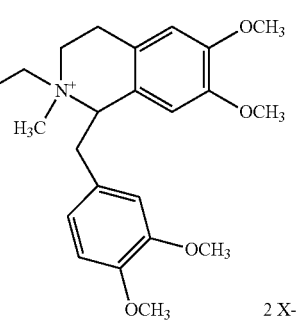
2 X⁻
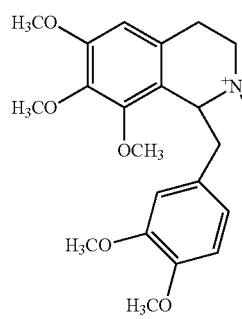 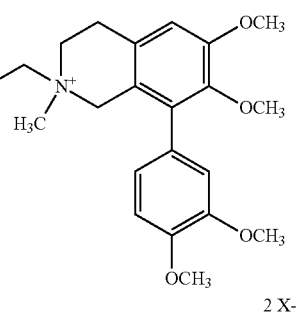
2 X⁻
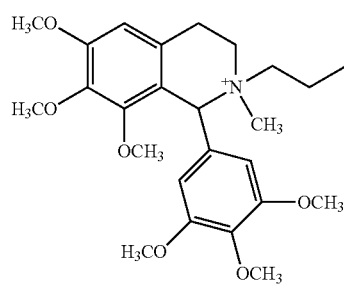 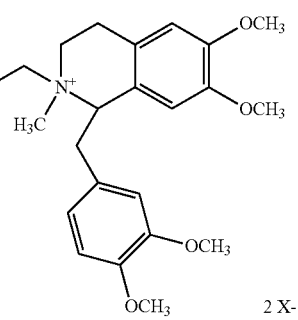
2 X⁻
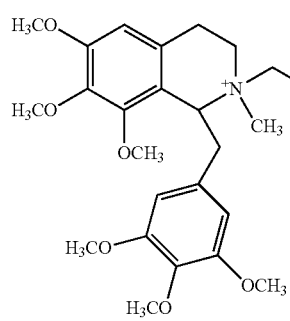 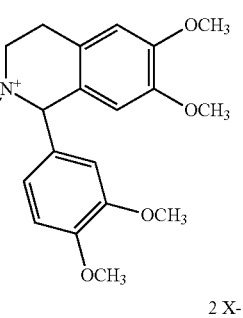
2 X⁻

-continued
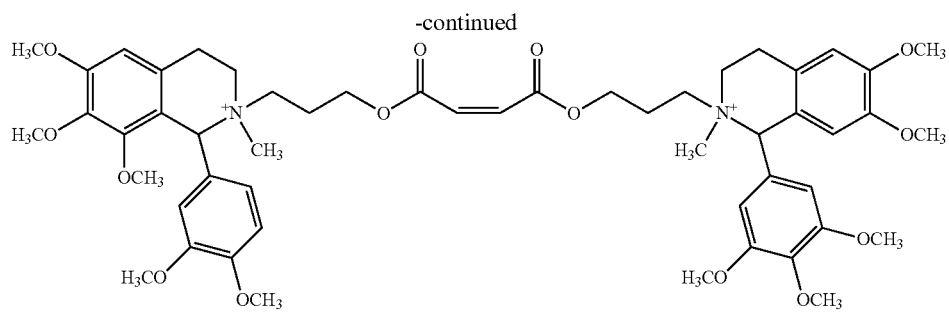
2 X−
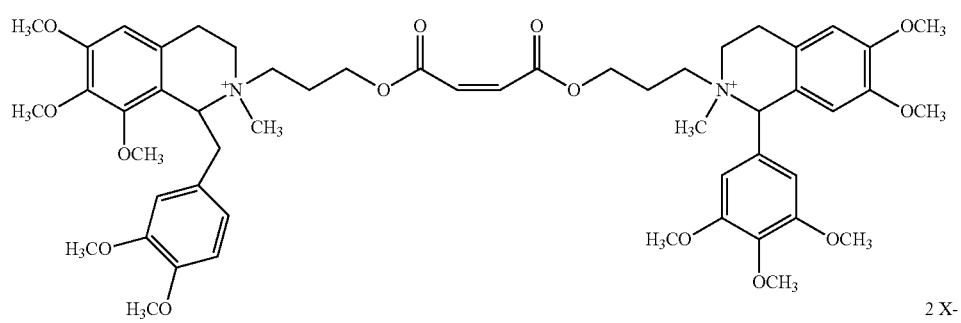
2 X−
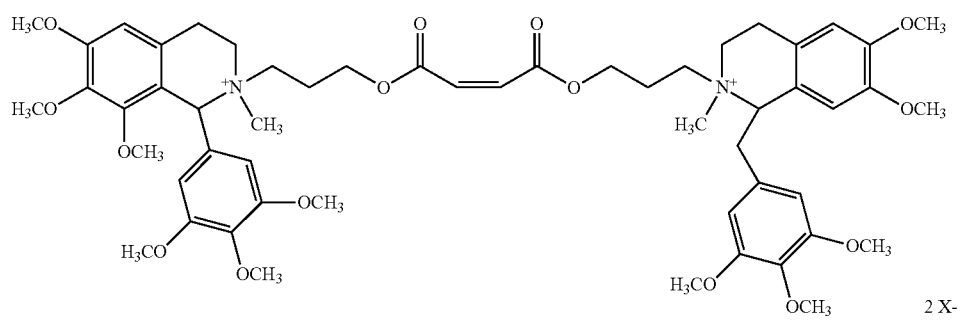
2 X−
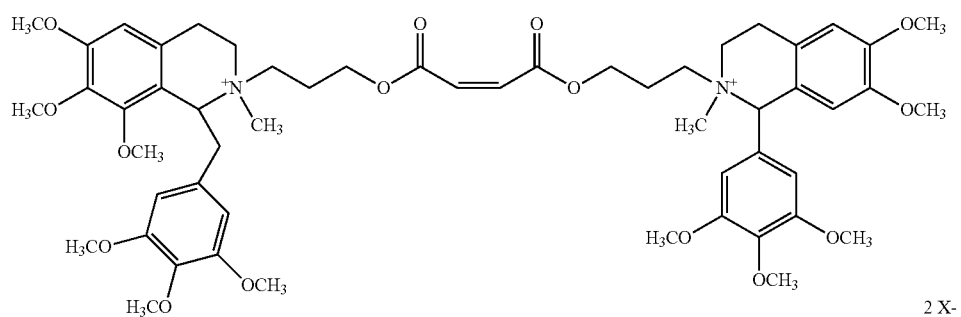
2 X−
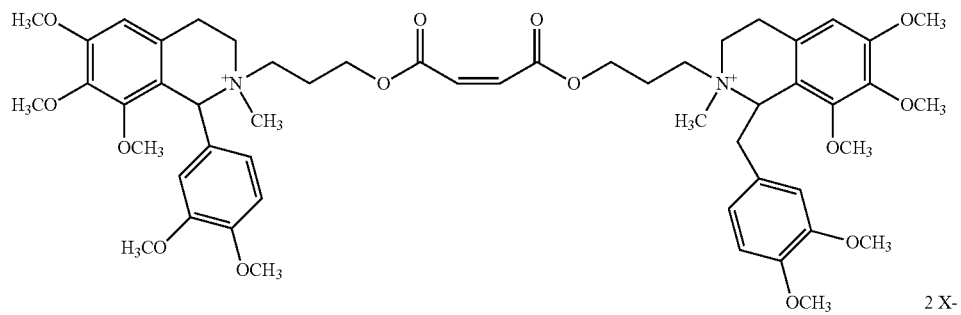
2 X−

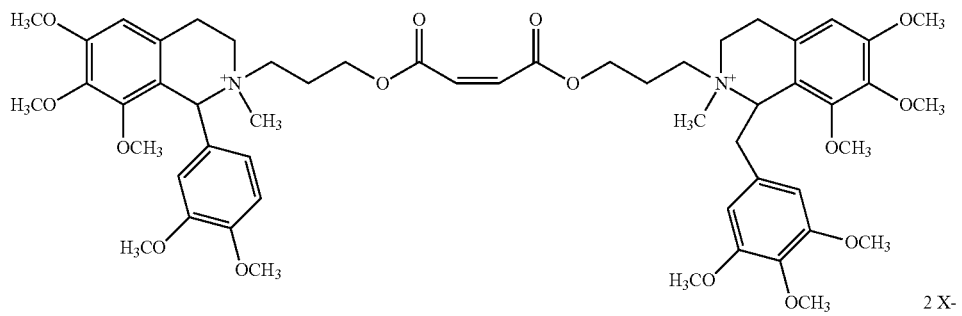
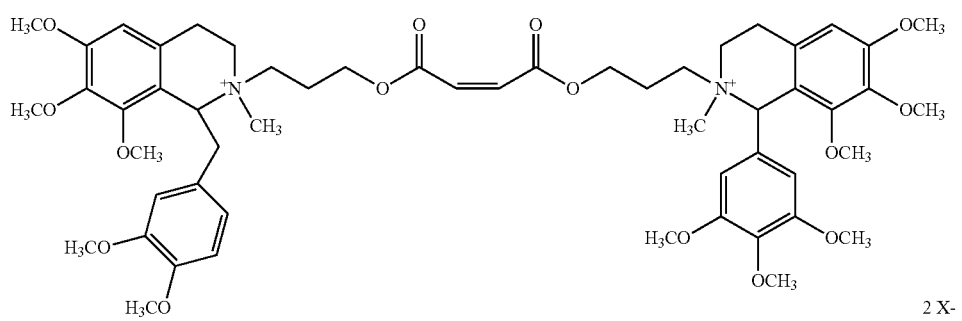
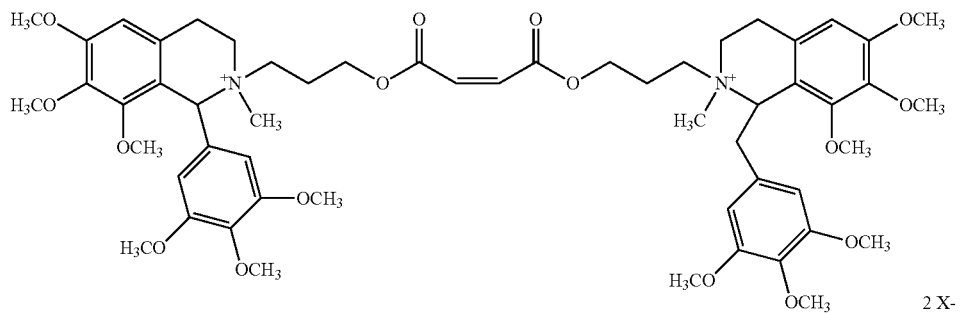
including any stereoisomer thereof, or any solvate, hydrate, metabolite, or prodrug thereof.
In various embodiments, the maleate compound can be any of the following:
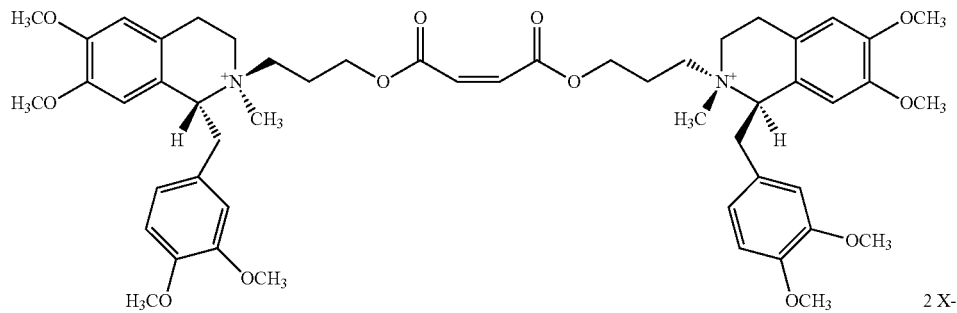
[NB 968-39]

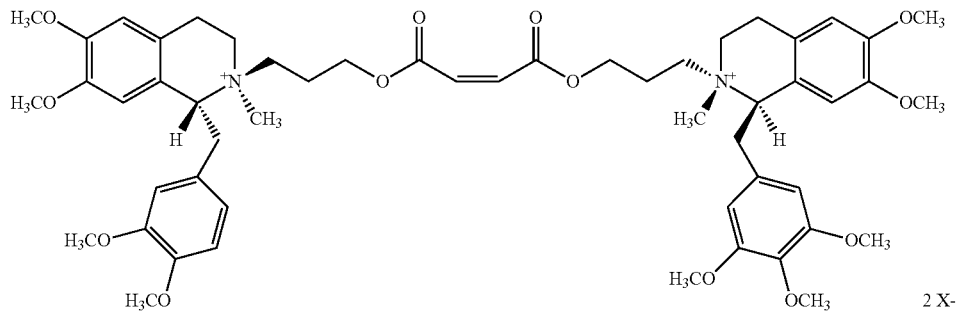
[NB 1043-46 (CW011)]
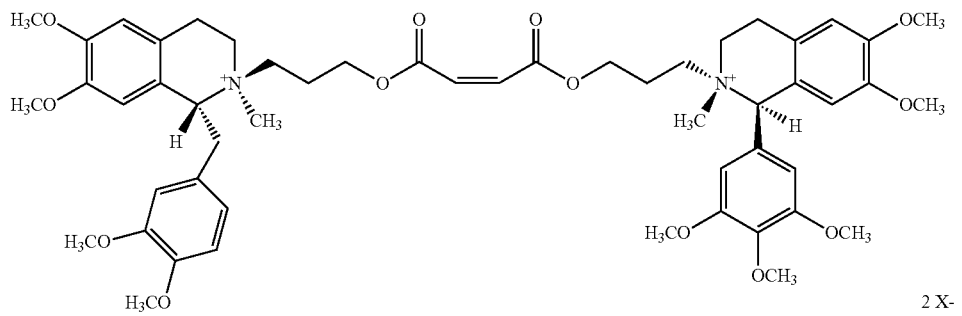
[NB 1064-81]
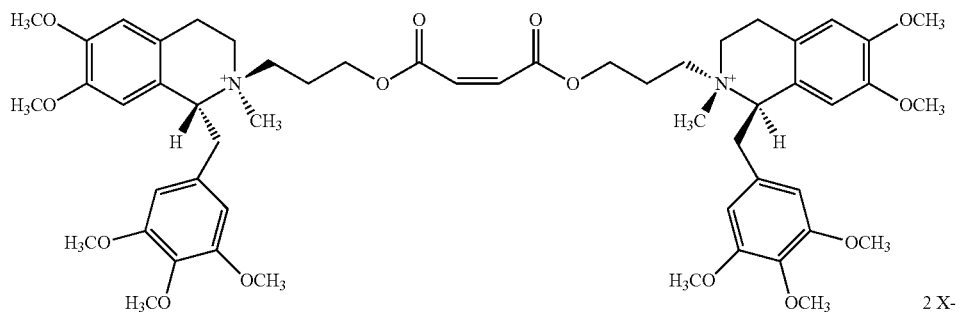
or any solvate, hydrate, metabolite, or prodrug thereof.
In various embodiments, a compound of the invention can be any of the following fumarates:
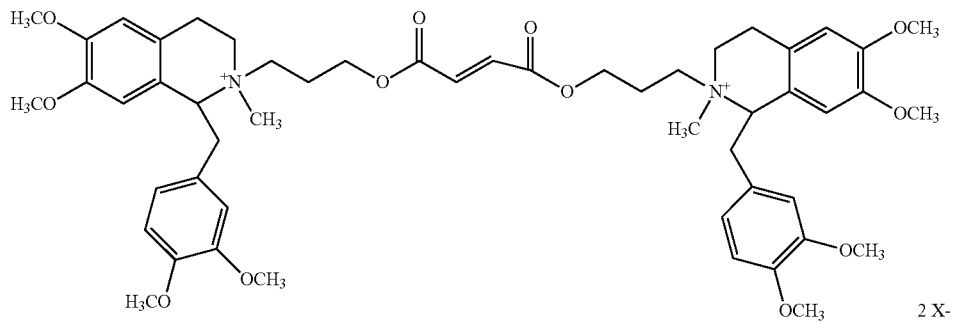
[R-trans, R-trans is NB 1025-68 (CW002), R-cis, R-cis is NB 832-65 (CW003)]

-continued
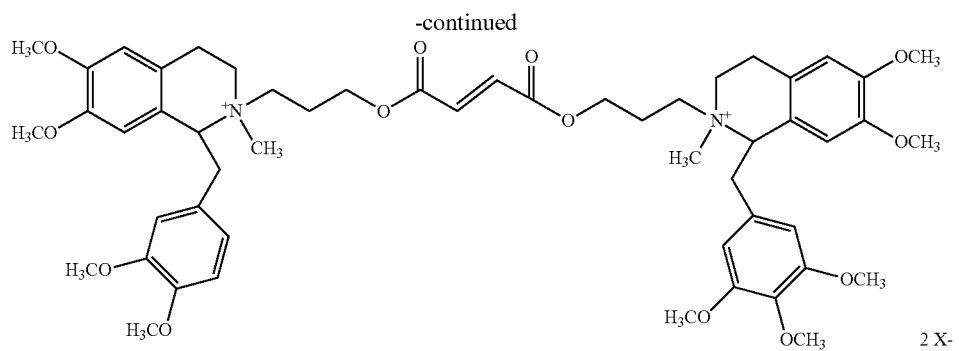
2 X⁻
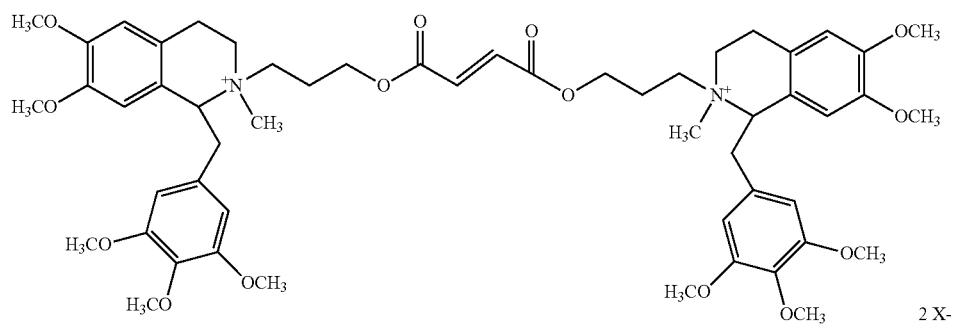
2 X⁻
[R-trans, R-trans is NB 802-17 (CW001)]
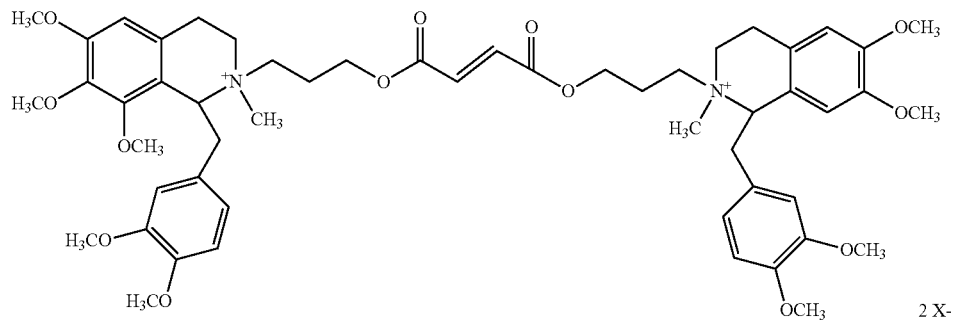
2 X⁻
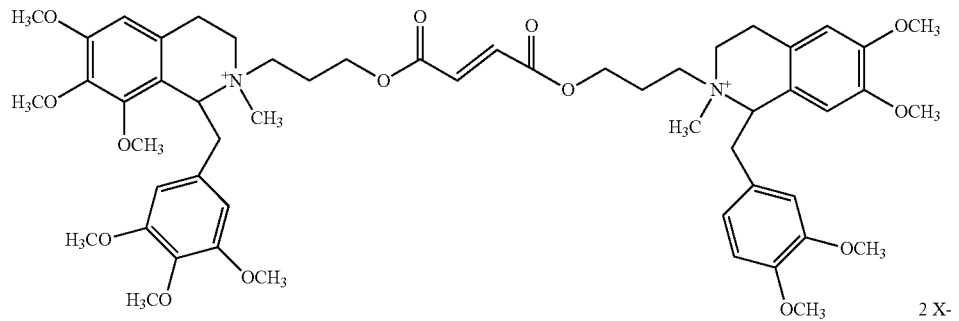
2 X⁻
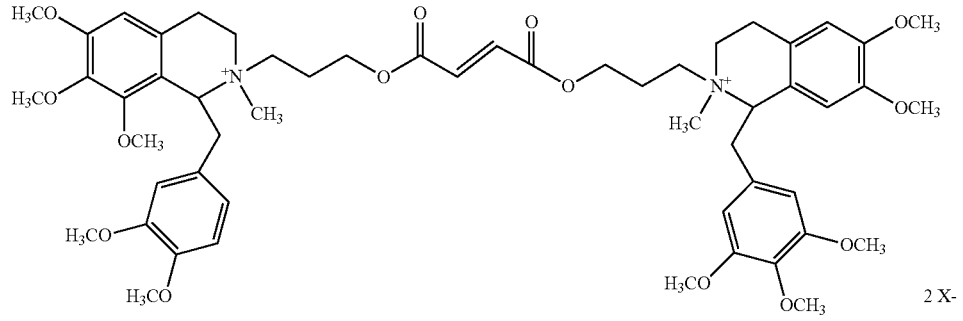
2 X⁻

-continued
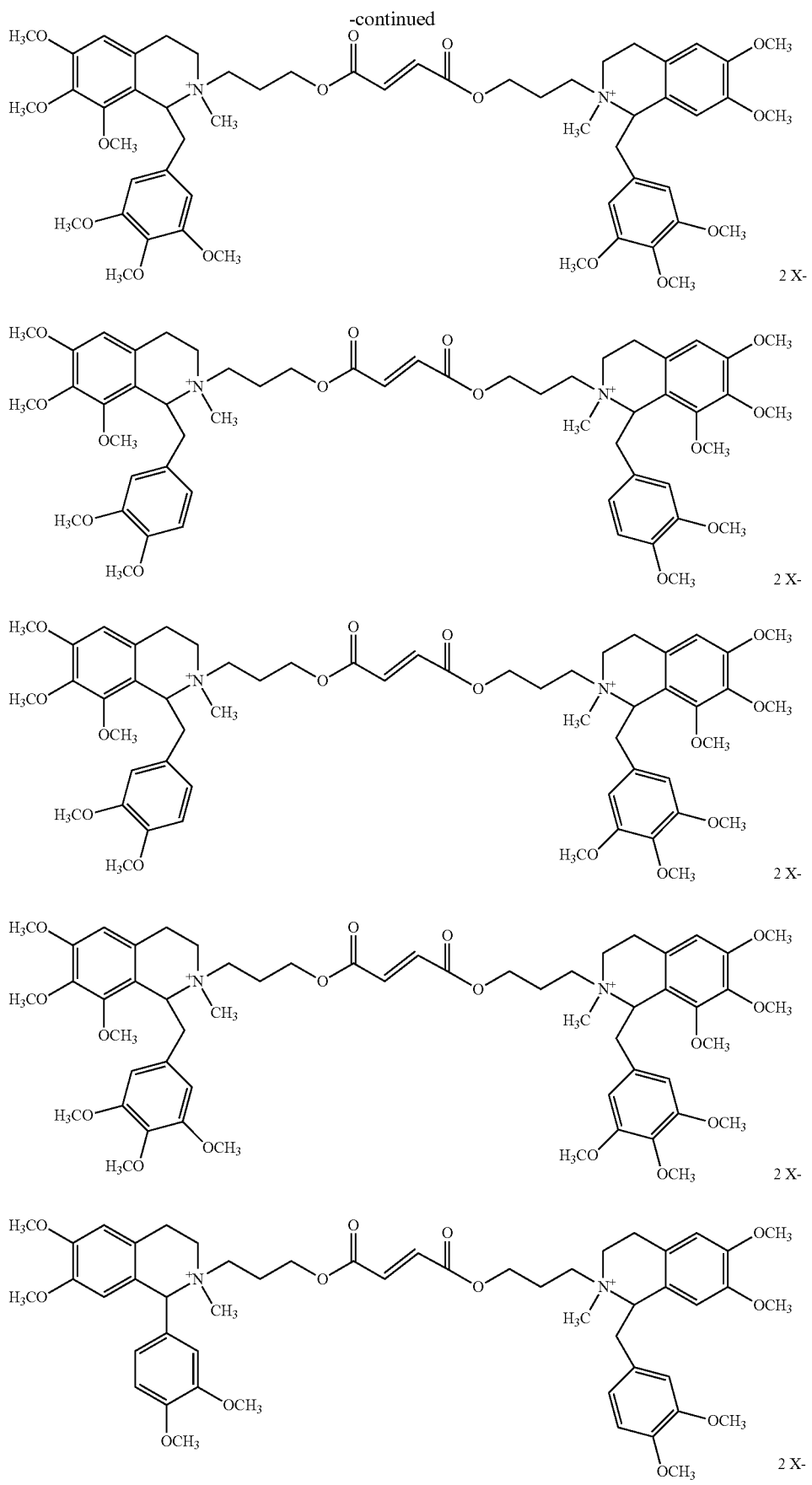

-continued
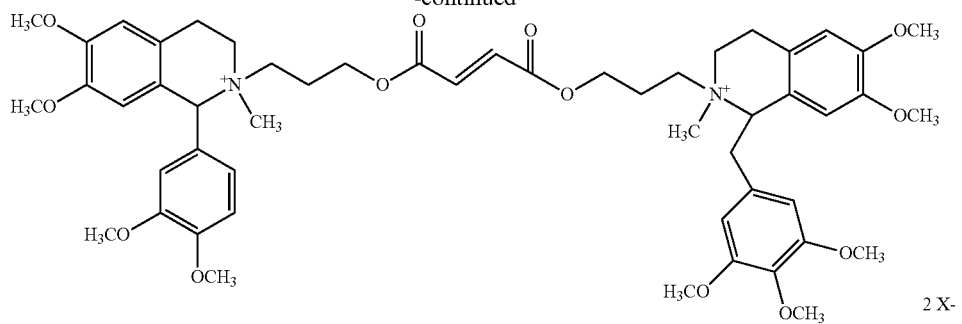
2 X-
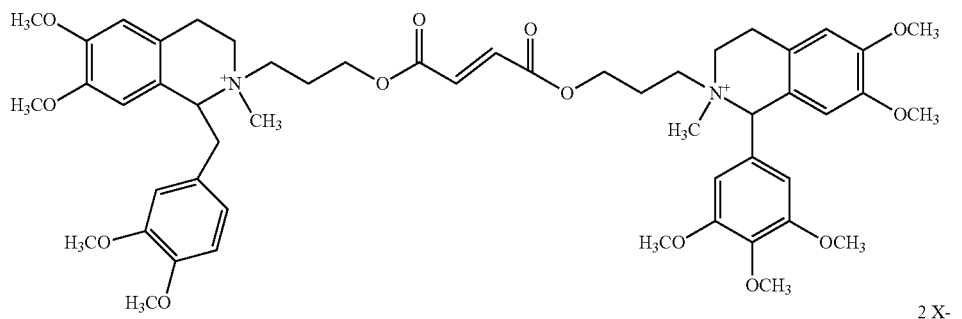
2 X-
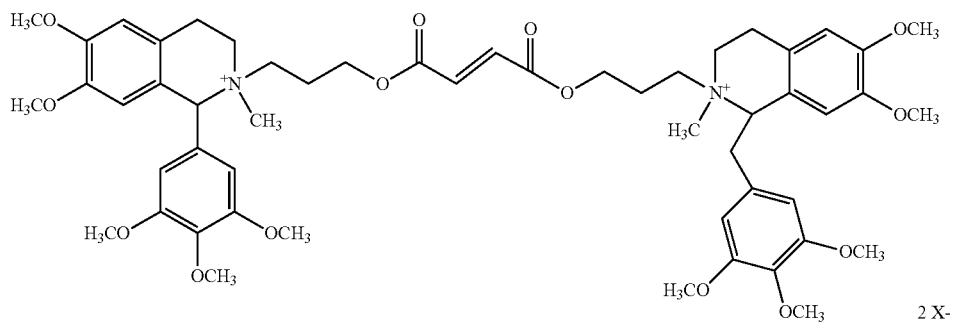
2 X-
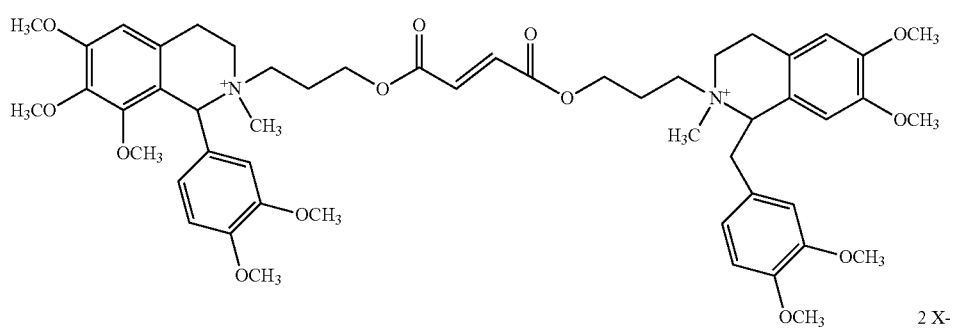
2 X-
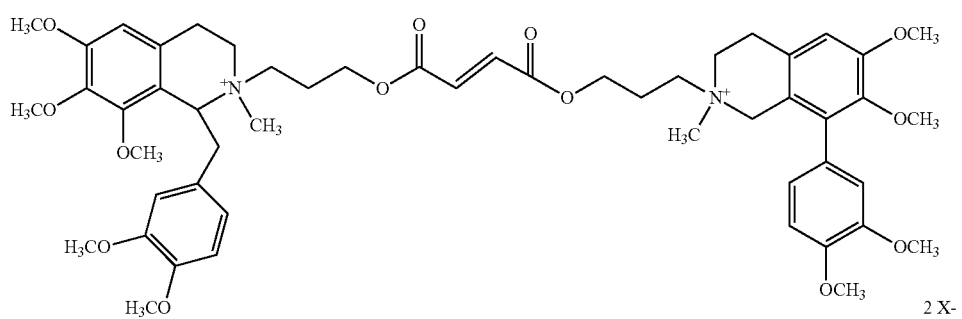
2 X-

-continued
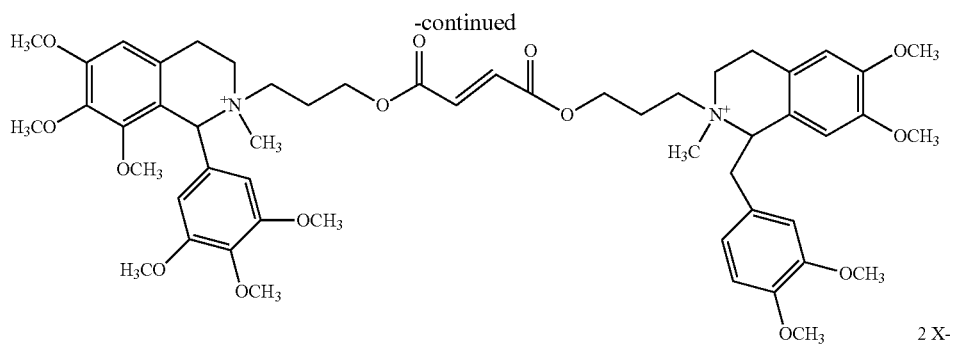
2 X-
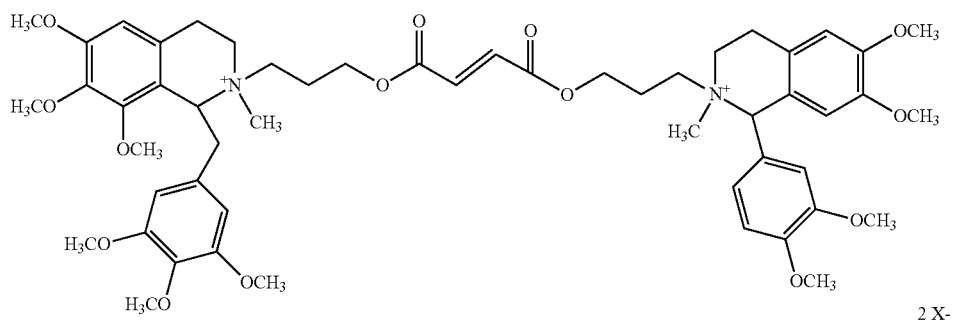
2 X-
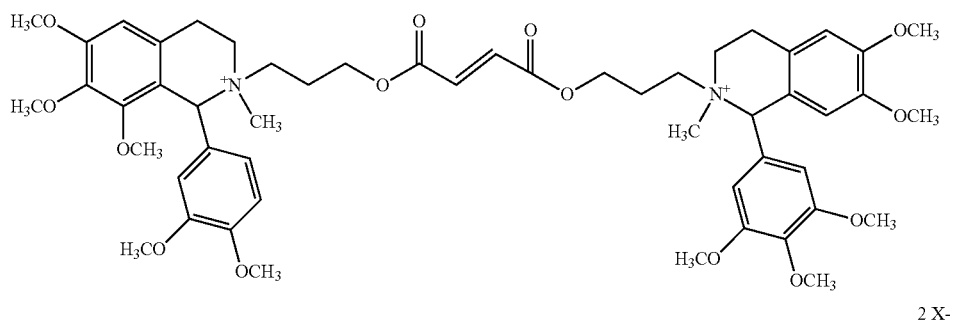
2 X-
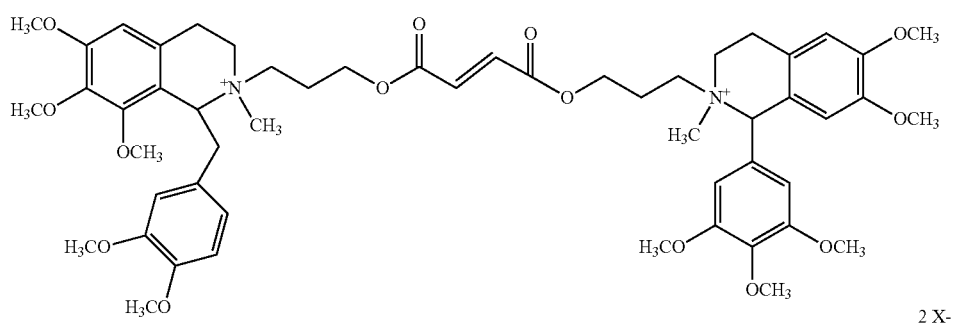
2 X-
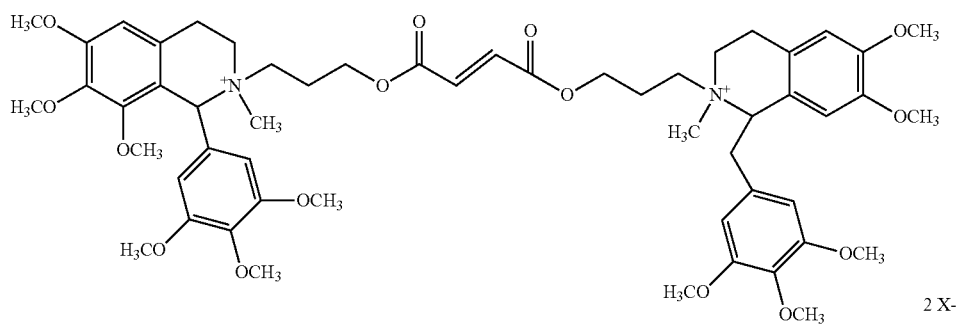
2 X-

-continued
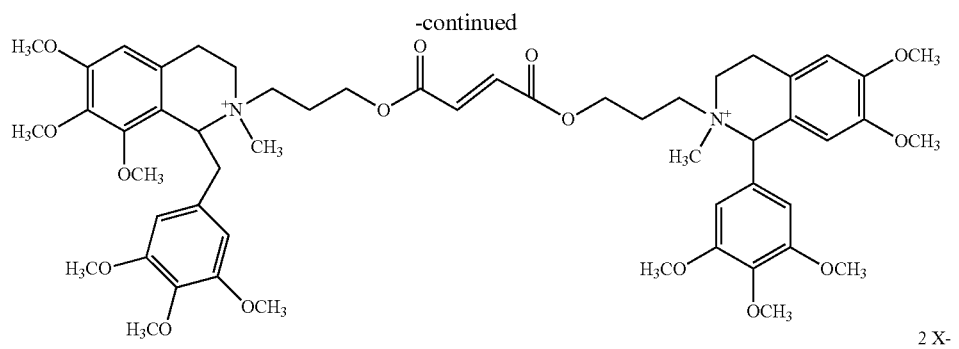
2 X-
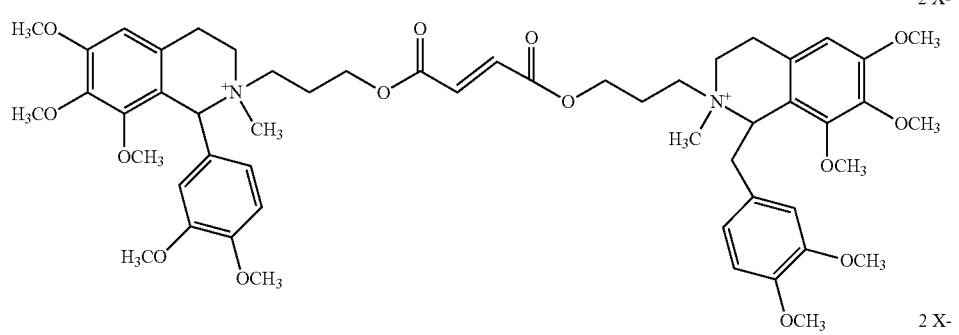
2 X-
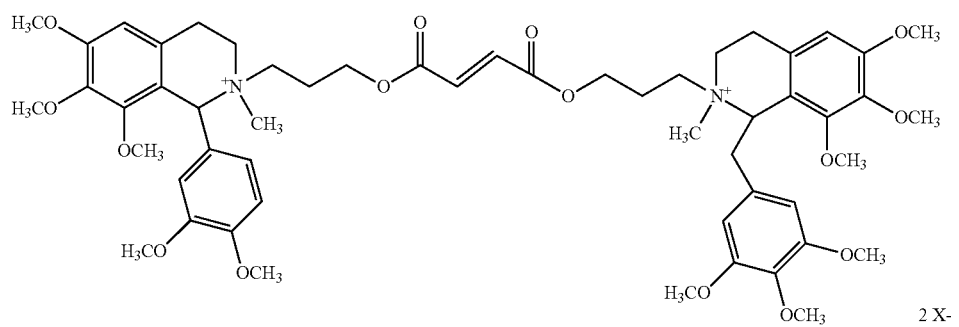
2 X-
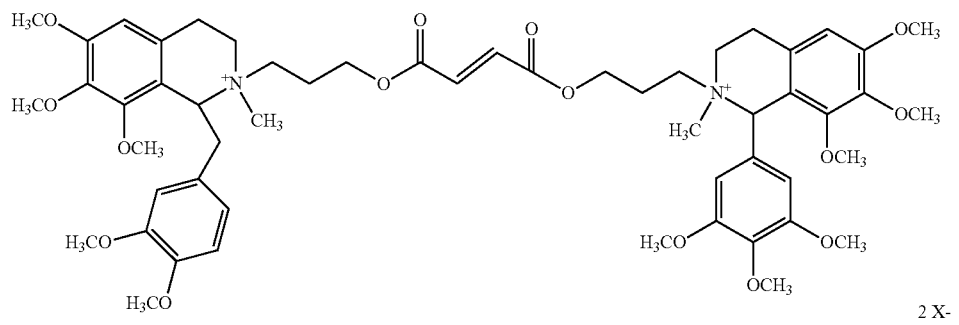
2 X-
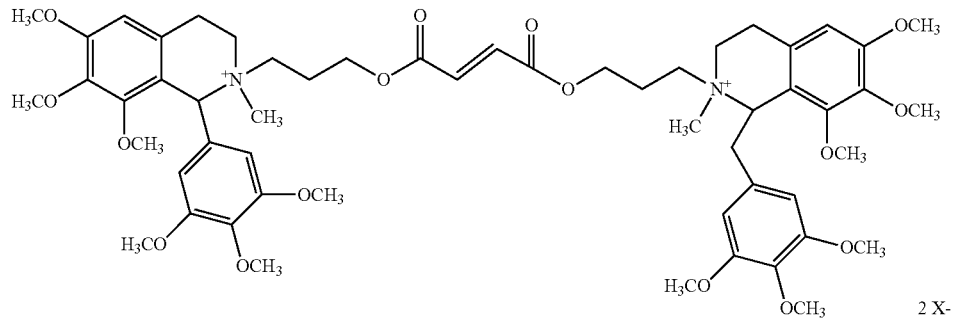
2 X- including any stereoisomer thereof, or any solvate, hydrate, metabolite, or prodrug thereof.
In various embodiments, the fumarate compound can be any of the following:
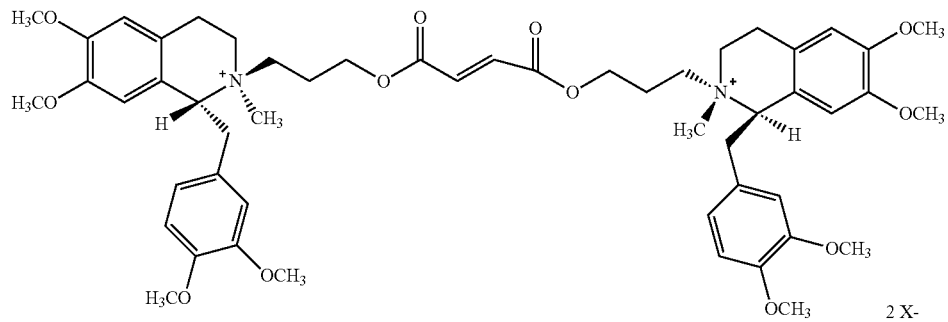
[NB 1025-68 (CW002)]
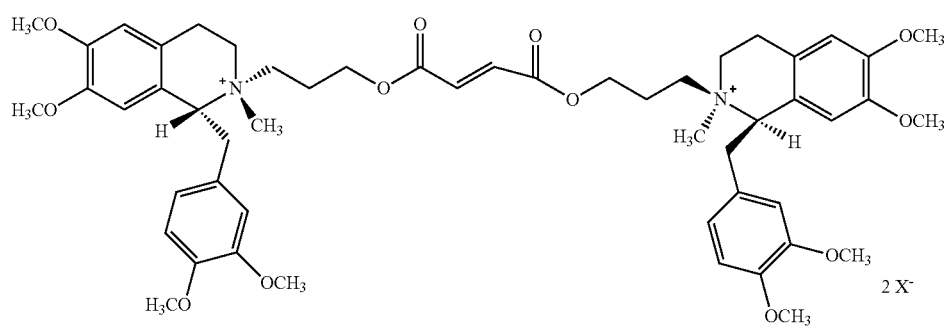
[NB 832-65 (CW003)]
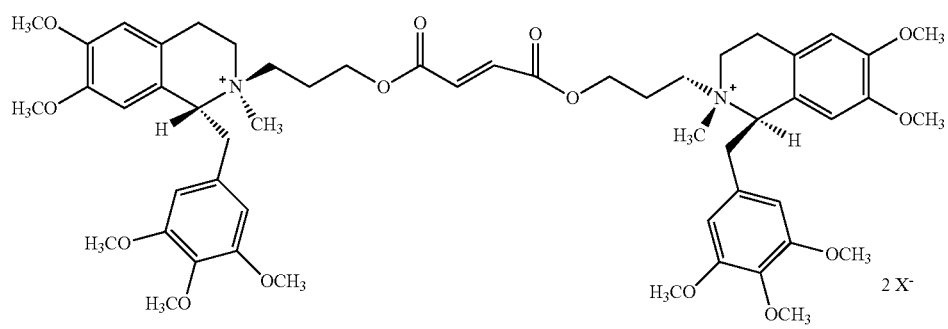
[NB 802-17 (CW001)]
or any solvate, hydrate, metabolite, or prodrug thereof.
In various embodiments, a compound of the invention can be any of the following succinates:

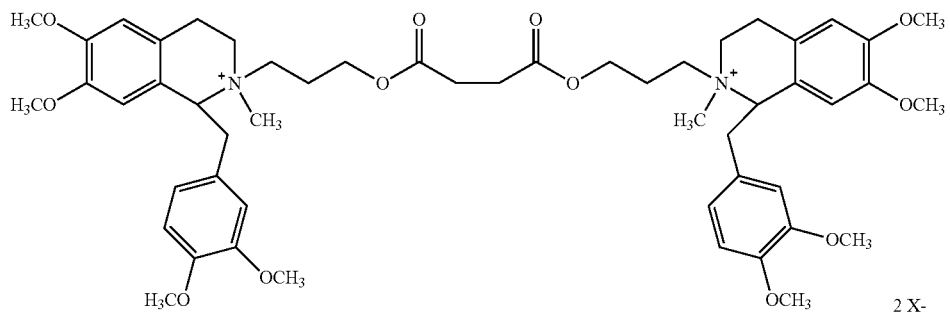
[R-trans, R-trans is NB 1163-79]
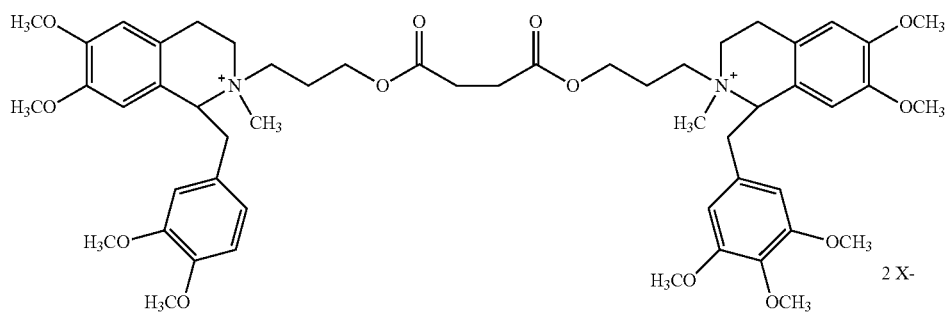
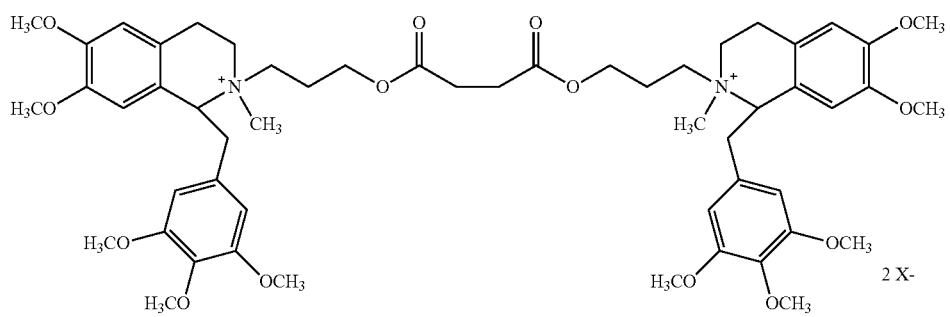
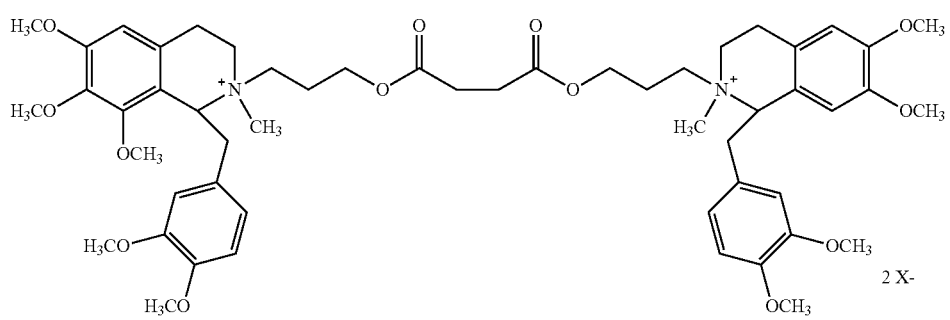
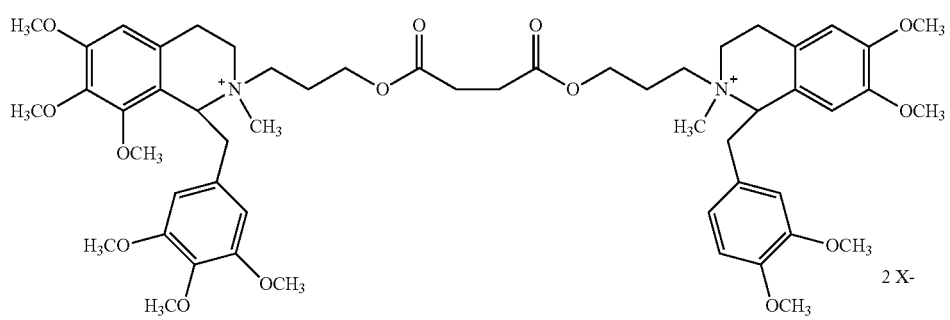

-continued
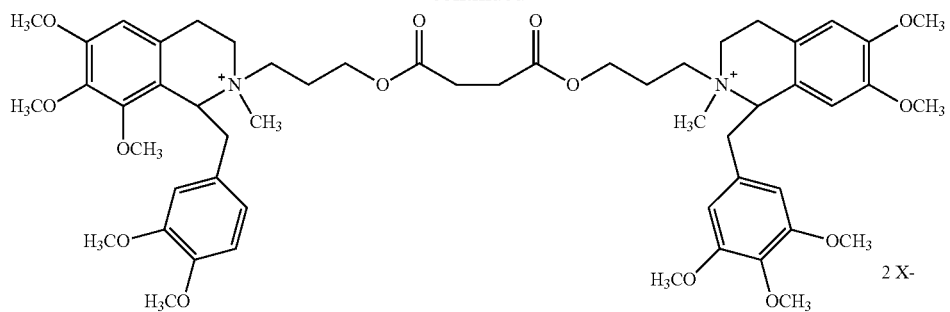
2 X-
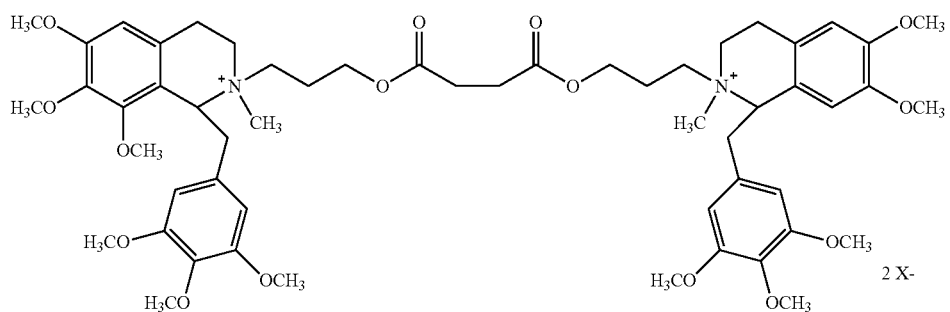
2 X-
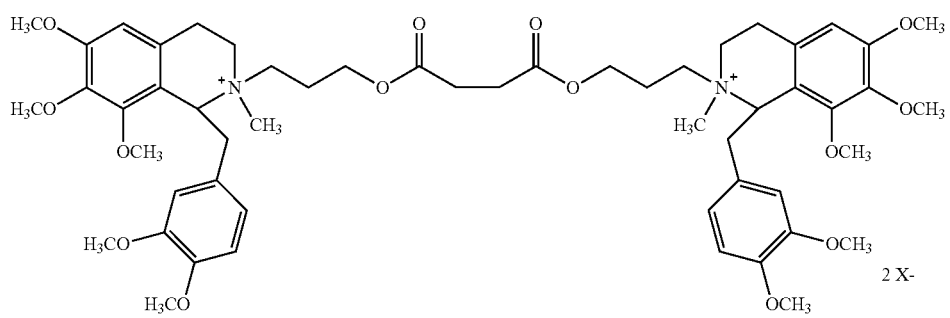
2 X-
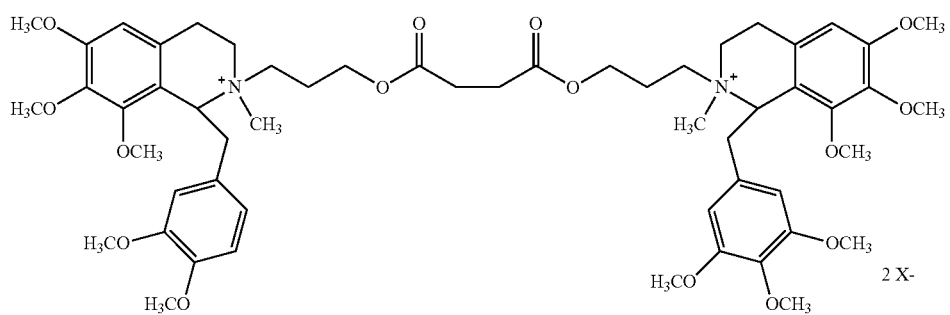
2 X-
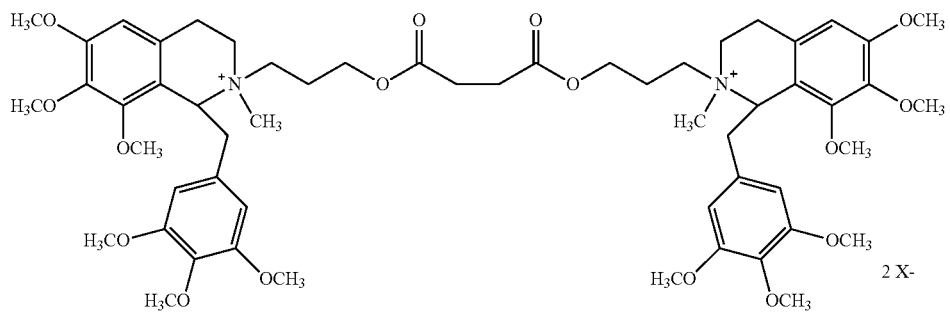
2 X-

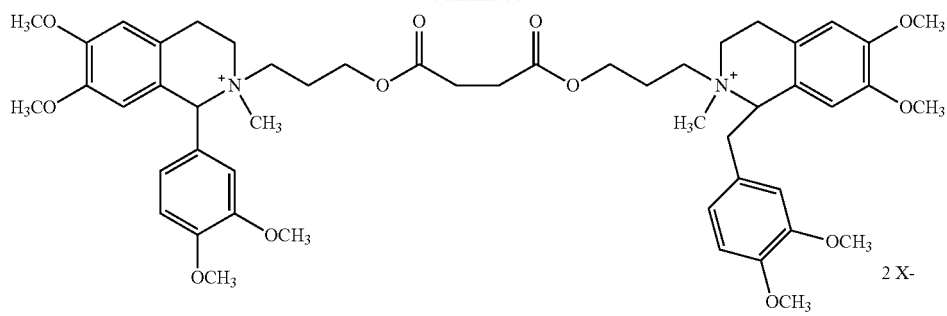
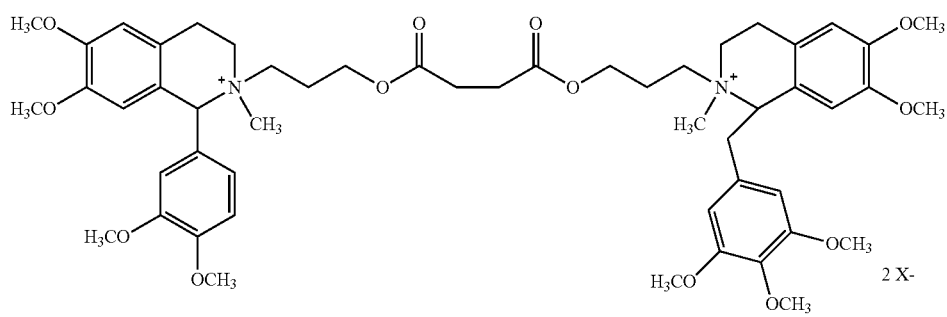
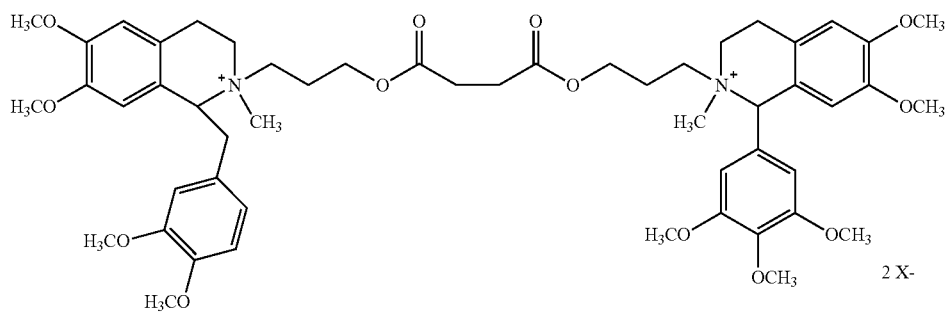
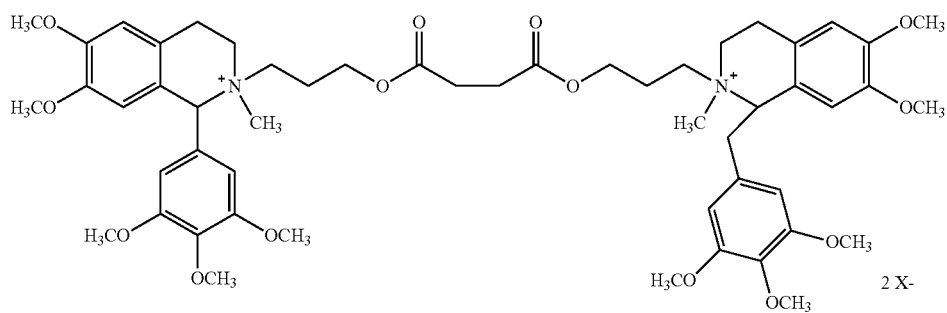
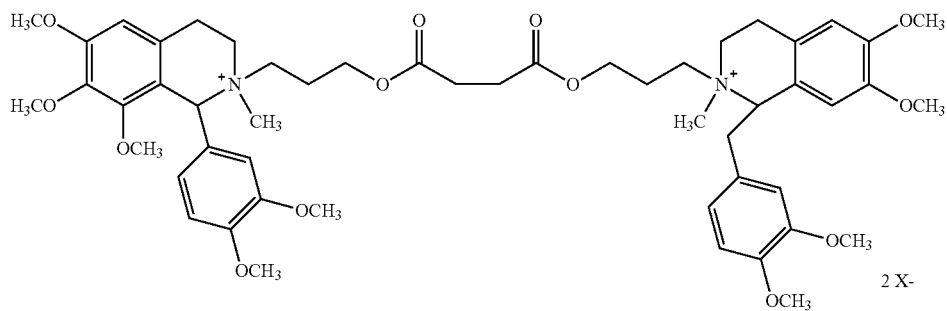

-continued
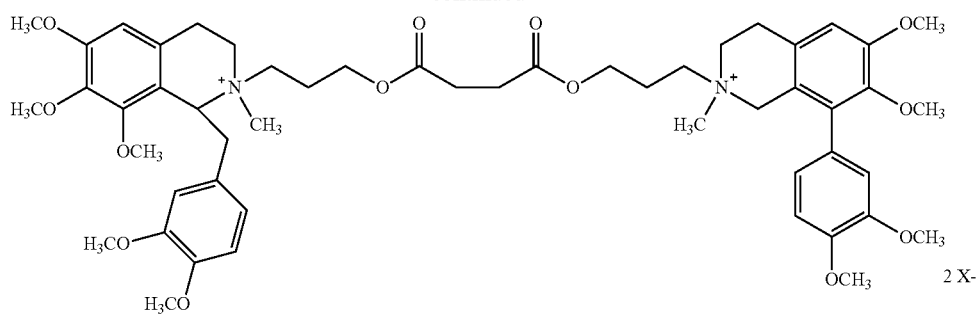
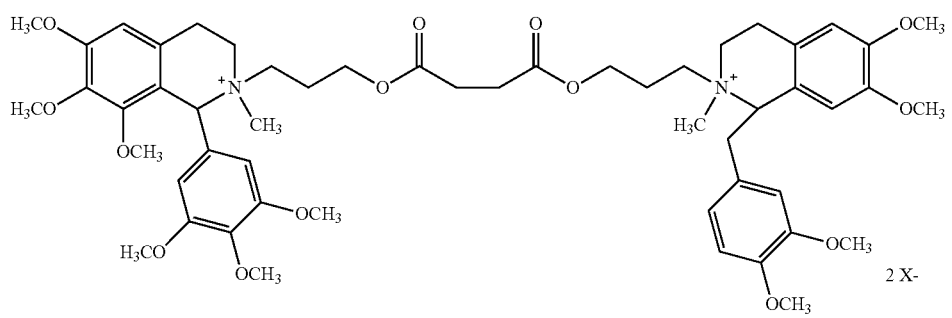
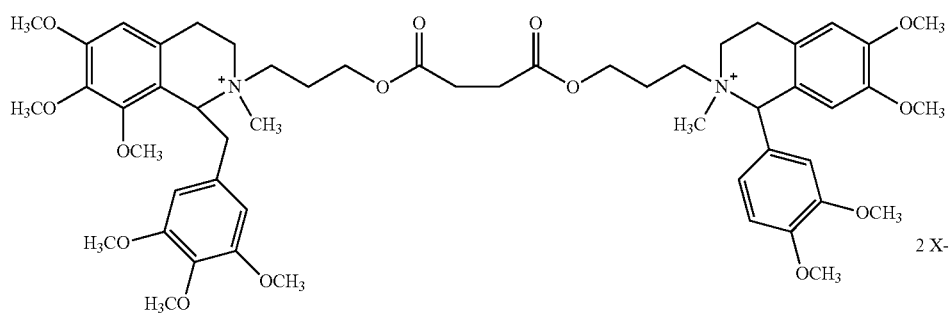
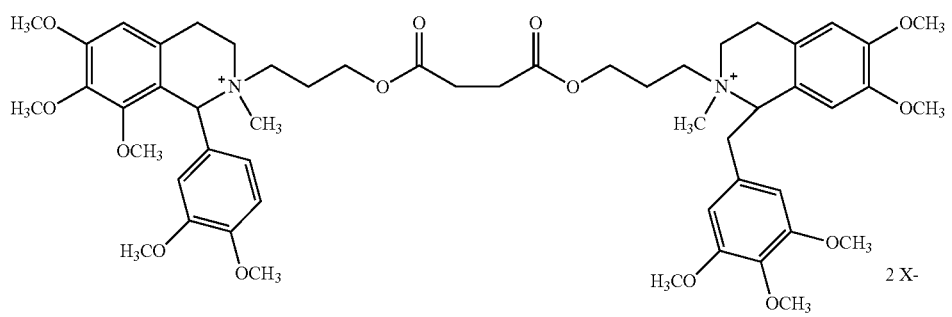
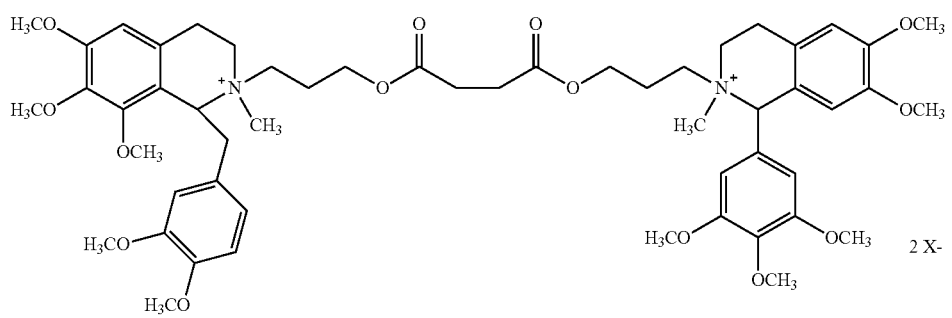

-continued
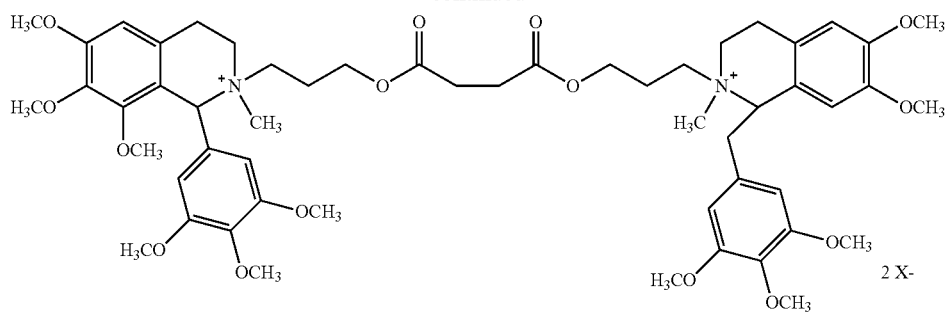
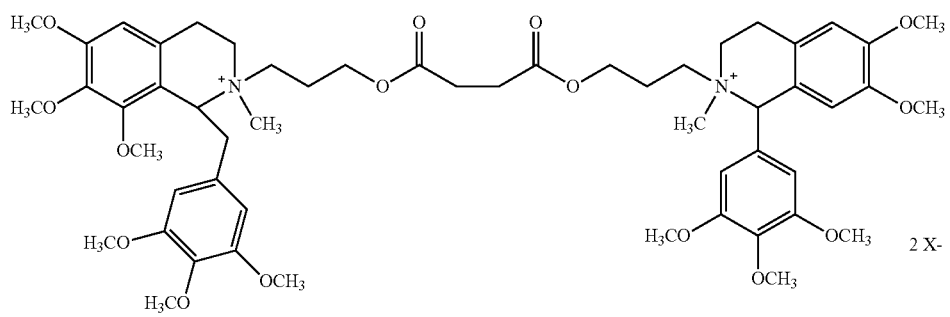
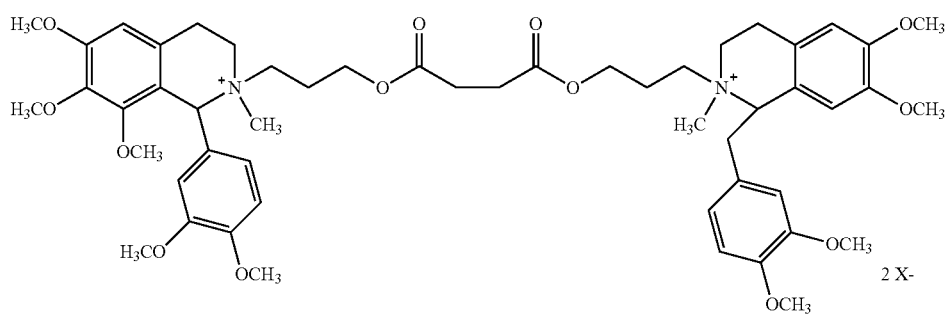
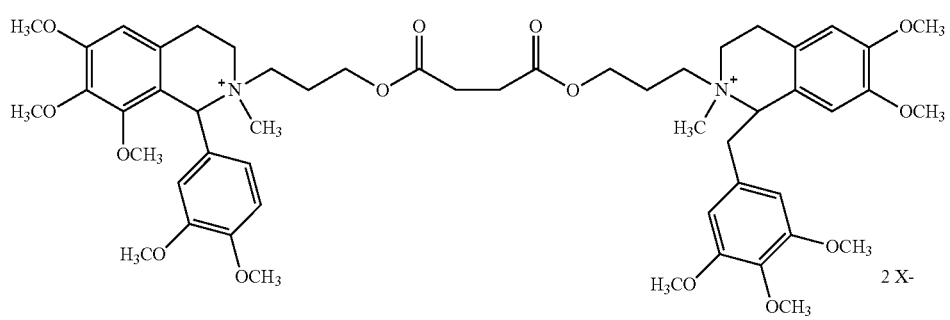
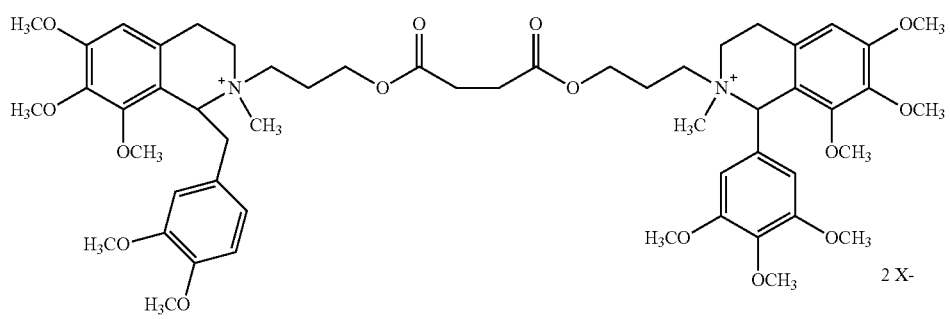

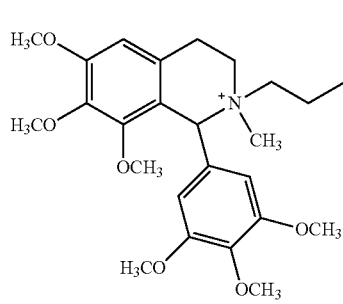
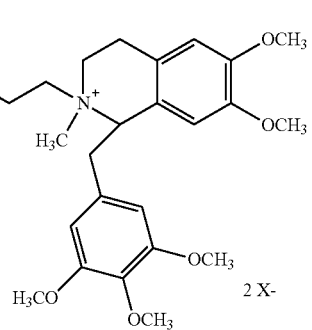
including any stereoisomer thereof, or any solvate, hydrate, metabolite, or prodrug thereof.
In various embodiments, a succinate compound of the invention can be any of the following:
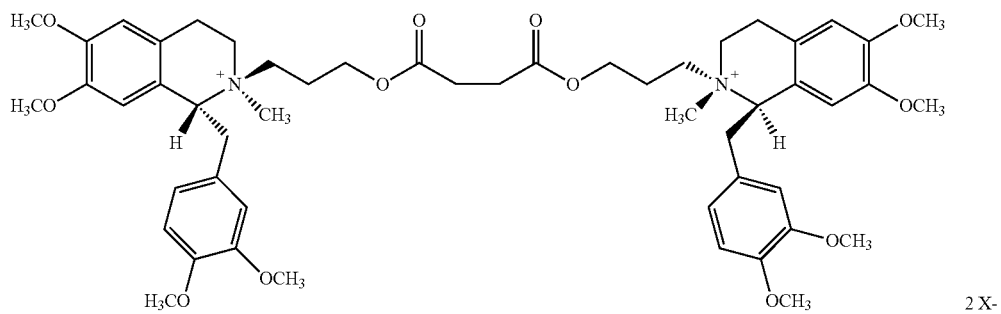
[NB 1163-79]
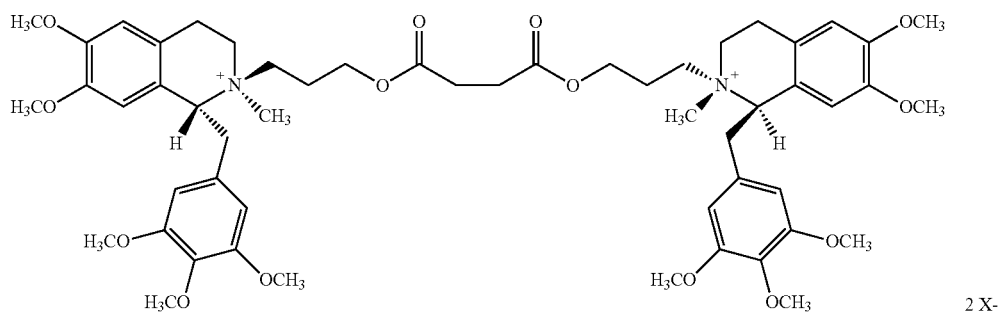
or any solvate, hydrate, or prodrug thereof.
In various embodiments, a compound of the invention can be any of the following acetylenedicarboxylates:
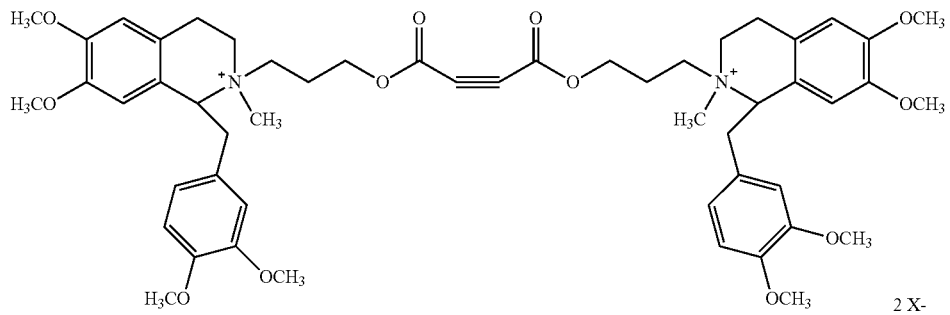

-continued
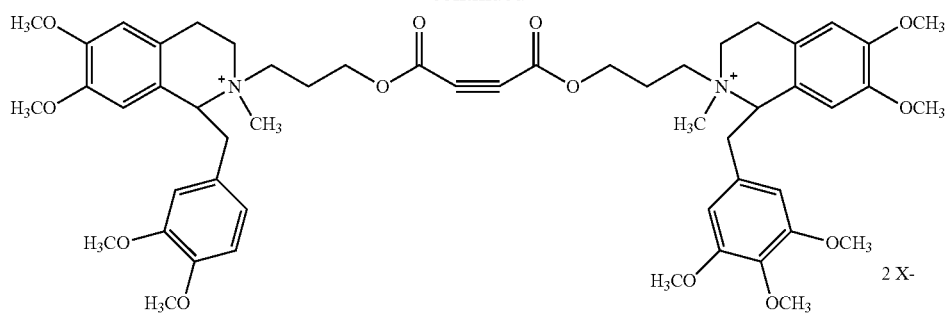
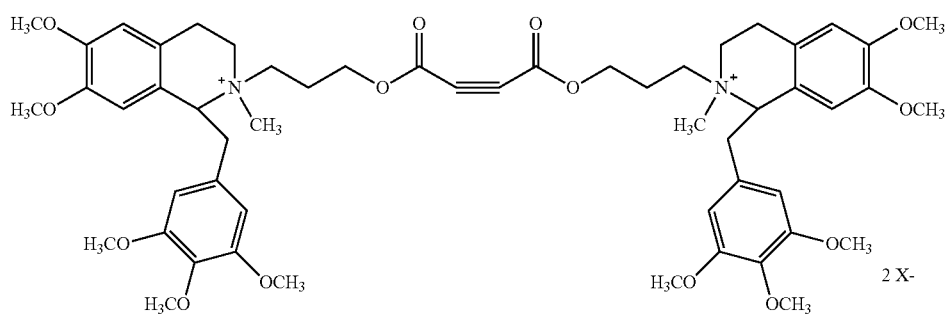
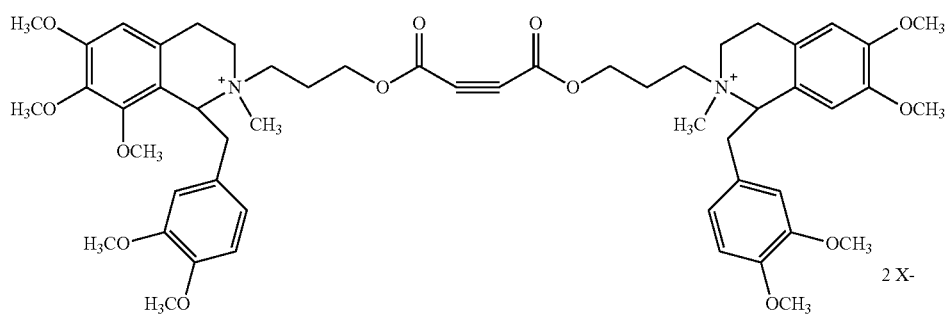
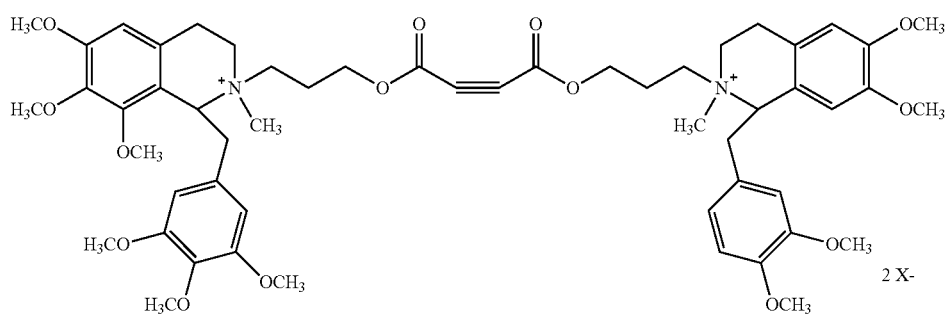
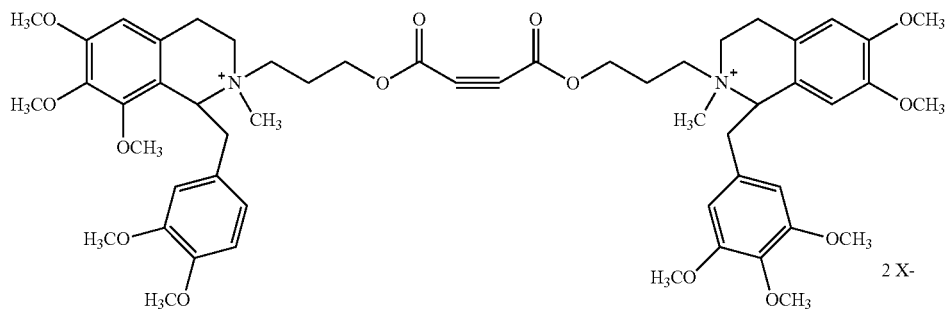

-continued
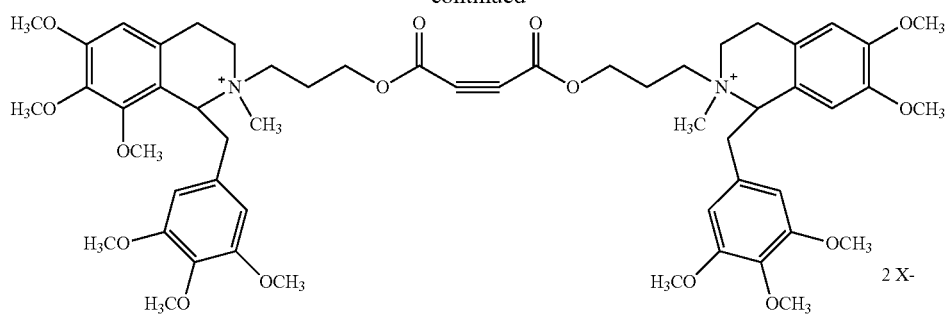
55
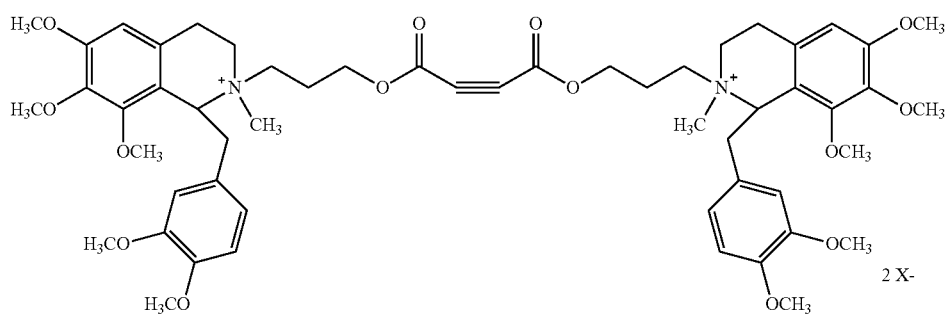
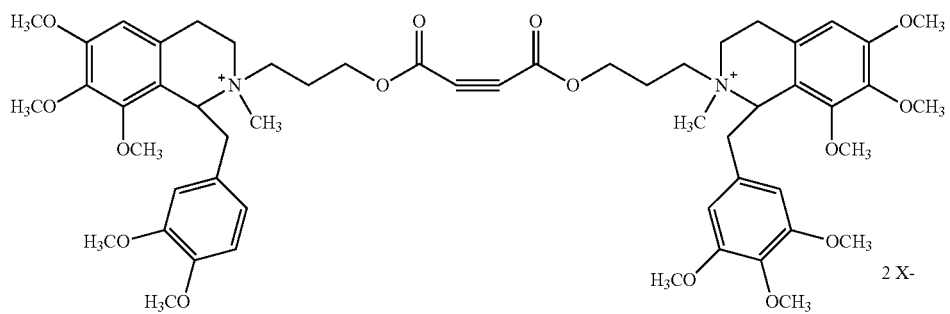
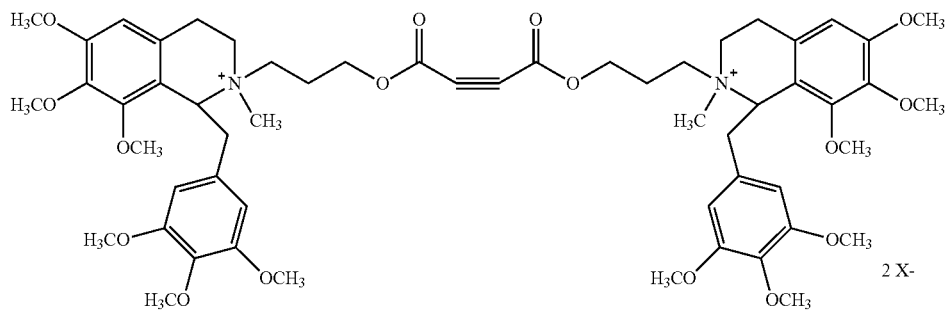
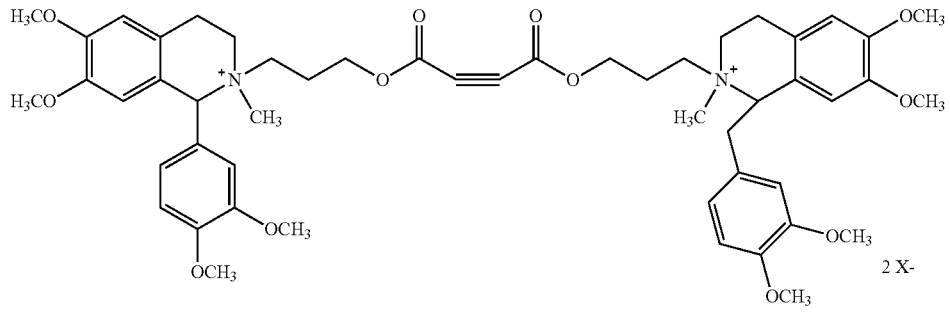

-continued
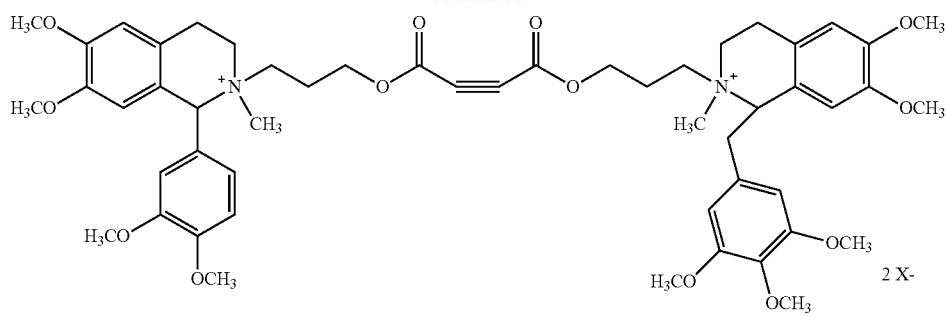
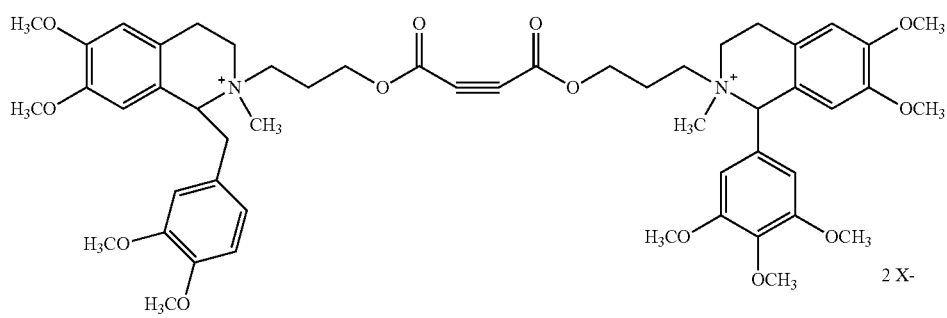
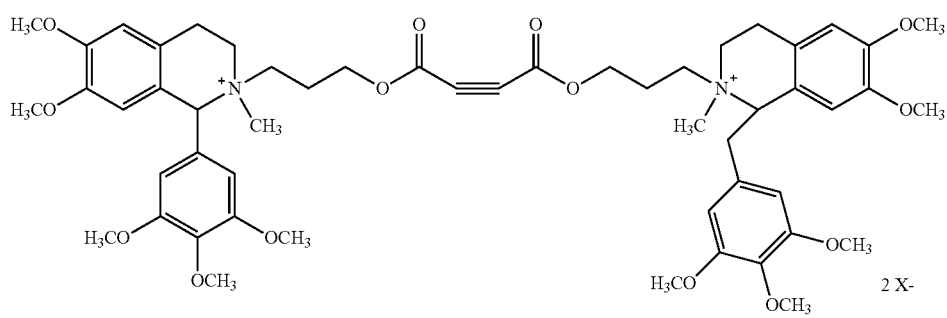
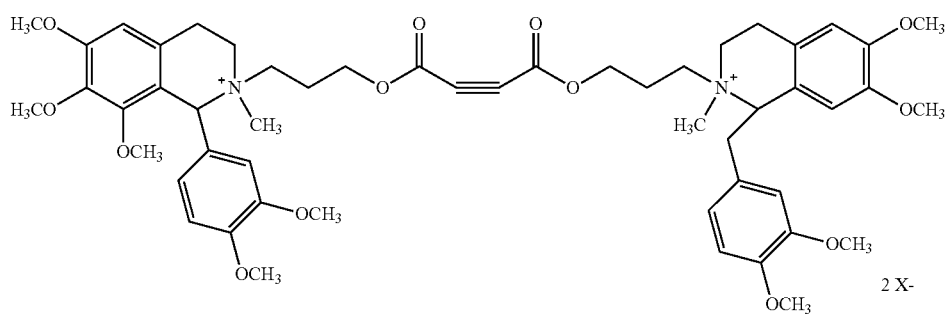
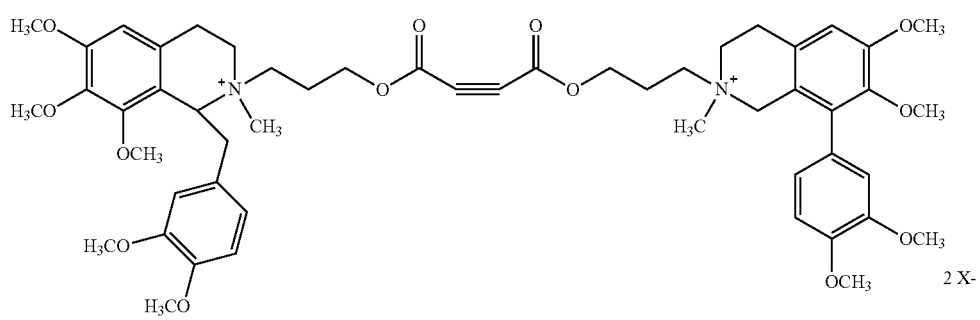

-continued
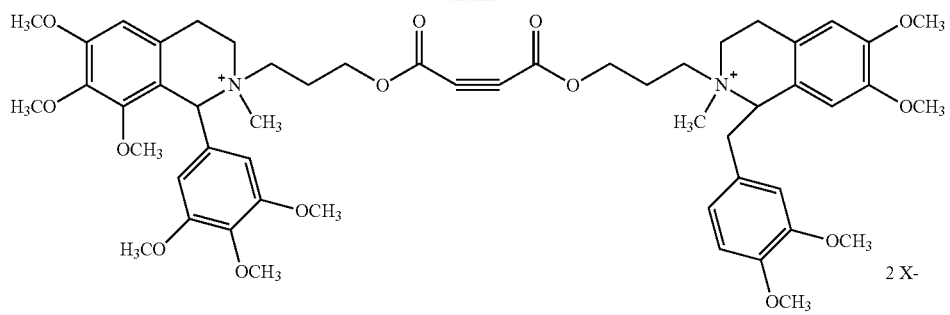
2 X-
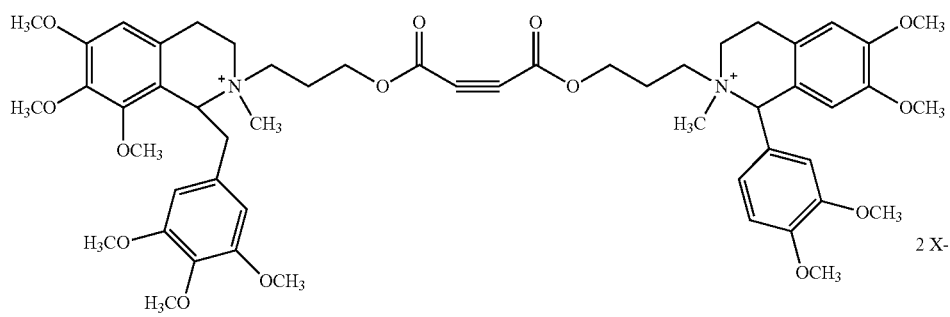
2 X-
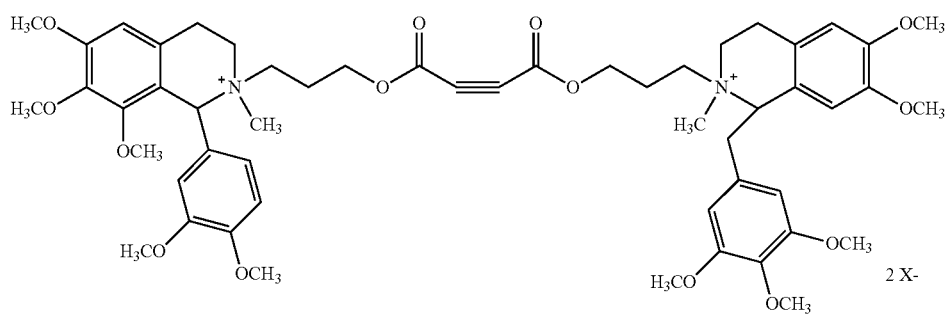
2 X-
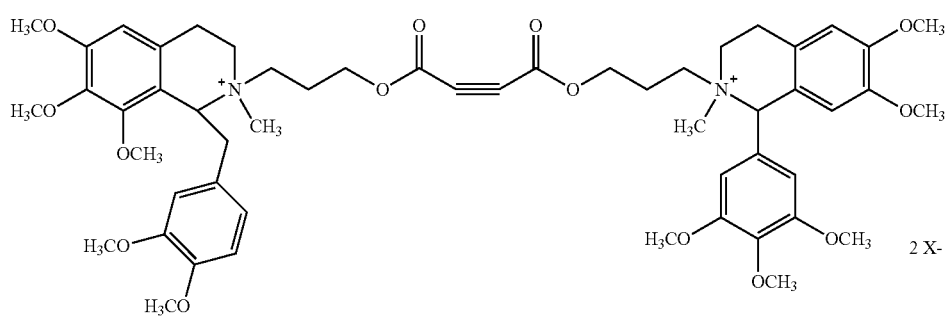
2 X-
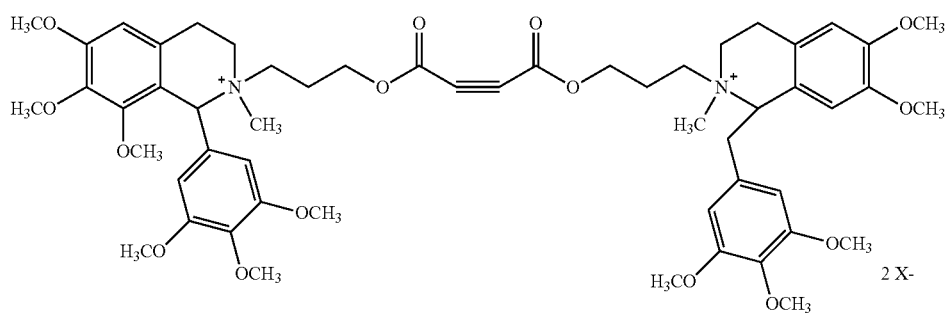
2 X-

-continued
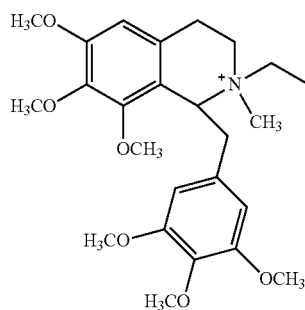 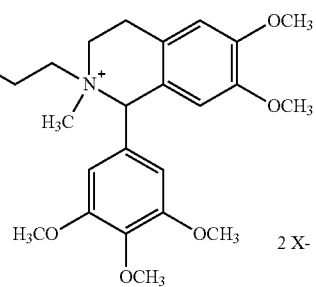
2 X−
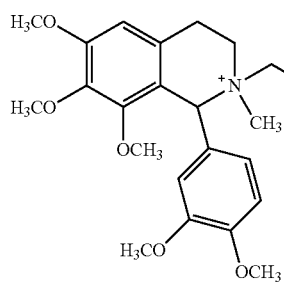 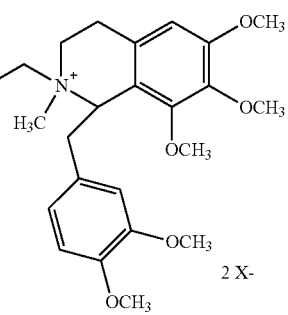
2 X−
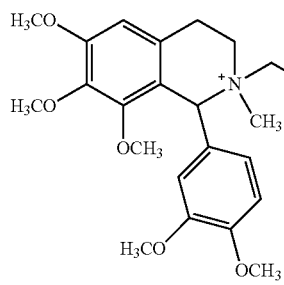 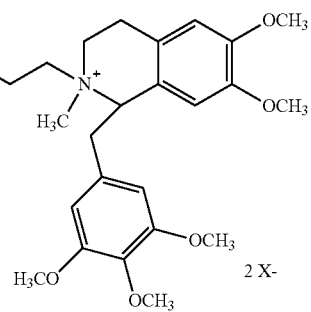
2 X−
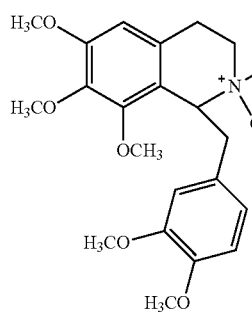 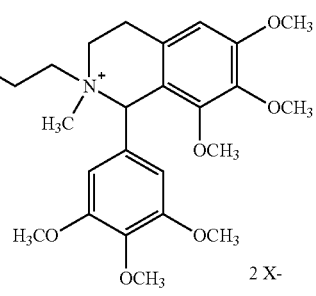
2 X−
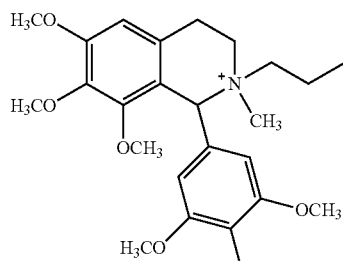 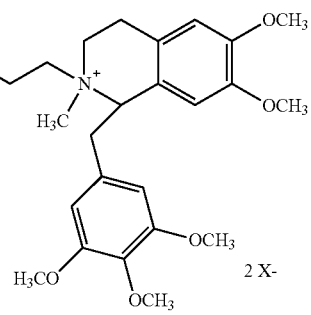
2 X− including all stereoisomers thereof, or any solvate, hydrate, or prodrug thereof.

In various embodiments, an acetylenedicarboxylate of the invention can be any of the following:

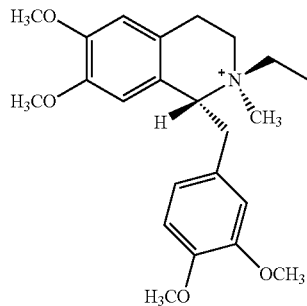 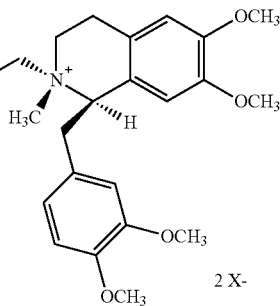

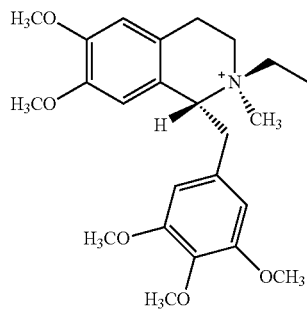 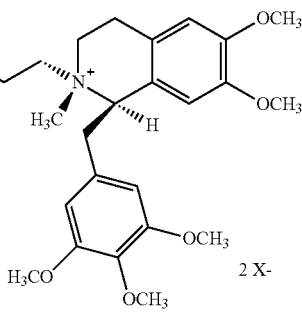

or any solvate, hydrate, or prodrug thereof.

Synthesis of Compounds of the Invention

Compounds of the invention can be prepared according to the methods described herein, including in the Examples, combined with the skill and knowledge of the ordinary practitioner of synthetic organic chemistry.

Generally speaking, diesters of dibasic acids such as maleic, fumaric, succinic, and acetylenedicarboxylic acids can be prepared by formation of esters of both carboxylic acids, either concurrently or sequentially, with alcohols. The two esters can comprise either the same alcohol moiety, or differing alcohol moieties. In the present application, a diester is termed "symmetric" or "symmetrical" when both alcohol moieties are identical, and "asymmetric" or "asymmetrical" when the two alcohol moieties are not identical.

Condensation of a diacid with an alcohol can be carried out using substantially any of the carboxyl activation procedures known in the art. When the dicarboxylic acid can cyclize to form a cyclic anhydride, as in the case of maleic and succinic acids, a cyclic anhydride can be used. In all cases, activated carboxyl groups such as acyl chlorides and activated esters (e.g., N-hydroxysuccinimide esters, N-hydroxybenztriazole esters, and the like) can be used. When a cyclic anhydride is used as the activated carboxyl species, only one mole of alcohol can react in that step, providing a diacid-monoester species. This intermediate can be activated and condensed with a second mole of an alcohol, the same or different, to provide a diester. For example, see Synthetic Scheme 1, below. This approach can be used to prepare both symmetric and asymmetric diesters for those diacids having sterically accessible cyclic anhydride forms.

Condensation of maleic or succinic cyclic anhydride (XI), wherein a dotted bond indicates an optional single or double bond, with a first isoquinolylalkanol (XII) yields monoester (XIII). The free carboxyl group of monoester (XIII) can be activated by means known in the art, such as by formation of an activated ester, e.g., with N-hydroxysuccinimide/dicyclohexylcarbodiimide, to provide activated ester (XIV) wherein A represents a carboxyl activating moiety, which is then condensed with a second isoquinolylalkanol (XV) which can be the same as or different from isoquinolylalkanol (XII) to provide a symmetric or asymmetric compound of formula (I).

Synthetic Scheme 1: Reaction of cyclic anhydrides with isoquinolylalkanol
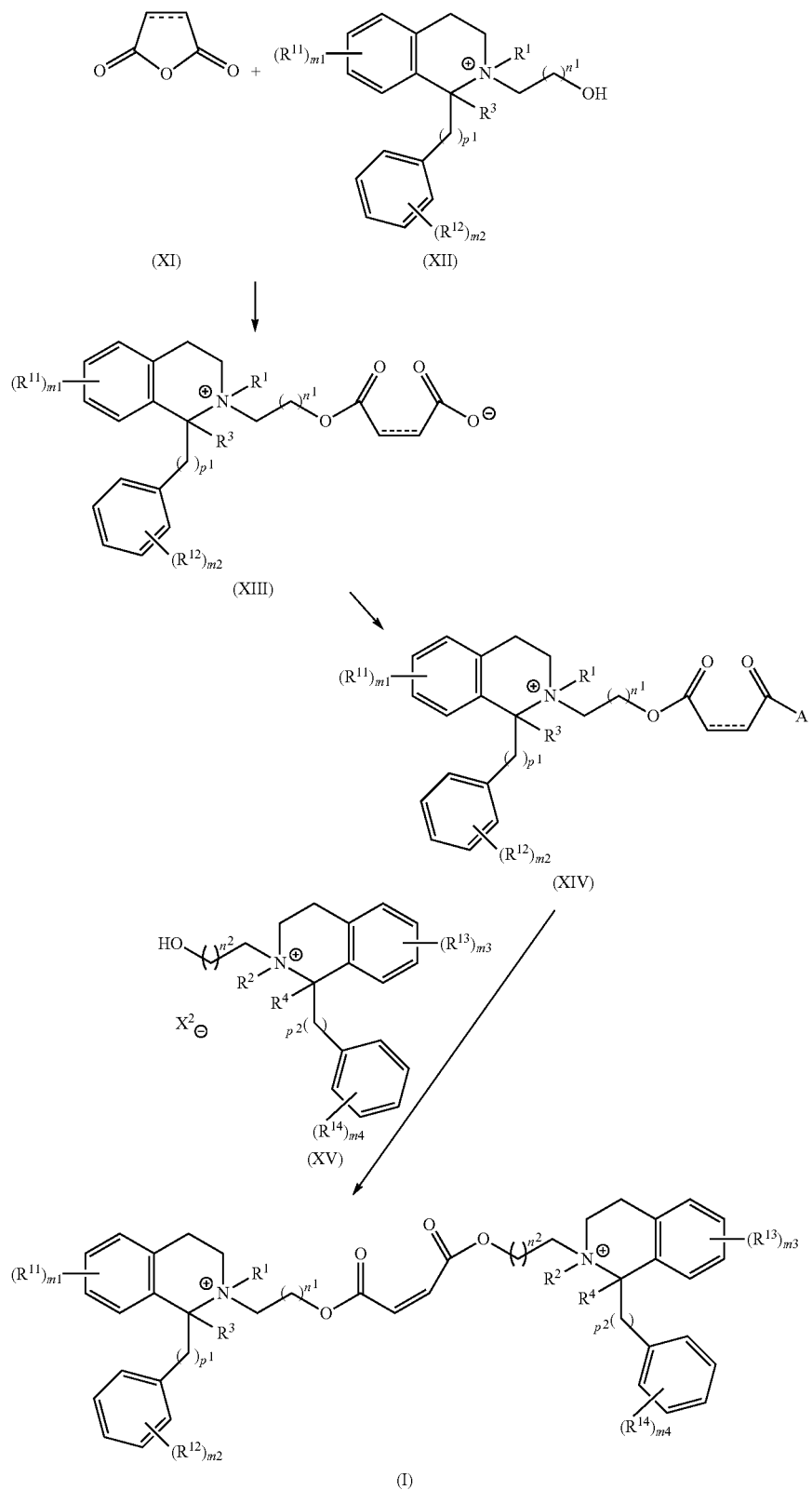
Whether or not a cyclic anhydride form is sterically accessible to a diacid, carboxyl activation procedures and intermediates that do not involve formation of a ring can be used. For example, for all of maleic, fumaric, succinic, and acetylenedicarboxylic acids, formula (XXI) wherein the dotted lines indicate a single bond, Z or E double bond, or a triple bond, formation of bis acyl halides (e.g., bis acyl chlorides) can be employed to provide a reactive intermediate. Similarly formation of activated esters can be used to provide a reactive intermediate. If a symmetrical diester is desired, an activated diacid can be condensed with an excess of the alcoholic reagent to provide a diester incorporating two moles of the alcohol moiety. For example, see Synthetic Scheme 2, below.

acetylenedicarboxylic acid, is condensed with an isoquinolylalkanol, preferably at least two molar equivalents thereof, to provide a symmetric compound of formula (I) of the invention. As described above, carboxyl activation can employ any of the many methods well known in the art. The use of less than two equivalents of the isoquinolylalkanol (XXII) will result in formation of significant quantities of the corresponding monoester, which can be separated and used in a second esterification step, using a different isoquinolylalkanol if desired, to prepare an asymmetric compound of formula (I).

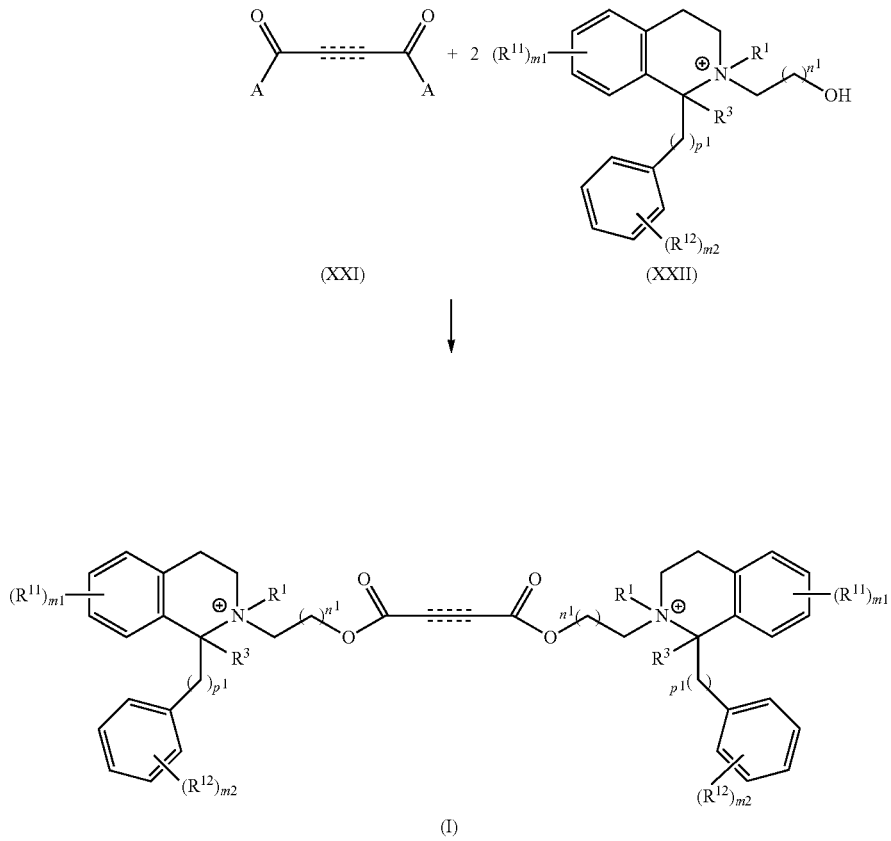

A carboxyl-activated diacid (XXI), which can be a bis-carboxyl-activated form of maleic, fumaric, succinic, or

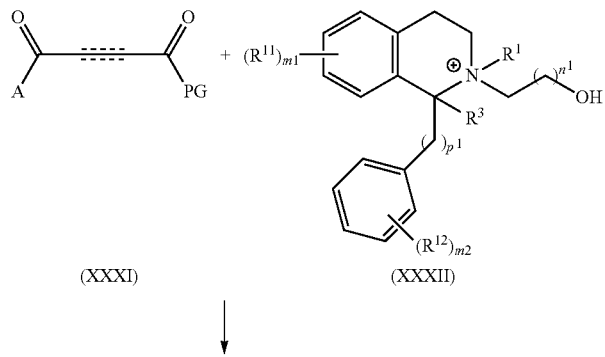

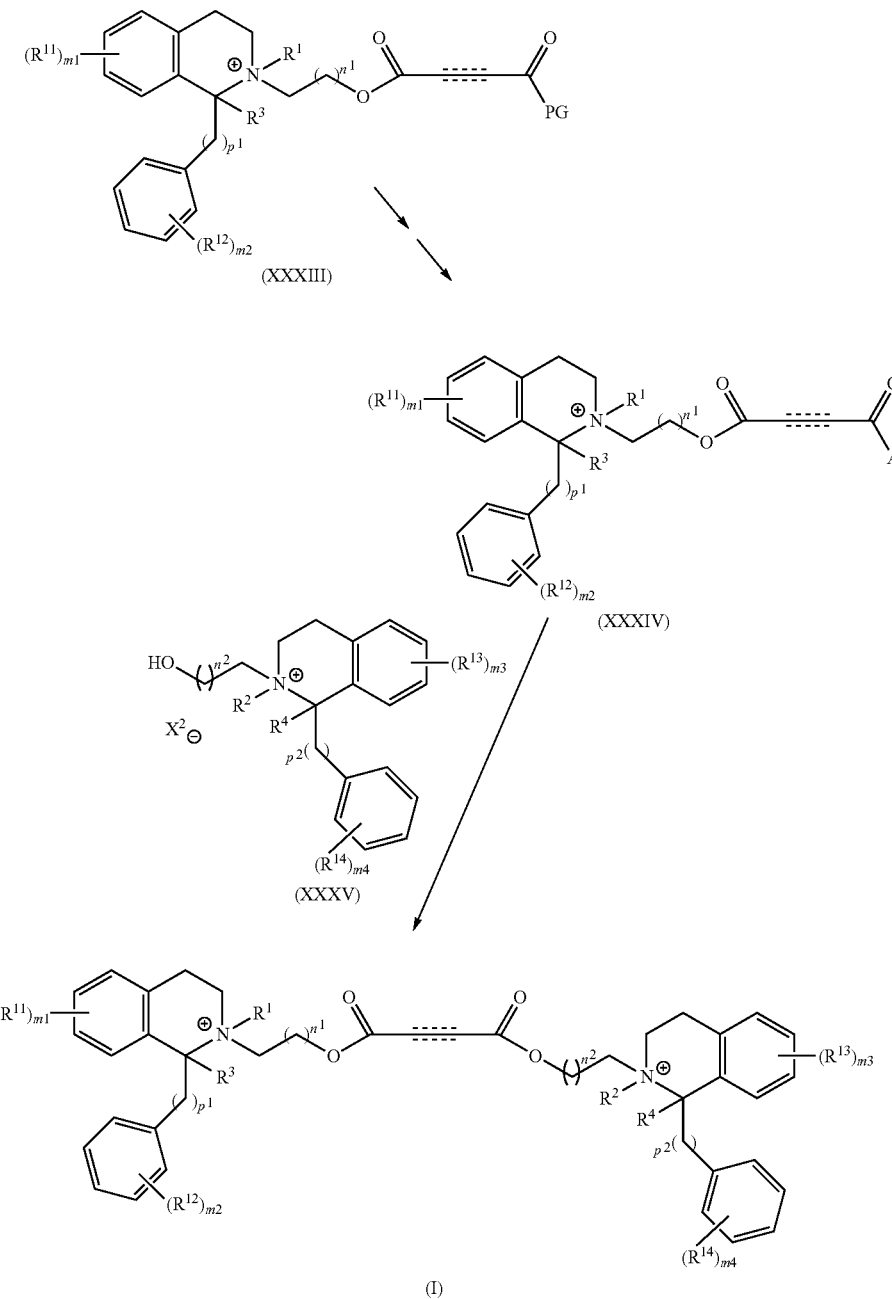

If an asymmetric diester is desired, particularly using a diacid for which a cyclic anhydride form is not sterically available, a more selective route can be employed, such as is shown in Synthetic Scheme III, above.

Starting with a mono-protected maleic, fumaric, succininic, or acetylenedicarboxylic acid, as are known in the art, the unprotected carboxyl group can be activated for ester formation. A suitable protecting group PG blocks one of the two carboxylic acid groups. The protecting group PG is suitable for removal under conditions do not affect the other groups in intermediate (XXXIII). For example, starting with a mono-t-butyl, mono-activated maleate, fumarate, succinate, or acetylenedicarboxylate, the PG group in (XXXIII) will thus be t-butyl. As is known in the art, a t-butyl ester can then be cleaved with mild acid to yield the compound with a free carboxylic acid group at that position (not shown), which can then be activated using standard procedures (intermediate (XXXIV)), and coupled with an isoquinolylalkanol (XXXV) that can be different from (XXXII), to yield an asymmetric compound of formula (I).

Accordingly, in various embodiments, the invention provides a method of synthesis of a maleate compound of the invention, comprising contacting a compound of formula (III)

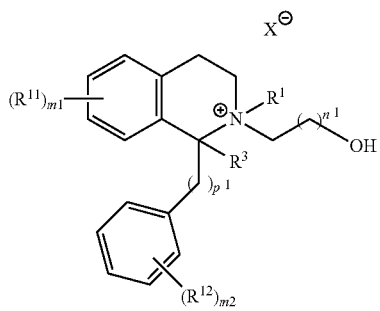

(III)

and maleic anhydride,
to provide a compound of formula (IIIA)

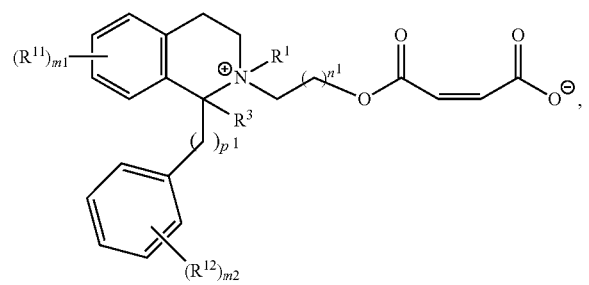

(IIIA)

or any salt thereof,
then, contacting the compound of formula (IIIA) and an independently selected compound of formula (IIIB)

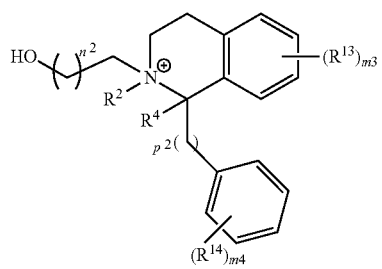

(IIIB)

under conditions suitable to bring about ester formation, to provide the maleate compound of claim 2.

More specifically, all of $R^{11}$, $R^{12}$, $R^{13}$ and $R^{14}$ can be methoxy, m1 and m3 can each independently be 2, 3, or 4, and m2 and m4 can each independently be 2 or 3.

In various embodiments, the invention provides a method of synthesis of a compound of the invention, such as a fumarate, maleate, succinate, or acetylenedicarboxylate, comprising contacting a compound of formula (III)

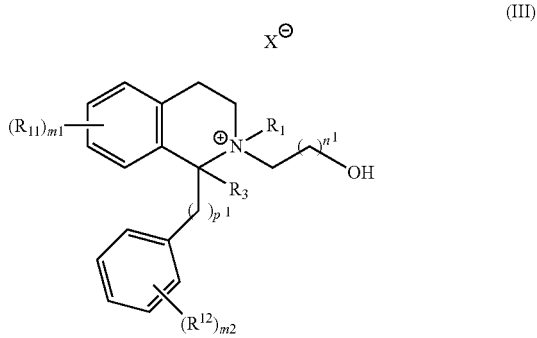

(III)

and an activated diacid of formula (IV)

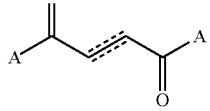

(IV)

wherein each A is each independently a carboxyl activating group, under conditions suitable to bring about ester formation,
to provide the compound of formula (IA)

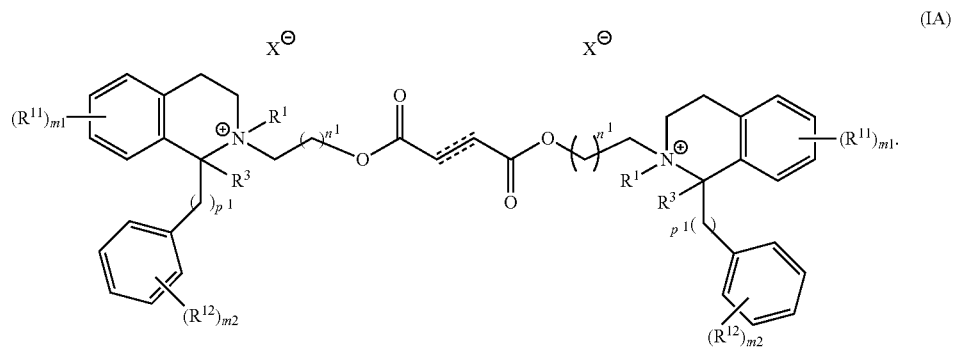

(IA)

More specifically, $R^{11}$ and $R^{12}$ can be methoxy, m1 can be 2, 3, or 4, and m2 can be 2 or 3.

In various embodiments, the invention provides a method of synthesis of a compound of claim 1, wherein PG is a carboxy-protecting group and A is a carboxy-activating group, comprising contacting a mono-protected mono-activated diacid of formula (XXXI)

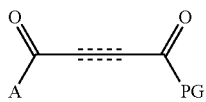
(XXXI)

and an isoquinolylalkanol of formula (XXXII)

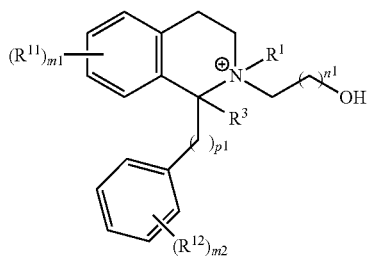
(XXXII)

under conditions suitable to bring about ester formation, to provide a compound of formula (XXXIII)

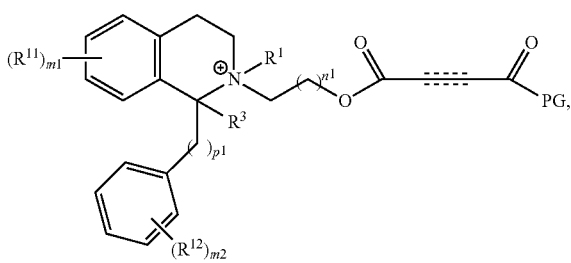
(XXXIII)

then, removing protecting group PG to provide a free carboxylic acid;
then, activating the free carboxylic acid to provide a compound of formula (XXXIV)

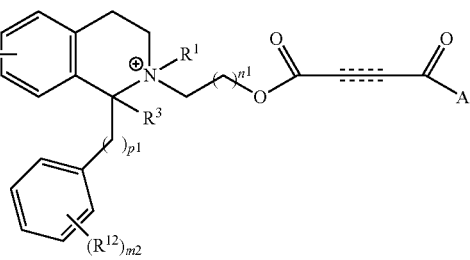
(XXXIV)

then, contacting the compound of formula (XXXIV), and a compound of formula (XXXV)

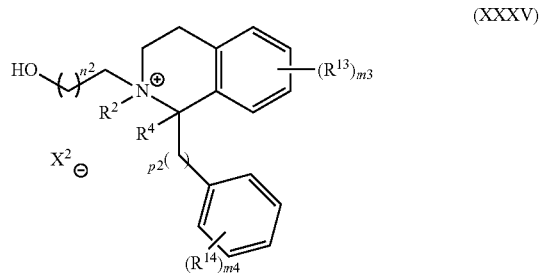
(XXXV)

under conditions suitable to bring about ester formation, to provide a compound of formula (I)

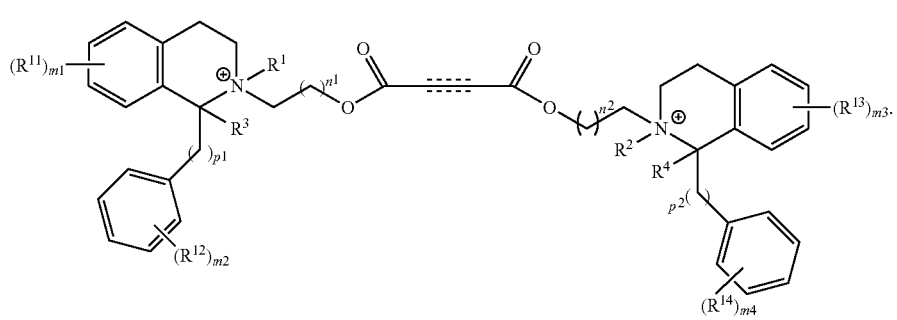
(I)

More specifically, $R^{11}$ and $R^{12}$ can be methoxy, m1 can be 2, 3, or 4, and m2 can be 2 or 3.

Pharmaceutical Compositions and Uses

Compounds of the invention can be used in various compositions adapted to induce neuromuscular blockade in patients as needed in surgical anesthesia. In various embodiments, a compound of the invention produces, upon administration of an effective amount of the compound to a patient, a neuromuscular blockade.

In various embodiments a compound of the invention, administered by injection as a suitable solution, produces neuromuscular blockade of sufficient completeness to enable the compound to effectively be used as an adjunct to anesthesia in major surgery. In various embodiments, an effective amount of an inventive compound for administration to a human patient is about 0.01-10 mg per kg patient bodyweight. More specifically, in various embodiments, the effective amount is about 0.1-1 mg per kg patient bodyweight. The compound can be administered in a manner known to the anesthesiologist or surgeon of ordinary skill in the art, using the methods and apparatus well known for this procedure in surgery.

In various embodiments, the invention provides a composition comprising a compound of the invention and a pharmaceutically acceptable excipient. The composition can be adapted for parenteral administration to a human patient, comprising an injectable solution of the compound in a suitable biocompatible solvent. In various embodiments, an injectable solution of a compound of the invention in a suitable solvent comprises about 1 mg/mL to about 10 mg/mL of the compound per dose of the injectable solution. The solution can be administered via syringe, via intravenous drip, or via any of the techniques well known to the practitioner of the art.

In various embodiments, a suitable biocompatible solvent comprises sterile, pyrogen-free water. The solvent can further comprise isotonic NaCl, or other tonicity adjustment substances. In various embodiments, the suitable biocompatible solvent can comprise alcohol, a polyethylene glycol, DMSO, or any mixture thereof, which can be neat or can be in a mixture with water.

Compounds of the invention are known to be, to some extent, unstable over prolonged storage in alkaline medium. Accordingly, a dosage form of the invention can be adjusted to an acidic pH for stabilization. In various embodiments of a solution dosage form of the invention, the pH of the solution is about 2.5 to about 3.5. In various embodiments, the dosage form can be adapted for frozen storage, such as by packaging in containers that can withstand freezing, bearing freeze-resistant labeling, and the like.

In various embodiments, the invention provides compounds, the neuromuscular blockade effects of which are reversible by administration to the patient of an effective amount of a thiol compound. An outstanding feature of the present invention is the ready reversibility of the neuromuscular blockade effects of some of the compounds of the invention by administration to the patient, such as by intravenous administration, of a thiol compound, such as L-cysteine or a pharmaceutically acceptable salt thereof, D-cysteine or a pharmaceutically acceptable salt thereof, or glutathione or a pharmaceutically acceptable salt thereof, or a stereoisomer of glutathione or a pharmaceutically acceptable salt thereof.

As discussed herein, without wishing to be bound by theory, the inventor believes that inactivation of the neuromuscular blockade effects of various embodiments of compounds of the invention by a thiol compound takes place via an intermolecular reaction in vivo of the inventive NMBA compound and the thiol, producing a reaction product therebetween. Each of the compound classes of fumarates, maleates, and acetylenedicarboxylates are believed to be susceptible to this reaction, and it has been found that the neuromuscular blockade effects of specific fumarates (e.g., CW 002) and maleates (e.g. CW 011) are reversible by administration of thiol compounds such as cysteine (L or D) or glutathione. It has also been found that the neuromuscular blockade effect of a succinate of the invention is not reversible by administration of a thiol compound. These observations support the mechanistic theory, and lead the inventor to the prediction that acetylenedicarboxylates of the invention will be both potent and reversible NMBAs.

In various embodiments, the invention provides a method of inducing neuromuscular blockade in a patient, comprising administering an effective amount of a compound of the invention to the patient. In various embodiments, the effective amount is about 0.01-10 mg per kg patient bodyweight. More specifically, the effective amount is about 0.1-1 mg per kg patient bodyweight. The inventive method can comprise inducing neuromuscular blockade as part of a regimen of anesthesia, which as described above is well known to be desirable for carrying out many types of surgical procedures where movement of the patient undergoing surgery is dangerous and undesirable.

In various embodiments, administration of a compound, for example in the form of a composition of the invention as described above, to a patient produces neuromuscular blockade wherein the neuromuscular blockade is non-depolarizing. In various embodiment, the neuromuscular blockade is achieved with little or no circulatory effect.

An outstanding feature of various embodiments of compounds of the invention is that the neuromuscular blockade can be subsequently reversed by administration of a thiol compound. It is believed by the inventor herein that reversal occurs by a reaction of the thiol compound with a reactive multiple bond of an inventive compound. Accordingly, fumarates, maleates, and acetylenedicarboxylates of the invention are believed to have thiol-reversible effects, whereas succinates of the invention are believed to have thiol-irreversible effects, or at least have effects not as rapidly reversed by thiols as are the effects of the fumarates, maleates, and acetylenedicarboxylates of the invention.

The thiol compound used for reversal of the neuromuscular blockade can be L-cysteine or a pharmaceutically acceptable salt thereof, D-cysteine or a pharmaceutically acceptable salt thereof, or glutathione or a pharmaceutically acceptable salt thereof, or a stereoisomer of glutathione or a pharmaceutically acceptable salt thereof.

In various embodiments, the blockade is reversible within about 2-5 minutes after administration of the thiol compound to the patient following induction of the neuromuscular blockade. Rapid reversal can be advantageous in carrying our surgical procedures, as it allows mechanical respiration to be used for only the necessary period of time, insomuch as the blockade can inhibit the action of the patient's diaphragm in natural respiration. Accordingly, the thiol compound such as cysteine (L or D) or a salt thereof can be administered to the patient immediately following a surgical procedure for which a compound of formula (I) had been previously administered to the patient. For example, the thiol compound used to immediately reverse the neuromuscular blockade following surgery can comprise cysteine or a salt thereof wherein the cysteine or salt thereof is administered at a dose of about 10 mg/kg to about 50 mg/kg on a free base basis. More specifically, the cysteine or salt thereof can be D-cysteine hydrochloride. Use of a D-cysteine salt can be more free of unwanted side-effects than the use of an L-cysteine salt. A solution of L-cysteine, D-cysteine, glutathione, or a stereoisomer of glutathione can be adjusted to a pH of about 5-6 prior to administration to the patient to reverse the neuromuscular blockade.

Accordingly, the invention provides a use of a compound of the invention for creating neuromuscular blockade, wherein in various embodiments the blockade is reversible by administration of a thiol compound.

In various embodiments, the invention provides a dosage form of a compound of the invention comprising an injectable solution of the compound in a suitable biocompatible solvent. The dosage form can comprise about 1 mg/mL to about 10 mg/mL of the compound in the biocompatible solvent. As discussed above, the suitable biocompatible solvent can comprise sterile, pyrogen-free water, optionally containing isotonic NaCl. Or, the suitable biocompatible solvent can comprise alcohol, a polyethylene glycol, DMSO, or any mixture thereof, optionally further including water or an isotonic NaCl solution. In various embodiments the pH of the solution is about 2.5 to about 3.5 to stabilize the dosage form against degradation over time of the NMBA. The dosage form of the invention can be adapted for frozen storage. In various embodiments the pH of the solution can be adjusted, for example to a pH of about 5-6, prior to administration to the patient.

In various embodiments, the invention provides a comprising a compound of the invention in a first container and, a buffer to adjust the pH of the solution of the first container, the second container, or both, to about 5-6 prior to administration to the patient.

EXAMPLES

Further specific synthetic procedures for compounds of the invention are provided for compounds CW002 (a fumarate), CW011 (a maleate), and gantacurium, a chlorofumarate (control) compound. For specifics concerning gantacurium, see, for example, WO2005/041960.

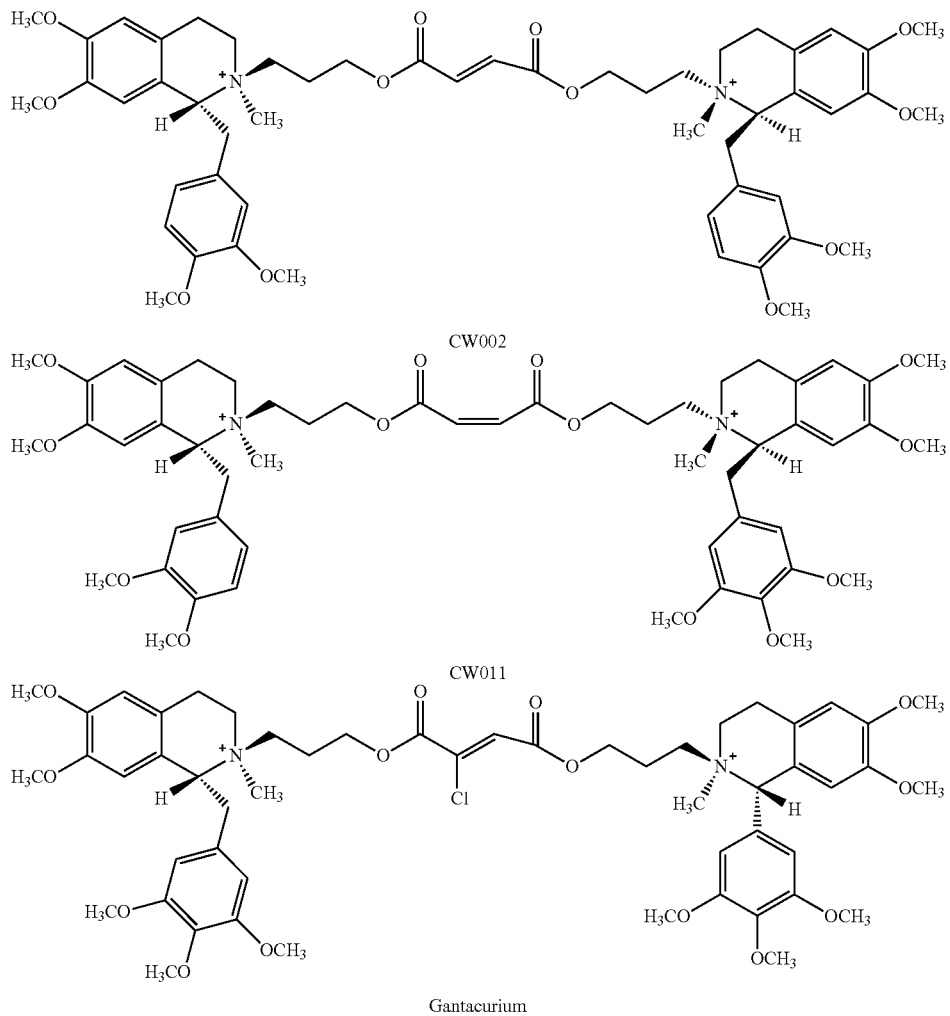

optionally, a thiol compound suitable for reversing the neuromuscular blockade effect of the compound on a patient in a second container. The second container with the thiol compound in suitable formulation can be supplied when the inventive compound comprises a thiol-reversible compound. The first container can comprise a dosage form of any of the invention as discussed above. When a second container with a neuromuscular blockade-reversing thiol compound is provided, the the second container of the kit can comprise a solution of L-cysteine hydrochloride, D-cysteine hydrochloride, or both. In various embodiments, the solution can be buffered to a pH of about 2-3 for storage. In various embodiments, the kit further comprises a third container comprising Isoquinoline alcohols (e.g., isoquinolylalkanol compounds (XII) and (XV), Synthetic Scheme 1, above) were synthesized from the corresponding aryl amines and aryl acids in a series of 7-10 chemical operations depending on the desired aryl methoxy group substitution pattern. The synthetic steps include amide formation, Bischler-Napieralski isoquinoline formation, imine reduction to give a racemic tetrahydroisoquinoline, reductive methylation of the isoquinoline amine and chiral resolution to obtain the desired isoquinoline enantiomer. The tetrahydroisoquinoline alcohol was isolated in high stereoisomeric purity after (1) alkylation of the enantioenriched isoquinoline with a cyclic propyl sulfate to give a mixture of quaternary isoquinoline sulfate diastereomers, (2) selective crystallization of the desired isoquinoline diastereomer and (3) hydrolysis to give the quaternary alcohol chloride after treatment with an ion exchange resin.

CW 002, a symmetrical fumarate-based neuromuscular blocking agent (NMBA) was prepared in one chemical step from compound (XIIA), an isoquinolylalkanol of formula (XII) wherein $R^1$ is methyl and $R^3$ is hydrogen, n1 is 2, p1 is 1, and $R^{11}$ and $R^{12}$ are methoxy, with a substitution pattern as shown:

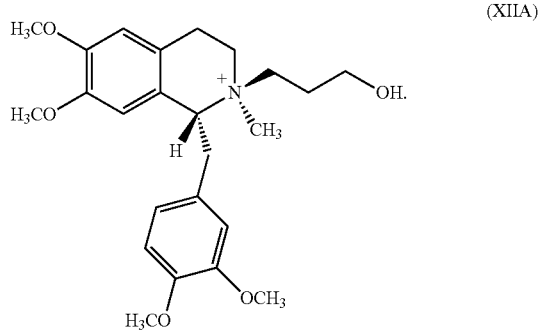

(XIIA)

A mixture of compound (XIIA) and 4 Å molecular sieve powder in anhydrous 1,2-dichloroethane was treated with a slight excess of fumaryl chloride at ambient temperature to give crude CW 002. The product was purified by aqueous workup involving filtration, extraction of product to an aqueous solution, salting the product to dichloromethane and washing the solution with aqueous base and brine. CW 002 was isolated as an off-white to light yellow solid after extraction into water followed by lyophilization. Product purity was determined by high performance liquid chromatography (HPLC) peak area % based on extensive chemical characterization of a CW 002 standard (HPLC, Nuclear Magnetic Resonance, Infrared Spectroscopy, Mass Spectrometry, Ultraviolet Spectroscopy and elemental analysis).

CW 011, an asymmetrical maleate, was prepared in three chemical transformations also starting with compound (XIIA). A solution of (XIIA) and maleic anhydride in acetonitrile (ACN) was charged with triethylamine at ice bath temperature. Monosubstituted maleate compound (XIIIA) (Synthetic Scheme 1, with variable substituents as defined for compound (XIIA) was isolated by precipitation and was converted to an acid chloride in anhydrous 1,2-dichloroethane by treatment with oxalyl chloride. A solution of the acid chloride in 1,2-dichloroethane was coupled with isoquinolylalkanol (XIIB)

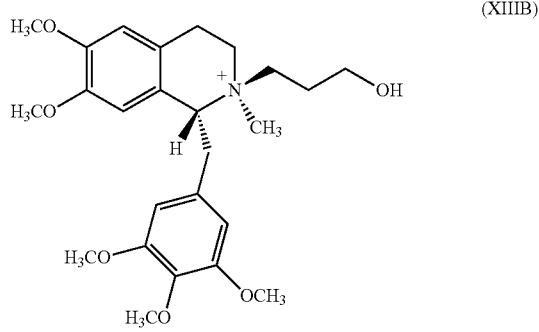

(XIIIB)

in the presence of 4 Å MS powder. The compound was purified in the same manner as CW 002 with the exception of a carbon treatment used to reduce colored impurities in the aqueous CW 011 solution prior to lyophilization. CW 011 was isolated as an off-white to pale yellow solid. Product purity was determined by HPLC assay with product peak identity assigned by analogy to the synthesis and purification of the well characterized CW 002 and gantacurium processes.

Gantacurium, an asymmetrical chlorofumarate, was prepared in four chemical transformations from compound (XIIIB) using minor modifications of previously reported chemistry, see WO2005/041960. Isoquinolylalkanol compound (XIIIB) was condensed with trans-2,3-dichlorosuccinic anhydride and triethylamine in acetonitrile solvent to provide a monoester of chlorofumaric acid, which was then condensed with isoquinolylalkanol compound (XIIIC):

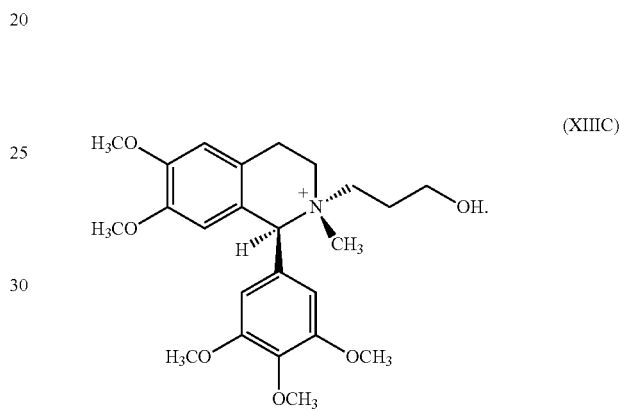

(XIIIC)

Gantacurium was isolated as an off-white to light yellow solid following extensive aqueous washing to remove excess and lyophilization. Product purity was determined by HPLC peak area % based on extensive chemical characterization of a CW 002 standard (HPLC, Nuclear Magnetic Resonance, Infrared Spectroscopy, Mass Spectrometry, Ultraviolet Spectroscopy and elemental analysis).

As discussed below, it is believed that the reversal of neuromuscular blockade of compounds of the invention by thiol compounds such as cysteine or glutathione in their various stereochemical forms (e.g., L-cysteine and D-cysteine, and glutathione including L-cysteine, or the glutathione stereoisomer containing D-cysteine and L- or D-glutamate). To provide confirmatory evidence of this mechanism of reversal, a sample of a cysteine/CW002 adduct was synthesized as a standard.

Isolation of a CW 002-Cysteine Adduct Intermediate

The initial adduct believed to be formed when L-cysteine reacts with CW 002, shown below,

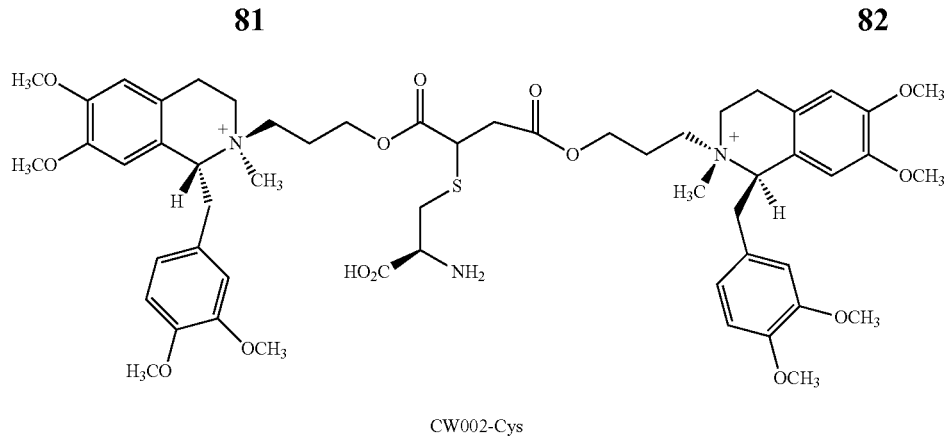

CW002-Cys was prepared in one step from CW 002. CW 002 was dissolved in deionized water to give a solution concentration of 37 mg/ml at a pH of 6.6. A 5 mol % excess of L-cysteine hydrochloride monohydrate was added in one portion at ambient temperature to give a solution pH of 2. Stirring for 12 hours gave complete consumption of CW 002, as observed by HPLC. CW002-Cys was isolated as an off-white solid after reaction mixture lyophilization. Product purity was estimated at 95% by HPLC peak area %. IR analysis of CW002-Cys showed an absence of the diester carbon-carbon double bond observed in the IR spectrum of CW 002.

At low pH and temperature, one new peak was formed on L-cysteine addition as the peak corresponding to CW 002 diminished. This new peak corresponds to the initial peak observed in the in vitro L-cysteine adduction experiments at 37° C. and a pH of 7.4. At elevated temperature and pH, such as conditions used to mimic in vivo reactivity, this initial peak quickly diminishes over time (t½~60 min) while two new adduct peaks arise secondary to alkaline hydrolysis of the adduct. However, at ambient temperature and a pH of 2, the initial adduct is stable for >24 hours, allowing for isolation of the intermediate.

In Vitro Degradation of Compounds of the Invention by L-Cysteine

First, to evaluate stability at physiological pH and temperature, CW 002, CW 011, or gantacurium was dissolved in phosphate buffer (pH 7.4) at a concentration of 1000 µg/ml. Stability at pH 7.4 and 37° C. was monitored by high performance liquid chromatography for at least 2 hours to evaluate background alkaline hydrolysis of each compound.

In a second experiment, to evaluate degradation in the presence of L-cysteine, buffered solutions (pH 7.4) of gantacurium, CW 002 or CW 011 were freshly prepared at 37° C. to give experimental concentrations of 1000 µg/mL (CW 002 and CW 011) and 200 µg/mL (gantacurium), after addition to and mixing with a 5% Molar excess of L-cysteine at time=0.

The concentration of neuromuscular blocking agent/parent compound remaining at specified time points after mixing was determined by high performance liquid chromatography. The concentration of blocking agent at each time point was determined from a separately prepared reaction mixture, due to the rapid rate of L-cysteine adduction. See Table 1, below. The reaction rate constant for the second order reaction of each neuromuscular blockade agent (NMBA) with L-cysteine was derived by plotting the natural log of ([NMBA]$_t$[L-cysteine]$_{t=0}$/[NMBA]$_{t=0}$[L-cysteine]$_t$) vs. time.

Adduction t½ was calculated at specific concentrations selected for each new compound reflecting their relative potencies in vivo, using the calculated reaction rate constant, as shown in Table 1a, below. Concentrations selected were 200, 100 and 50 µg/ml which are approximately proportional to the relative potencies (ED 95) of gantacurium, CW 002 and CW 011 respectively. A degradation (adduction) pathway in the presence of L-cysteine for each of the three compounds was proposed.

The reaction of L-cysteine with CW 002, CW 011 or gantacurium is first order in the case of both the neuromuscular blockade agent (NMBA) and L-cysteine, represented by the rate equation (1).

$$d[\text{Adduct}]/dt = -d[\text{NMBA}]/dt = k_a[\text{NMBA}][L\text{-cysteine}] \quad (1)$$

Calculation of the L-cysteine adduction half time requires experimental derivation of the reaction rate constant, $k_a$, for each compound. The initial concentrations of NMBA and L-cysteine are unequal in the experiments conducted for this study, thus integration of equation 1 gives equation 2, where $[NMBA]_0$ is the NMBA concentration at time equals 0 and $[NMBA]_t$ is the NMBA concentration at a time point, t.

$$\frac{1}{[NMBA]_0 - [L\text{-cysteine}]_0} \ln \frac{[NMBA]_t [L\text{-cysteine}]_0}{[NMBA]_0 [L\text{-cysteine}]_t} = k_a t \quad (2)$$

A plot of the ln(([NMBA]$_t$ [L-cysteine]$_0$)/([NMBA]$_0$ [L-cysteine]$_t$)) versus time (ln* vs. t) gives a line, with slope equal to $k_a$([NMBA]$_0$−[L-cysteine]$_0$). An adduction reaction half time can be calculated by solving for $k_a$ to be used in equation 3.

$$t_{1/2} = \frac{1}{k_a([NMBA]_0)} \quad (3)$$

See, for example, Carroll F A; Perspectives on Structure and Mechanism in Organic Chemistry, 1998, Brooks/Cole Publishing, Pacific Grove Calif.; Lowry T H, Richardson K S; Mechanism and Theory in Organic Chemistry, $3^{rd}$ Edition 1987, Harper Collins Publishers, New York, N.Y.

NMBA Standard Solutions

NMBA standard solutions were prepared by a method similar to that used to prepare hydrolysis standards. The standards were prepared at 1000 µg/mL for CW 002 and CW 011 and 200 µg/mL for gantacurium.

Kinetics Experiments

Solutions used for determination of NMBA concentration at the reported times for CW 002 and CW 011 were prepared as follows: L-cysteine hydrochloride monohydrate was charged to a volumetric flask in de-ionized water. A 5 mL aliquot of the L-cysteine solution (1.05 equiv. L-cysteine with respect to NMBA) was transferred by volumetric pipette to a flask held at 37.0±0.3° C. CW 002 or CW 011 was then charged to a separate 25 mL volumetric flask and diluted to volume with pH 7.4 phosphate buffer at 37.0° C. The NMBA solution was then immediately transferred to the flask containing L-cysteine to give an initial NMBA concentration of 1000 μg/mL. Solutions used for determination of gantacurium concentration versus time were prepared in a similar manner to give an initial concentration of 200 μg/mL. T=0 was defined as the time of addition of NMBA solution to L-cysteine solution. The times listed in the results table show the point of HPLC sample injection following mixing of L-cysteine and NMBA at time=0 (Table 1, below).

Results

The data collected for the adduction kinetics experiments is found in Table 1. Rate constants were calculated using equation (3) and the slope of the trend line derived from each data set. The strong linear correlation of the data within each set supports the use of second order kinetics for analysis of the cysteine adduction reactions.

TABLE 1

L-cysteine Adduction Kinetics Trials

| NMB | Trial | Time (Sec) | NMBA peak area (mAU's) | [NMBA] (M) | [L-cysteine] (M) | ln* |
|---|---|---|---|---|---|---|
| CW 002 | Std | 0 | 11915.3 | 0.000976 | 0.00106 | — |
|  | 1 | 142 | 2746.0 | 0.000224 | 0.000308 | −0.240 |
|  | 2 | 170 | 2350.7 | 0.000192 | 0.000276 | −0.277 |
|  | 3 | 188 | 2237.9 | 0.000183 | 0.000267 | −0.297 |
| CW 011 | Std | 0 | 10754.2 | 0.000947 | 0.00104 | — |
|  | 1 | 123 | 2587.0 | 0.000228 | 0.000321 | −0.248 |
|  | 2 | 132 | 2500.5 | 0.000221 | 0.000314 | −0.256 |
|  | 3 | 143 | 2293.0 | 0.000202 | 0.000295 | −0.284 |
|  | 4 | 182 | 1765.4 | 0.000155 | 0.000248 | −0.378 |
| Gantacurium | Std | 0 | 2594.0 | 0.000180 | 0.002070 | — |
|  | 1 | 59 | 476.7 | 0.000033 | 0.000060 | −0.46 |
|  | 2 | 67 | 384.2 | 0.000027 | 0.000054 | −0.56 |
|  | 3 | 70 | 344.2 | 0.000024 | 0.000051 | −0.62 |
|  | 4 | 78 | 281.5 | 0.000020 | 0.000047 | −0.73 |

*ln = ln ((([NMBA]$_t$[L-cysteine]$_{t=0}$)/([NMBA]$_{t=0}$[L-cysteine]$_t$)).

Reaction half times were calculated using equation 4 and the experimentally determined rate constants. The initial NMBA concentrations were chosen to reflect the relative potency observed in vivo. In vivo experiments have shown that CW 011 displays approximately twice the potency of CW 002 and four times the potency of gantacurium when generating a comparable level of neuromuscular blockade. Table 1a shows calculated L-cysteine adduction half-times as derived from the data of Table 1.

TABLE 1a

L-cysteine Adduction Reaction Half Time

| NMBA | Plot Slope | $k_a$ (M$^{-1}$s$^{-1}$) | [NMBA]$_0$ (M) | $t_{1/2}$ (minutes) |
|---|---|---|---|---|
| CW 002 | −0.0012 | 14.3 | 0.000102 | 11.4 |
| CW 011 | −0.0023 | 24.7 | 0.0000493 | 13.7 |
| Gantacurium | −0.0145 | 529.6 | 0.000188 | 0.2 |

Studies in Anesthetized Rhesus Monkeys

Animal Preparation and Care

Experiments were approved by the Institutional Animal Care and Use Committee of Weill Medical College of Cornell University (New York, N.Y.) and of Albany Medical College (Albany, N.Y.), where the studies were conducted. A colony of 10 adult male monkeys (Macaca mulatta) weighing 8-18 kg was studied at ~6 week intervals. Animals were housed and cared for in accordance with the Guide for Care and Use of Laboratory Animals (National Research Council, Washington, D.C.). They were fed a standard Old World monkey diet, enriched with fruits and vegetables, and other dietary novelties and were followed throughout the study to verify normal health by physical examination, body weight, and clinical laboratory studies (Complete Blood Count, Blood Urea Nitrogen and creatinine, and liver function tests).

Anesthesia and Experimental Set Up

On the day of each study, monkeys received ketamine (7-10 mg/kg i.m.) followed by tracheal intubation under topical anesthesia with 4% lidocaine. Ventilation was controlled at 10 mL/kg and 20 breaths/min with isoflurane (1.0-2.0%) and N$_2$O/O$_2$ (2:1 mixture). Ringers lactate was administered at ~10 ml kg$^{-1}$ h$^{-1}$. Arterial pressure was monitored from a femoral, superficial tibial, or radial (22 gauge) cannula. Heart rate was measured by tachograph from the arterial pulse wave. Core temperature was kept at 36.5-38.0° C. by warming blankets. Electrocardiogram and pulse oximetry were monitored continuously.

Needle electrodes (25 gauge) transmitting square-wave pulses of 0.2 msec duration at supramaximal voltage which were generated by a Grass S-88 stimulator (Grass Instruments, Quincy, Mass.) were placed at the peroneal nerve at the knee to elicit twitch responses of the extensor digitorum of the foot at 0.15 Hz. A small slip (10-20%) of the tendon was dissected free under sterile technique and tied to a Grass FT 10 force transducer (Grass Instruments, Quincy, Mass.) at a baseline tension of 50 gm. Train-of four stimulation (TOF, 2 Hz for 2 sec) was interposed at appropriate points, especially 1-2 min prior to NMBA dosing and following recovery of twitch to 95% of baseline, where TOF was subsequently evaluated every 1-2 min.

Recordings of circulatory and neuromuscular data were made on a Grass 7B polygraph (Grass Instruments). A baseline period of 15-20 min was allowed for stabilization of recordings prior to dosing.[2]

At the end of each experiment, animals were awakened, analgesics were given per veterinary practice, and animals were returned to their domiciles and attended until standing.

Determination of Neuromuscular Blocking Potency and Duration

Dose-response curves for twitch blockade by gantacurium, CW 002, CW 011, cisatracurium, CW002-Cys, NB 938-69, NB 1064-81, NB 802-17 (CW 001), NB 832-65, and NB 1163-79, structures of which are all shown above, were generated as follows. To ensure minimal cumulative/residual influence on these data, sequential dosing was done in escalating fashion. Successive doses were separated by at least three estimated half lives beyond complete recovery of the previous dose to TOF of 110-120%, which is normal for these monkeys. Only the first one or two doses yielding 5 to 99% blockade were included from any single experiment for computation of dose-response data.

Comparative studies of spontaneous recovery versus antagonism/reversal were done at least 3 estimated half-lives following dose-response studies.

ED 50 and ED 95 were computed from the regression of log dose vs. the logit of percentage blockade of twitch.

CW002-Cys, the L-cysteine adduct of CW 002, was available in limited quantity and was administered in cumulative fashion to three animals to compare approximate potency and duration of effect versus its parent compound CW 002.

TABLE 2

Potency and Duration of Effect of Gantacurium, CW 011, CW 002 and its Cysteine Adduct, and Cisatracurium in Monkeys Under Insoflurane‡

| COMPOUND | ED 50 (mg/kg ± SD/SEM)≠≠ | (n) | ED 95 (mg/kg ± SD/SEM)≠≠ | (n) | Administered Dose (mg/kg)≠≠≠ | (n)* | Duration+ (min ± SD/SEM) |
|---|---|---|---|---|---|---|---|
| GANTACURIUM | 0.032 ± 0.018/0.0026 | (51) | 0.100 ± 0.0035/0.005 | (51) | 0.10 | (29) | 7.3 ± 2.1/0.4 |
|  |  |  |  |  | 0.50 | (9) | 10.4 ± 3.1/1.0* |
| CW 002 | 0.022 ± 0.008/0.0020 | (18) | 0.042 ± 0.016/0.004 | (18) | 0.05 | (8) | 20.5 ± 7.1/2.5 |
|  |  |  |  |  | 0.15 | (50) | 28.1 ± 7.1/1.0** |
| CW 011 | 0.014 ± 0.004/0.0009 | (23) | 0.025 ± 0.008/0.002 | (23) | 0.03 | (6) | 20.8 ± 6.3/2.6 |
|  |  |  |  |  | 0.10 | (11) | 33.3 ± 7.2/2.2** |
| CISATRACURIUM | 0.017 ± 0.003/0.0007 | (22) | 0.028 ± 0.006/0.0024 | (22) | 0.035 | (5) | 35.5 ± 8.2/3.7 |
|  |  |  |  |  | 0.12 | (4) | 58.0 ± 18.6/9.3 |
| CW002-Cys (Cysteine adduct of CW 002) | 0.750 ± 0.499/0.1384 | (13) | 2.76 ± 0.96/0.27 | (13) | N/A | N/A | ~30-35+++ |
| NB 968-39 | NA | (18) | 0.042 ± 0.003 | (18) | 0.04 | (5) | 19.3 ± 2.2 |
|  |  |  |  |  | 0.175 | (4) | 30.2 ± 3.5 |
| NB 1064-81 | NA | (17) | 0.084 ± 0.007 | (17) | 0.10 | (8) | 15.6 ± 1.50 |
|  |  |  |  |  | 0.40 | (6) | 29.3 ± 2.6 |
| NB 802-17 (CW 001) | NA | (7) | 0.033 ± 0.005 | (7) | 0.03 | (2) | 35.0 ± 15.0 |
|  |  |  |  |  | 0.10 | (7) | 49.4 ± 5.8 |
| NB 832-65 (CW 003) | NA | (5) | 0.132 ± 0.014 | (5) | 0.10 | (2) | 19.5 ± 3.5 |
|  |  |  |  |  | NA |  | NA |
| NB 1163-79 | NA | (11) | 0.032 ± 0.003 | (11) | 0.04 | (7) | 27.2 ± 2.6 |
|  |  |  |  |  | NA |  | NA |

ED = effective dose
SD = standard deviation
SEM = standard error of the mean
‡Twitch of extensor digitorum elicited at 0.15 Hz
+From injection to recovery of twitch to 95% of baseline
++Available in limited quantity
+++spontaneous recovery (times approximate) following cumulative dosage
(n) = Number of points used to construct the dose-response curve
(n)* = number of observations
≠≠Calculated from Dose-response Curve
≠≠≠Actual doses administered
*p < 0.01 vs. CW 002 and CW 011
**p < 0.01 vs. Cisatracurium
Reversal of Neuromuscular Blockade by Cysteine
Definitions

| | |
|---|---|
| ED 95: | The calculated dose required for 95% block of twitch |
| TOF | Train-of-four ratio, T4/T1 following 2 Hz for 2 sec stimulation |
| Duration of action: | Duration from injection to recovery of twitch to 95% of control height |
| 5-95% recovery time: | Time interval for twitch recovery from 5% to 95% twitch height |
| Classical Reversal or Antagonism: | Antagonism of blockade at 2% twitch height |
| Immediate Reversal or Antagonism: | Antagonism of blockade at 1 min following injection of 2-6x ED95 dose of the NMB |
| Full Reversal or Complete Reversal or Complete Antagonism: | Recovery of twitch to 95 percent or more of control height, and TOF to a value of 100% or more |
| Chemical Reversal: | Abolition of neuromuscular blockade by conversion of the active neuromuscular blocking drug to an inactive derivative in a purely chemical reaction requiring no enzymatic catalyst |
| Fully Effective Dose of Cysteine: | Dose required to restore neuromuscular function to normal, i.e., twitch > 95% and TOF 100% or more, within 5 minutes or less. |

Immediate Antagonism of CW 002 by L-Cysteine vs. Neostigmine: L-Cysteine Dose-Response A control dose of 0.15 mg/kg CW 002 was allowed to recover spontaneously to TOF 110-120%. A second dose was given 60 minutes later, followed one minute afterwards by either neostigmine (0.05 mg/kg+atropine 0.05 mg/kg) or L-cysteine (10, 20, 30 or 50 mg/kg). Total duration and 5-95% recovery intervals were compared during spontaneous recovery vs. antagonism by L-cysteine or reversal by neostigmine.

Immediate Antagonism by L-Cysteine of CW 011: Dose Response Comparing Optimal Dosage of L-Cysteine in Antagonism of Escalating Dosage of CW 011

This series of paired comparisons was designed to generate dose-response data comparing spontaneous recovery of high doses of CW 011 (from 4 to 64× ED95) versus immediate antagonism at +1 min by an optimal dose of L-cysteine (50 mg/kg), previously determined during studies of immediate antagonism of CW 002. This experiment was done to explore the limits of chemical antagonism by L-cysteine of these olefinic diester neuromuscular blocking drugs, using CW 011 as a typical example with an intermediate duration of action. Five groups of animals first received a control dose of CW 011 at 4, 8, 16, 32 or 64× ED 95 (0.1 to 1.6 mg/kg). Sixty minutes after spontaneous recovery of the control dose to TOF 110-120%, the same dose was repeated, followed 1 min later by L-cysteine (50 mg/kg). Total duration of action and 5-95% recovery interval were compared during spontaneous recovery and following antagonism by L-cysteine The reversal of neuromuscular blockade by cysteine (5-50 mg/kg i.v.) was studied. Reversal was tested as follows: full paralysis was induced by injection of a dose of approximately 2-6× ED 95 of the compound in question. After spontaneous recovery of this dose, a second identical dose was given 15-30 min later. Cysteine was then given at +1 min after injection of the neuromuscular blocking drug at a point where no twitch was apparent ("immediate reversal") or at the beginning of recovery from neuromuscular blockade at two percent twitch height ("classical reversal"). Comparisons were made among compounds with respect to rapidity and ease of cysteine reversal, by comparing 5-95% recovery times, and total durations of action (injection to 95% twitch recovery). Spontaneous recovery was compared with cysteine-accelerated recovery. Comparisons were also made in some cases (see CW 002) with neostigmine antagonism, using 0.05mg/kg neostigmine combined with atropine 0.03 mg/kg for reversal (neostigmine antagonism or cysteine reversal were tested on separate occasions).

Compounds CW002, CW011, and gantacurium all showed antagonism of neuromuscular blockade in standard "classical" fashion by neostigmine, at a point where spontaneous recovery from neuromuscular blockade was beginning, e.g. at 2% twitch height. Neostigmine, however, was ineffective when given immediately after the administration of the blocking drug.

Figure 1B:
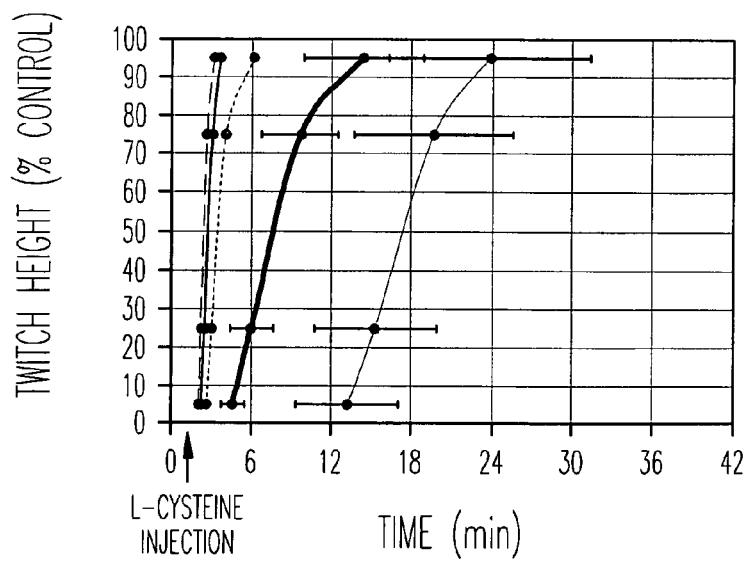

FIG. 1 shows the reversal rates of the neuromuscular blockade induced by CW 002 (a fumarate) in rhesus monkeys, in the presence of (A) neostigmine (0.05 mg/kg)/atropine (0.05 mg/kg), and in the presence of (B) L-cysteine at various concentrations ranging from 10 mg/kg to 50 mg/kg. As can be seen, using the neostigmine/atropine combination in FIG. (1A), reversal of the neuromuscular blockade is not achieved significantly faster than the spontaneous reversal of the blockade in the absence of any agent. However, in FIG. 1B) is can be seen that reversal of the blockade by cysteine is rapid and is dependent upon the cysteine dose administered, with reversal of blockade achieved in less than 6 minutes at all cysteine concentrations tested versus spontaneous reversal of more than 12 minutes. At the higher cysteine doses, reversal begins within 2-3 minutes of administration of the cysteine.

Figure 2B:
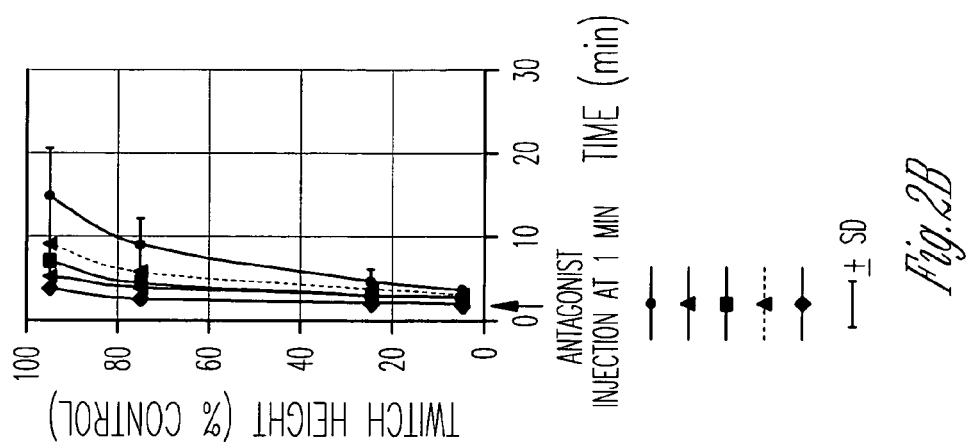
Figure 2A:
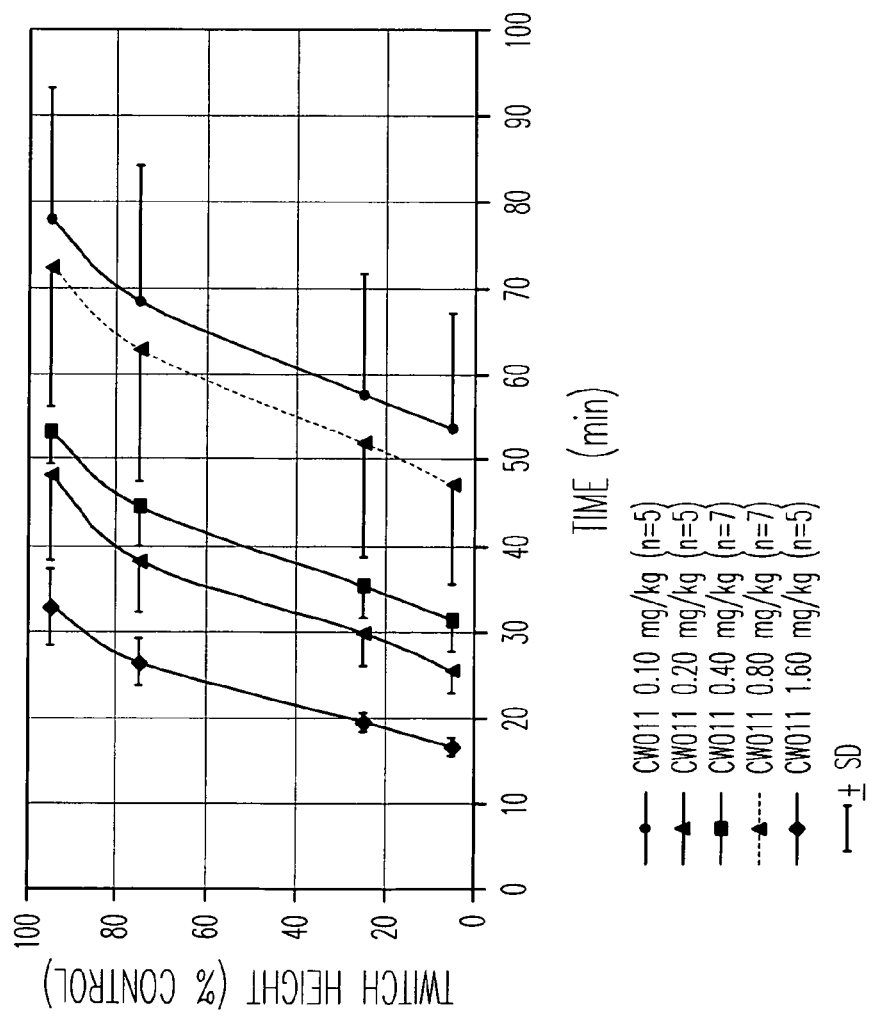

FIG. 2 shows the reversal rates of the neuromuscular blockade induced by CW 011 (a maleate) in rhesus monkeys. (A) shows the spontaneous reversal rate observed with increasing doses of CW 011, and (B) shows the rate of reversal observed following administration of various doses of L-cysteine (i.e., a fixed volume of a solution at concentrations ranging from 10 mg/kg to 50 mg/kg). As can be seen in (2A), the spontaneous reversal rate decreases with increasing CW 011 dose in the absence of any reversal agent such as cystein. However, in FIG. 2B) is can be seen that reversal of the blockade by cysteine is rapid and is dependent upon the cysteine dose administered, with reversal of blockade achieved in less than 6 minutes at all cysteine concentrations tested versus spontaneous reversal of more than 12 minutes. At the higher cysteine doses, reversal begins within 2-3 minutes of administration of the cysteine.

Figure 3:
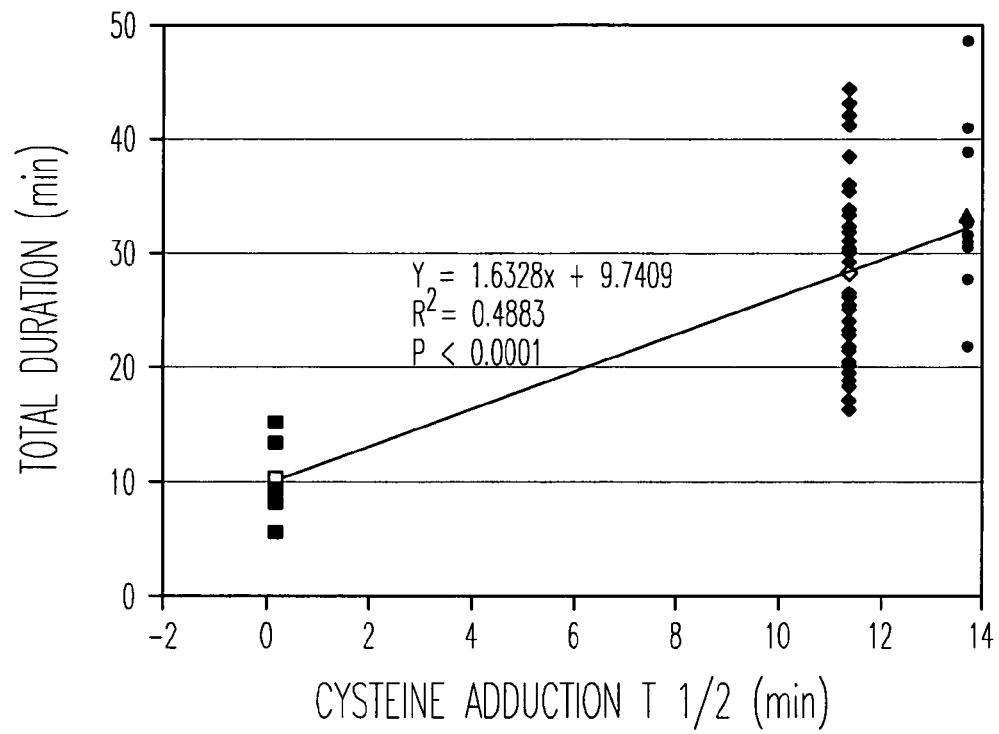

FIG. 3 shows a correlation between the rate of cysteine adduction to CW 002, CW 011, and gantacurium, as discussed above, with the duration of neuromuscular blockade observed when cysteine is administered to reverse the blockade. As can be seen, there is a correlation between the in vitro rate of reaction of the three NMBAs and the in vivo duration of effect of the NMBA in the monkey after administration of the cysteine, supporting the view that the mechanism by which reversal of neuromuscular blockade occurs is addition of the cysteine to the reactive double bond of the unsaturated fumarate and maleate compounds of the invention.

TABLE 3

Standard Reversal of CW 002 or Cisatracurium: Spontaneous Recovery vs. L-Cysteine or Neostigmine Administered at 2% Twitch Height

| DRUG | DOSE (mg/kg) | Type of Recovery | (n) | Total Duration (min ± SD/SE)[+] | 5-95% Interval (min ± SD/SET)[++] |
|---|---|---|---|---|---|
| CW 002 | 0.15 | Spontaneous Recovery | (7) | 24.8 ± 4.8/1.8 | 10.8 ± 1.7/0.7 |
| CW 002 | 0.15 | Neostigmine Reversal≠ | (7) | 22.5 ± 8.0/3.0*** | 8.6 ± 3.7/1.4[###] |
| CW 002 | 0.15 | Spontaneous Recovery | (4) | 29.4 ± 5.3/2.6 | 12.3 ± 2.6/1.2 |
| CW 002 | 0.15 | L-Cysteine Antagonism≠≠ | (4) | 19.9 ± 5.3/2.6** | 2.1 ± 0.6/0.3**[#] |
| Cisatracurium | 0.035 | Spontaneous Recovery | (8) | 36.9 ± 8.3/2.9 | 20.3 ± 6.7/2.4 |
| Cisatracurium | 0.035 | Neostigmine Reversal≠ | (4) | 24.8 ± 3.8/1.9** | 12.3 ± 2.6/1.3** |
| Cisatracurium | 0.035 | L-Cysteine Antagonism≠≠ | (4) | 40.0 ± 6.0/3.5*** | 23.3 ± 5.0/2.9*** |

SD = standard deviation
SE = standard error
n = number of observations
[+]Total Duration (min ± SE) from injection of NMBA to recovery of twitch to 95% of baseline
[++]Interval during recovery from 5% to 95% twitch height
**p < 0.01 vs. spontaneous recovery
[#]p < 0.01 vs. cisatracurium reversal by neostigmine
≠ = Dose 0.05 mg/kg + atropine 0.1 mg/kg
≠≠ = Dose 50 mg/kg
***= p > 0.05 vs. spontaneous recovery
[##]= p < 0.05 vs. cisatracurium reversal by neostigmine Comparison of Substituent and Stereochemical Effects on Potency and Duration Two stereoisomeric structures, CW 002 (R-trans, R-trans), and CW 003 (R-cis, R-cis) were tested in the rhesus monkey anesthesia bioassay for potency and duration. A third compound, CW 001 (R-trans, R-trans) bearing an additional methoxyl group on each of the two benzyl groups in the molecule, was also tested.

Rhesus monkeys were anesthetized with ketamine (7.5 mg/Kg) given intramuscularly or intravenously. Anesthesia was maintained with a mixture of isoflurane (1.5%), nitrous oxide (60%) and oxygen (40%). The common peroneal nerve was stimulated supramaximally with square wave pulses of 0.2 m sec duration at a rate of 0.15 Hz. Twitch contractions were recorded via the tendon of the extensor digitorum muscle.

In all animals, the trachea was intubated and ventilation was controlled at 12-15 ml/kg, 18-24 breaths per minute. A peripheral vein and artery were cannulated for drug administration and for recording of arterial pressure, respectively. In preliminary studies a neuromuscular blocking agent having one of the following structures was administered intravenously.

| Compound | Potency (ED95 mg/kg) | Duration (minutes)** | Duration at 4X ED95 |
|---|---|---|---|
| CW 001 | 0.04 | 30-40 | 50-60 |
| CW 002 | 0.04 | 20-25 | 30-35 |
| CW 003 | 0.10 | 25-30 | 45-50 |

*Results from studies in rhesus monkeys.
**From injection to 95% twitch recovery.

As can be seen, the two R-trans, R-trans isomers were both more potent than CW 003, the R-cis, R-cis isomer. However, the more substituted CW 001 was observed to be of longer duration (without administration of exogenous cysteine or

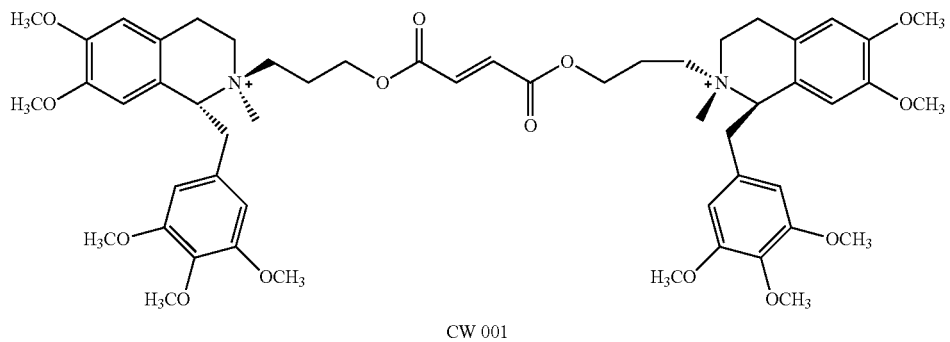
CW 001

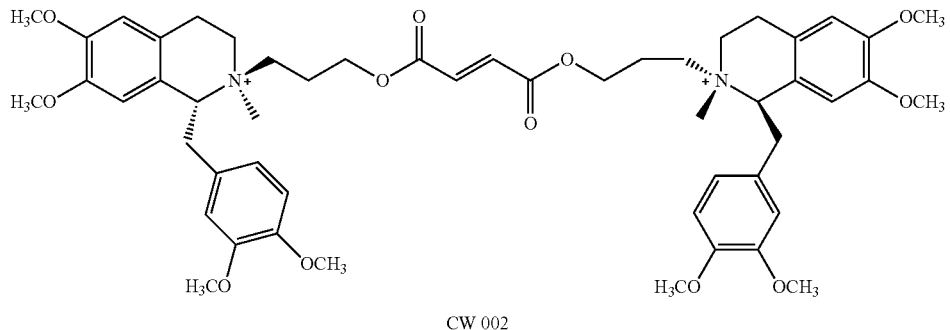
CW 002

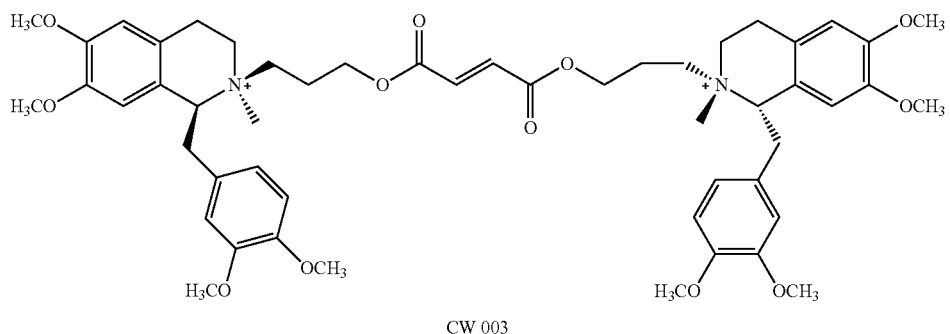
CW 003 glutathione) than were either CW 002 or CW 003, indicating a complex interaction of stereochemistry and substitution patterns in determining length of unreversed effect. All three compounds were reversible in effect by administration of cysteine or glutathione.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:
1. A compound of formula (I)

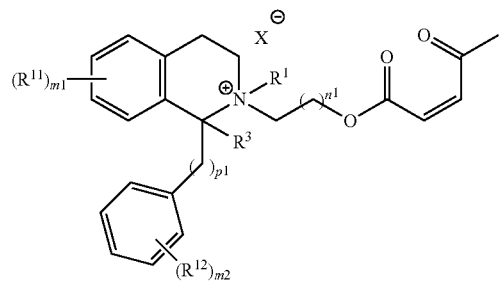
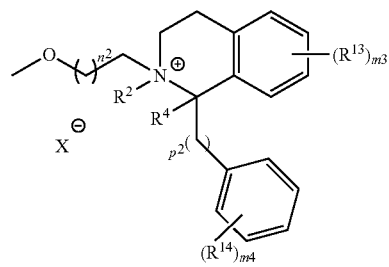

wherein $R^1$ and $R^2$ are each independently ($C_1$-$C_4$)alkyl, ($C_1$-$C_4$)alkenyl, or ($C_1$-$C_4$)alkynyl;

$R^3$ and $R^4$ are each independently hydrogen or ($C_1$-$C_4$)alkyl, ($C_1$-$C_4$)alkenyl, or ($C_1$-$C_4$)alkynyl;

$R^{11}$, $R^{12}$, $R^{13}$, and $R^{14}$ are each independently ($C_1$-$C_4$)alkoxy or ($C_1$-$C_4$)acyloxy; or any two adjacent $R^{11}$, $R^{12}$, $R^{13}$, or $R^{14}$ are methylenedioxy;

m1 and m3 are each independently 2, 3, or 4;

m2 and m4 are each independently 2 or 3;

n1 and n2 are each independently 1 to about 4;

p1 and p2 are each independently 0 or 1;

X is independently at each occurrence a pharmaceutically acceptable anion;

including any stereoisomer thereof, or any solvate or hydrate thereof.

2. The compound of claim 1 wherein $R^1$, $R^2$, or both, are methyl.

3. The compound of claim 1 wherein $R^3$, $R^4$, or both, are hydrogen.

4. The compound of claim 1 wherein n1 and n2 are both 2.

5. The compound of claim 1 wherein m1 and m3 are each independently 2 or 3.

6. The compound of claim 1 wherein m2 and m4 are each independently 2 or 3.

7. The compound of claim 1 wherein $R^{11}$, $R^{12}$, $R^{13}$, and $R^{14}$ are all methoxy, or wherein any two of $R^{11}$, any two of $R^{12}$, any two of $R^{13}$, or any two of $R^{14}$, are methylenedioxy, or any combination thereof.

8. The compound of claim 1 wherein $R^1$ and $R^3$ are in a trans configuration.

9. The compound of claim 1 wherein $R^2$ and $R^4$ are in a trans configuration.

10. The compound of claim 1 wherein the carbon atom bearing $R^3$, the carbon atom bearing $R^4$, or both carbon atoms, are in the R absolute configuration.

11. The compound of claim 1 wherein the nitrogen atom bearing $R^1$, the nitrogen atom bearing $R^2$, or both nitrogen atoms, are in the S absolute configuration.

12. The compound of claim 1 wherein both X are chloride.

13. The compound of claim 1, wherein the compound is an R-trans, R-trans compound of formula (II)

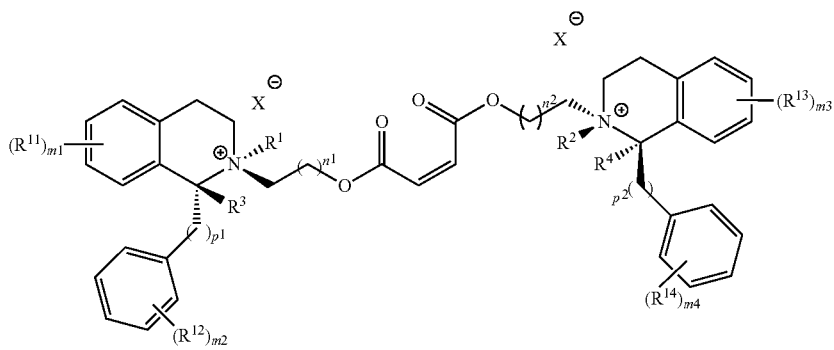

or any solvate or hydrate thereof.

14. The compound of claim 13, wherein the compound is an R-trans, R-trans compound of formula (IIA)

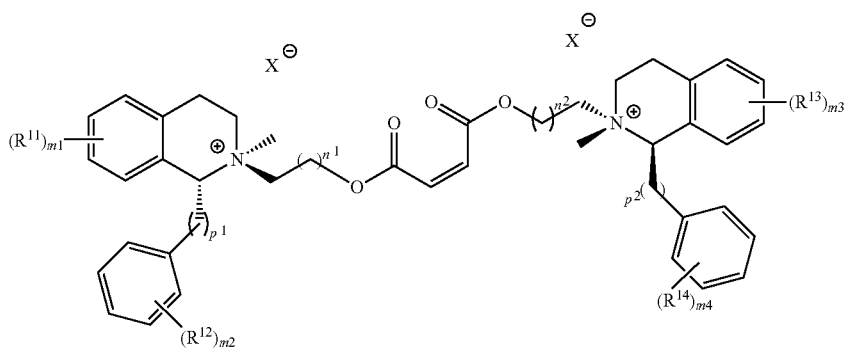

or any solvate or hydrate thereof.

15. The compound of claim 13, wherein the compound is an R-trans, R-trans compound of formula (IIB), wherein n1 and n2 are both equal to 2.

16. The compound of claim 14 wherein the compound is a maleate diester.

17. The compound of claim 14 wherein p1 and p2 are both 1.

18. The compound of claim 14 wherein one of p1 and p2 is 0 and one of p1 and p2 is 1.

19. The compound of claim 14 wherein p1 and p2 are both 0.

20. The compound of claim 1 wherein the compound is any of the following maleates:

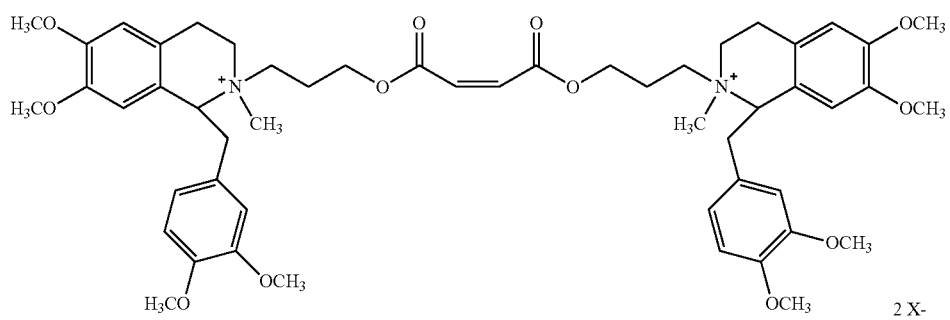

-continued
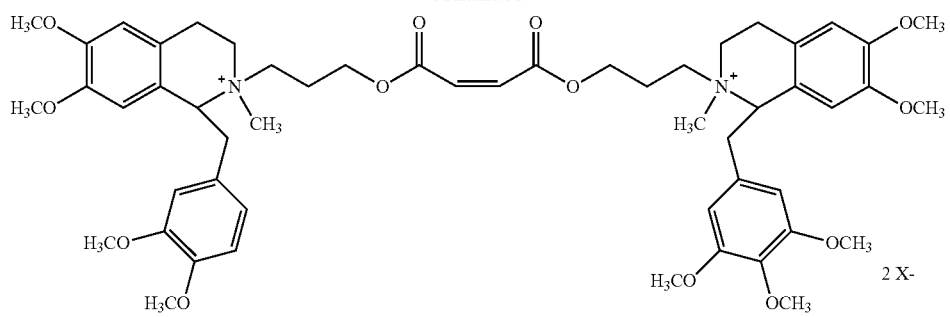
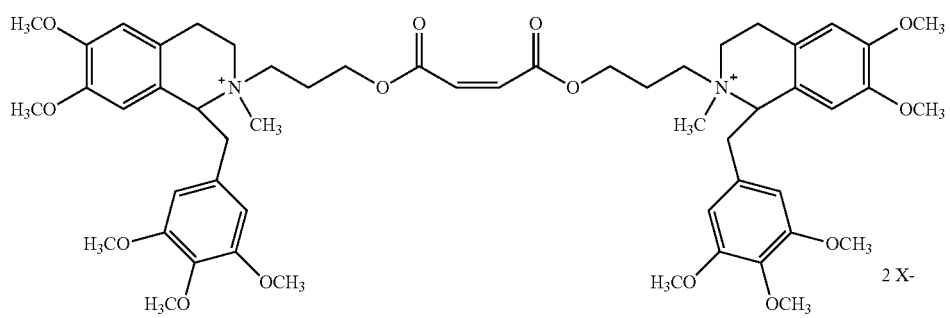
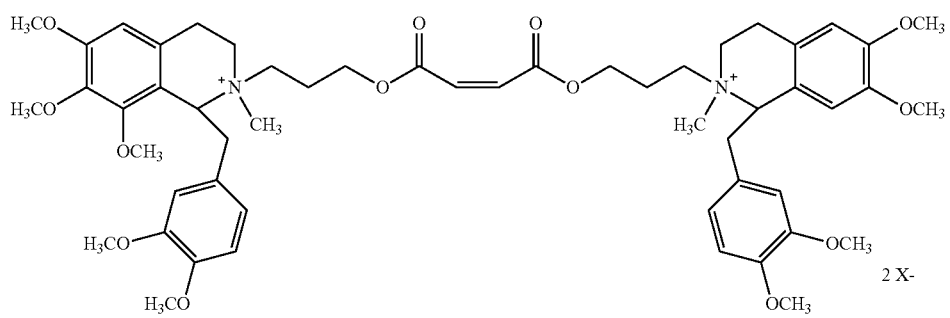
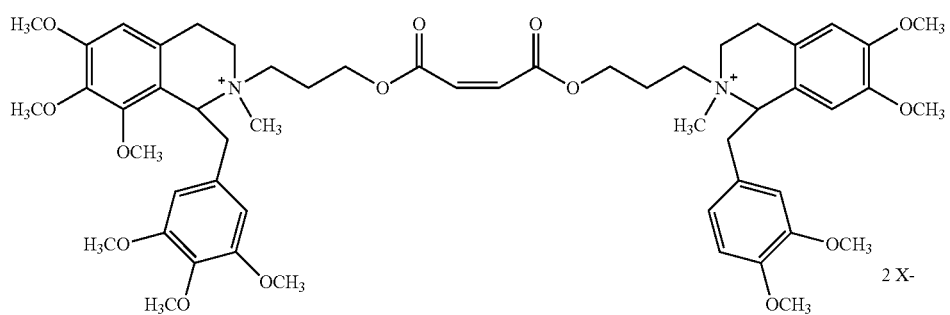
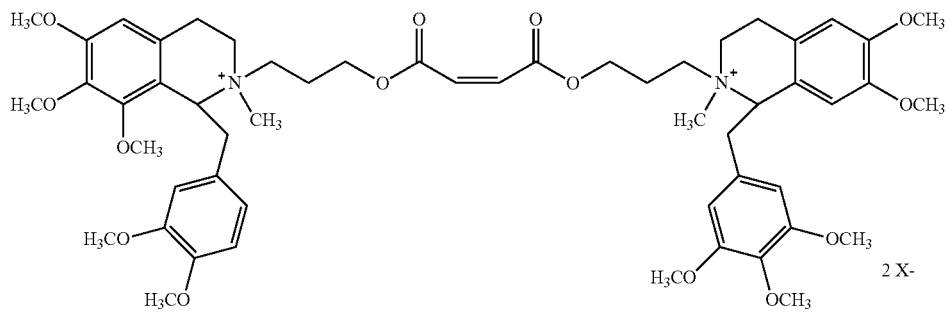

-continued
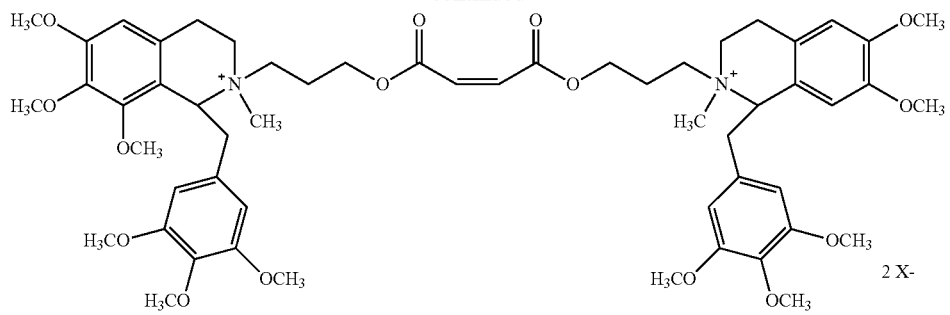
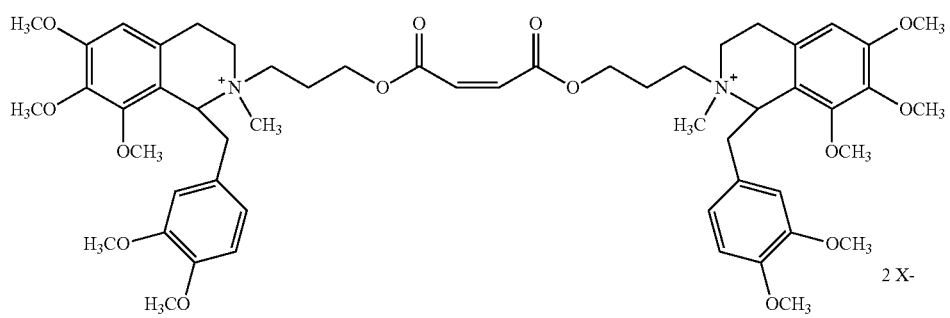
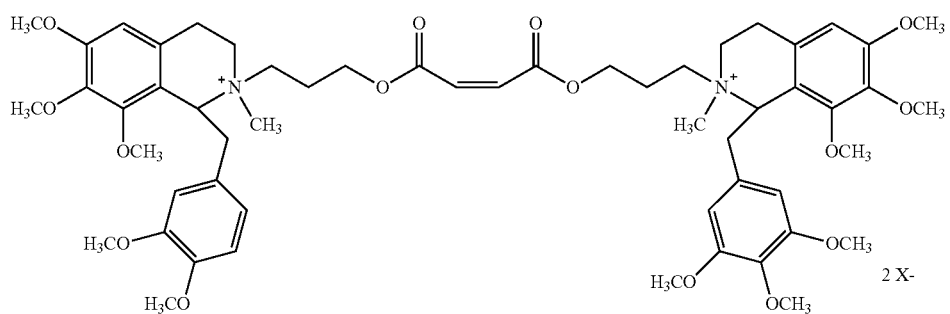
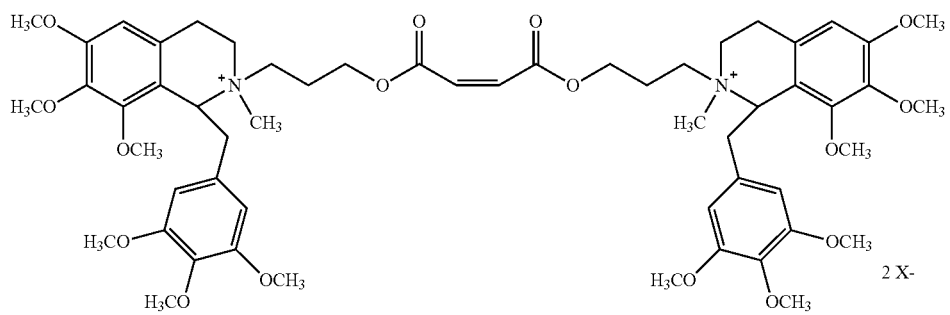
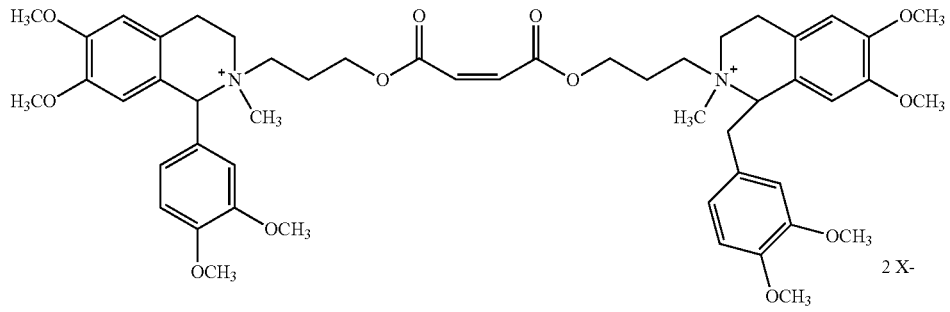

-continued
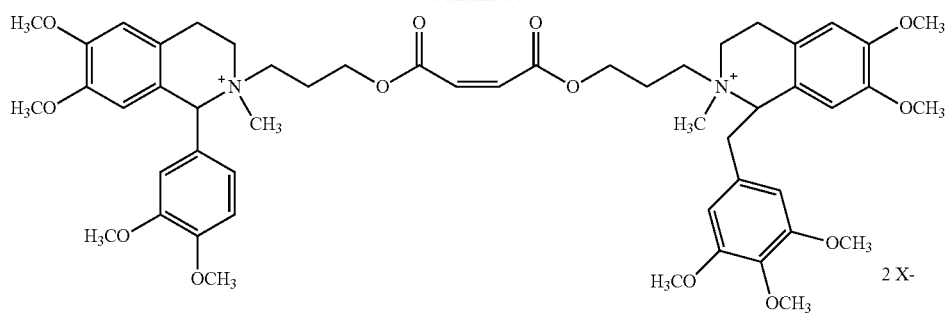
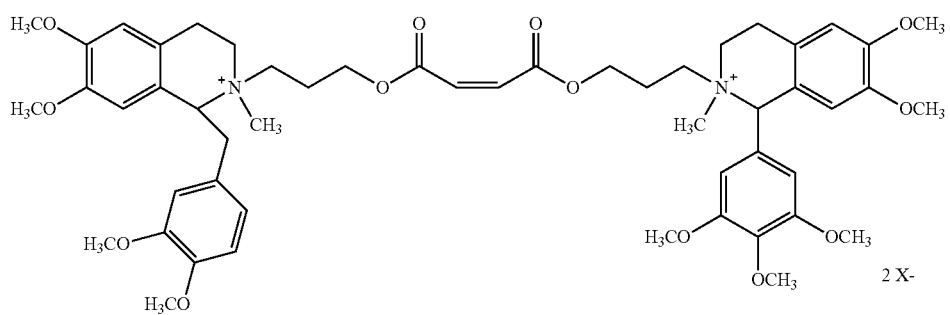
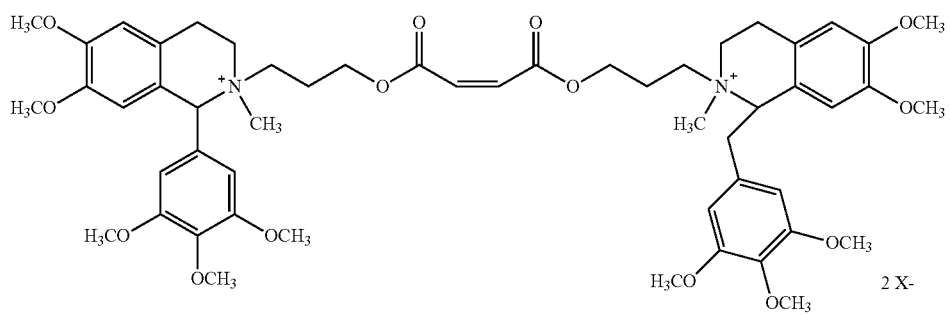
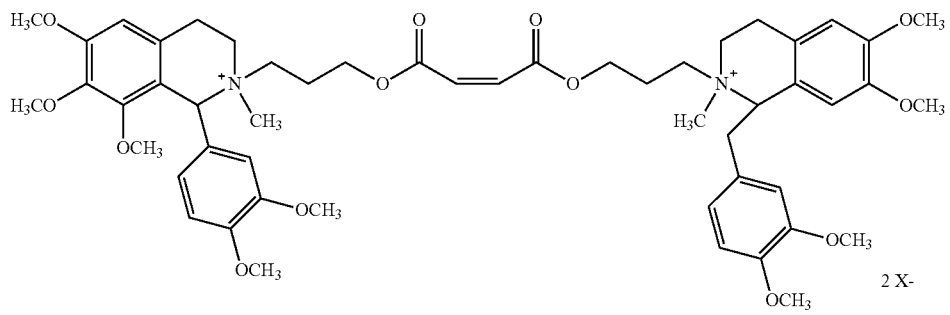
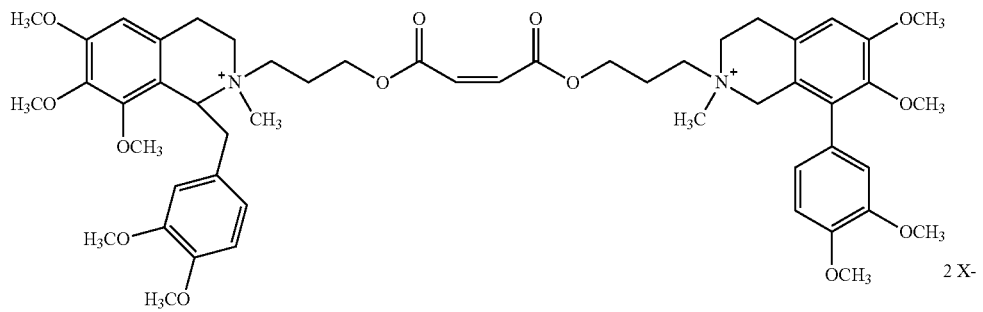

-continued
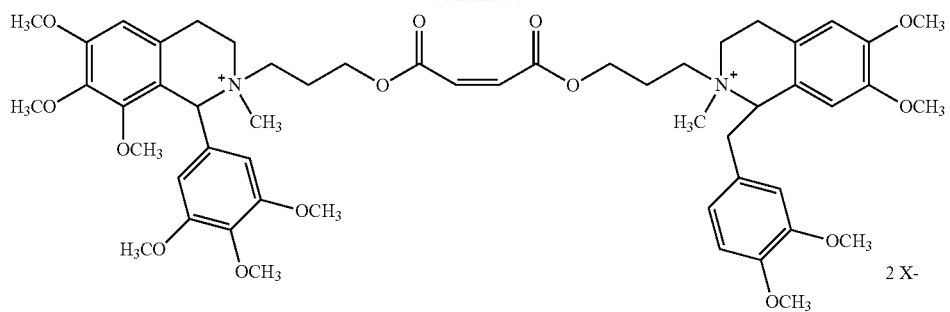
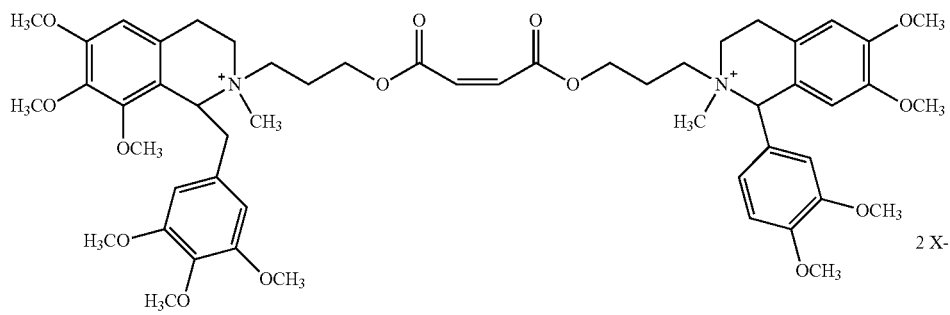
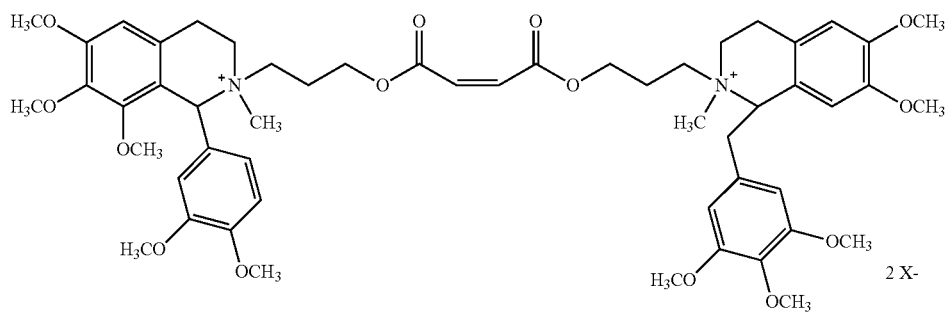
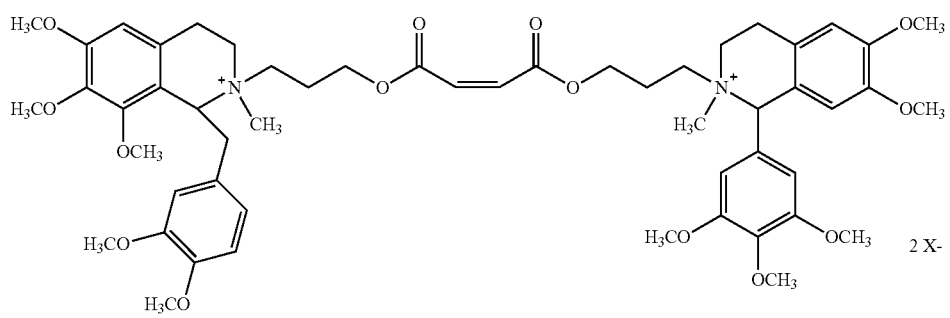
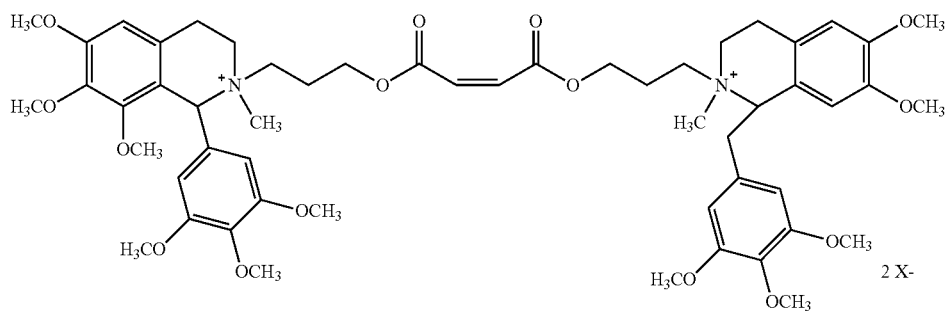

-continued
103
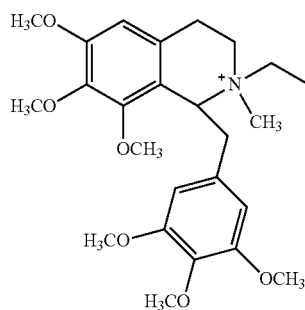
104
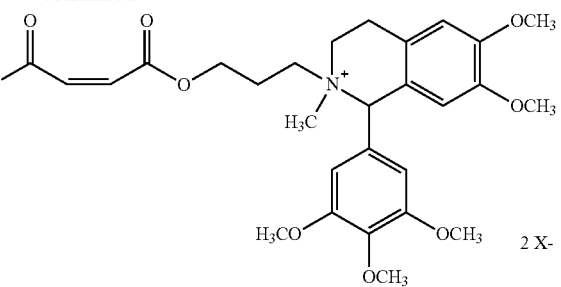
2 X⁻
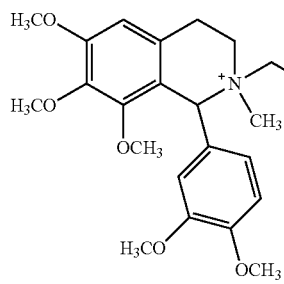
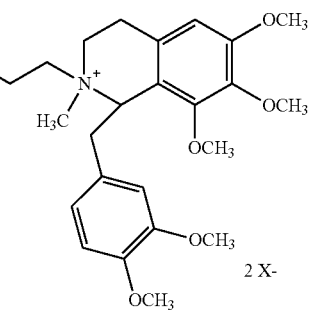
2 X⁻
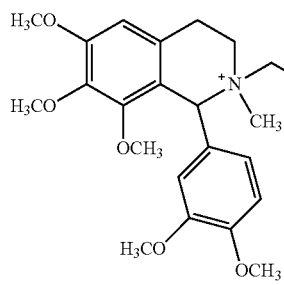
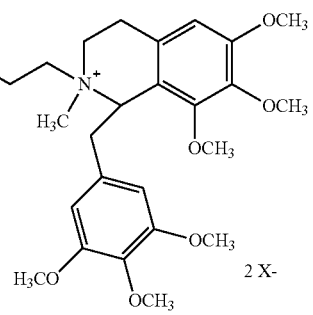
2 X⁻
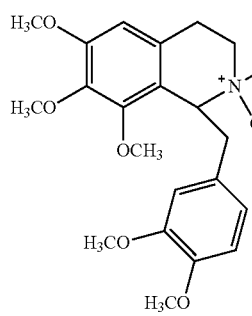
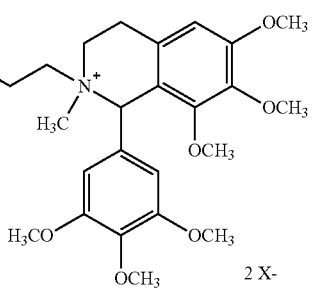
2 X⁻
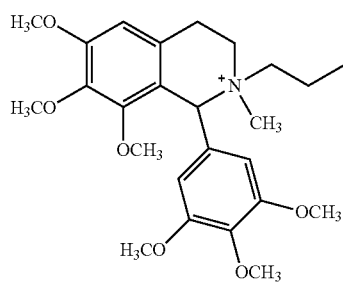
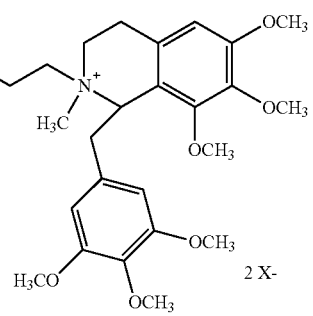
2 X⁻ including any stereoisomer thereof, or any solvate or hydrate thereof.

21. The compound of claim 1 wherein the maleate compound is any of the following:

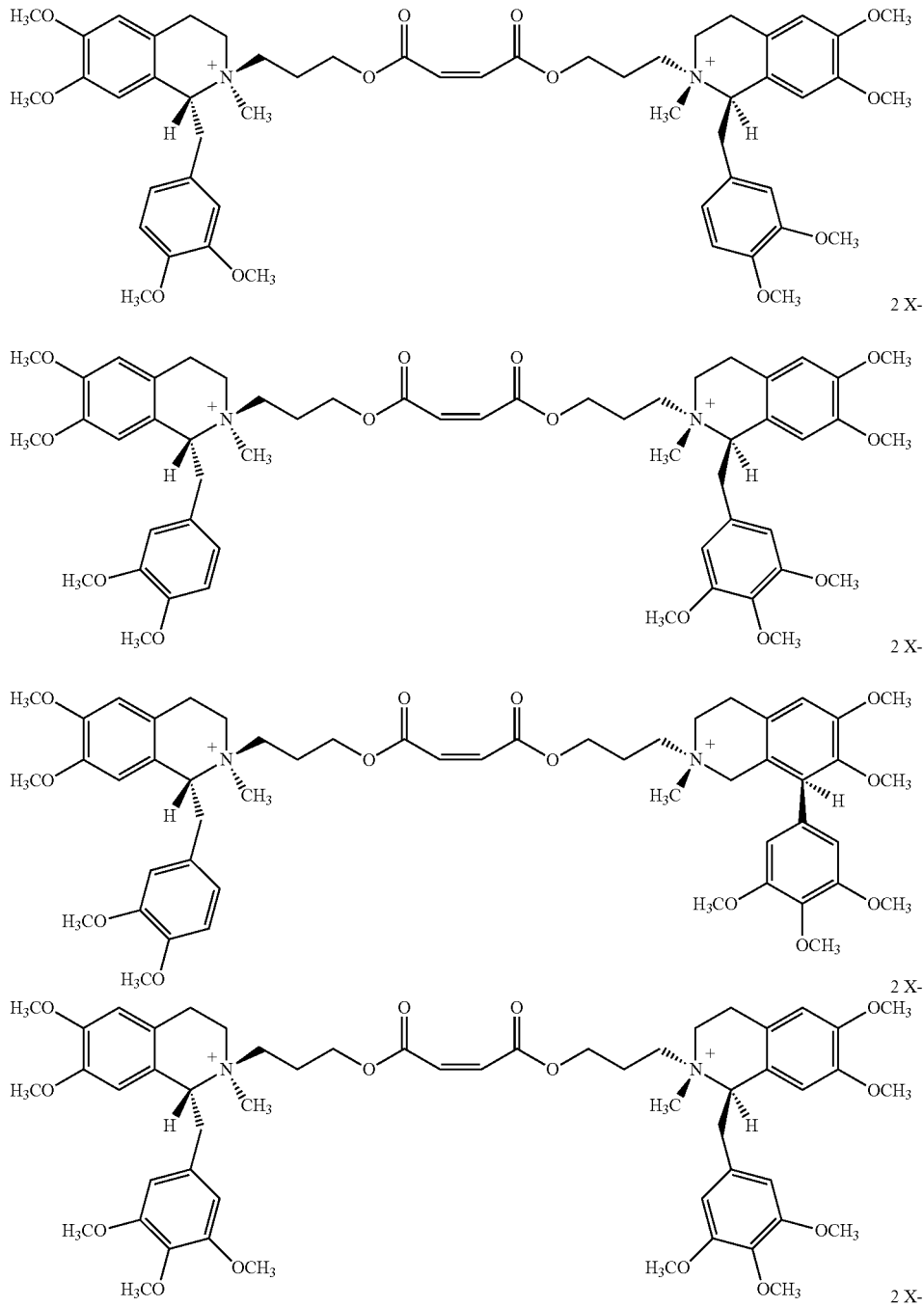

or any solvate or hydrate thereof.

22. A composition comprising a compound of claim 1 and a pharmaceutically acceptable excipient.

23. The composition of claim 22 adapted for parenteral administration to a patient.

24. A compound of claim 1 wherein the compound produces, upon administration of an effective amount of the compound to a patient, a neuromuscular blockade.

25. The compound of claim 24 wherein the effective amount is about 0.01-10 mg per kg patient bodyweight.

26. The compound of claim 25 wherein the effective amount is about 0.1-1 mg per kg patient bodyweight.

27. The compound of claim 24 wherein the neuromuscular blockage is reversible by administration to the patient of an effective amount of a thiol compound.

28. The compound of claim 27 wherein the thiol compound is L-cysteine or a pharmaceutically acceptable salt thereof, D-cysteine or a pharmaceutically acceptable salt thereof, or glutathione or a pharmaceutically acceptable salt thereof.

29. A method of inducing neuromuscular blockade in a patient, comprising administering an effective amount of a compound of claim 1 to the patient.

30. The method of claim 29 wherein the effective amount is about 0.01-10 mg per kg patient bodyweight.

31. The method of claim 29 wherein the effective amount is about 0.1-1 mg per kg patient bodyweight.

32. The method of claim 29 wherein inducing neuromuscular blockade is carried out as part of a regimen of anesthesia.

33. The method of claim 29 wherein the neuromuscular blockade is non-depolarizing.

34. The method of claim 29 wherein the neuromuscular blockade is achieved with little or no circulatory effect.

35. The method of claim 29 wherein the neuromuscular blockade in the patient is subsequently reversed by administration of a thiol compound.

36. The method of claim 35 wherein the thiol compound is L-cysteine or a pharmaceutically acceptable salt thereof, D-cysteine or a pharmaceutically acceptable salt thereof, or glutathione or a pharmaceutically acceptable salt thereof.

37. The method of claim 35 wherein the blockade is reversible within about 2-5 minutes after administration of the thiol compound to the patient following induction of the neuromuscular blockade.

38. The method of claim 35 wherein the thiol compound is administered to the patient immediately following a surgical procedure for which a compound of formula (I) had been previously administered to the patient.

39. The method of claim 35 wherein the thiol compound comprises cysteine or a salt thereof and the cysteine or salt thereof is administered at a dose of about 10 mg/kg to about 50 mg/kg on a free base basis.

40. The method of claim 39 wherein the cysteine or salt thereof is D-cysteine hydrochloride.

41. A dosage form of a compound of claim 1 comprising an injectable solution of the compound in a suitable biocompatible solvent.

42. The dosage form of claim 41 comprising about 1 mg/mL to about 10 mg/mL of the compound per dose.

43. The dosage form of claim 41 wherein the suitable biocompatible solvent comprises sterile, pyrogen-free water.

44. The dosage form of claim 41 wherein the suitable biocompatible solvent comprises isotonic NaCl.

45. The dosage form of claim 41 wherein the suitable biocompatible solvent comprises alcohol, a polyethylene glycol, DMSO, or any mixture thereof.

46. The dosage form of claim 41 wherein the pH of the solution is about 2.5 to about 3.5.

47. The dosage form of claim 41 adapted for frozen storage.

48. A kit comprising a compound of claim 1 in a first container and, optionally, a thiol compound suitable for reversing the neuromuscular blockade effect of the compound on a patient in a second container.

49. The kit of claim 48 wherein the first container comprises a dosage form of any of claims 41-46.

50. The kit of claim 48 wherein the second container comprises a solution of D-cysteine hydrochloride, L-cysteine hydrochloride, or both.

51. The kit of claim 49 wherein the solution within is of a pH of about 2-3 for storage.

52. The kit of claim 49 further comprising third container comprising a buffer to adjust the pH of the solution of the first container, the second container, or both, to about 5-6 prior to administration to the patient.

53. A method of synthesis of a maleate compound of claim 2, comprising contacting a compound of formula (III)

and maleic anhydride,
to provide a compound of formula (IIIA)

or any salt thereof,
then, contacting the compound of formula (IIIA) and an independently selected compound of formula (IIIB)

under conditions suitable to bring about ester formation, to provide the maleate compound of claim 1.

54. The method of claim 53 in which all of $R^{11}$, $R^{12}$, $R^{13}$ and $R^{14}$ are methoxy, m1 and m3 are each independently 2, 3, or 4, and m2 and m4 are each independently 2 or 3.

55. A method of synthesis of a compound of claim 1, comprising contacting a compound of formula (III)

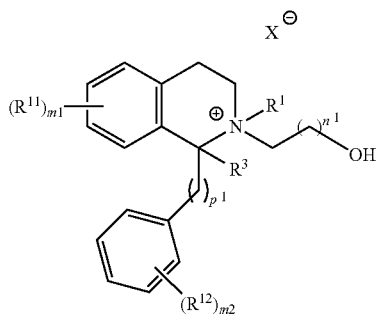
(III)

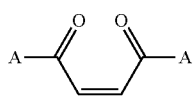
(IV)

and an activated diacid of formula (IV)

wherein each A is each independently a carboxyl activating group, under conditions suitable to bring about ester formation,
to provide the compound of formula (IA)

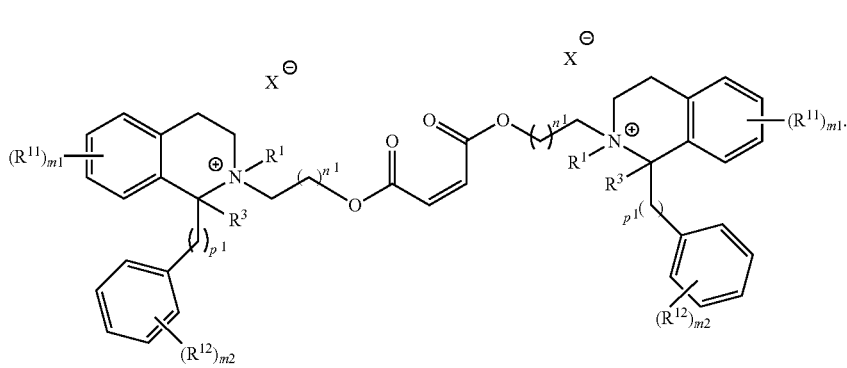
(IA)

56. The method of claim 55 in which $R^{11}$ and $R^{12}$ are methoxy, m1 is 2, 3, or 4, and m2 is 2 or 3.

57. A method of synthesis of a compound of claim 1, comprising contacting a mono-protected mono-activated diacid of formula (XXXI)

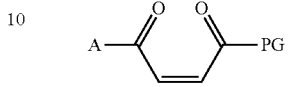
(XXXI)

wherein PG is a carboxy-protecting group and A is a carboxy-activating group, and an isoquinolylalkanol of formula (XXXII)

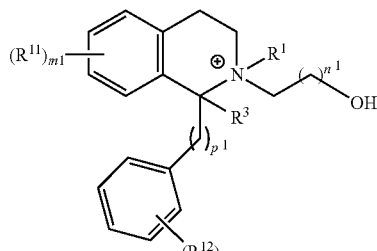
(XXXII)

under conditions suitable to bring about ester formation, to provide a compound of formula (XXXIII)

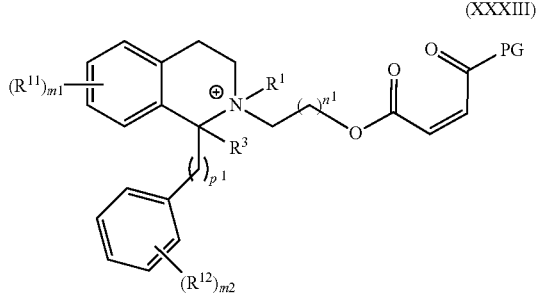

(XXXIII)

then, removing protecting group PG to provide a free carboxylic acid;

then, activating the free carboxylic acid to provide a compound of formula (XXXIV)

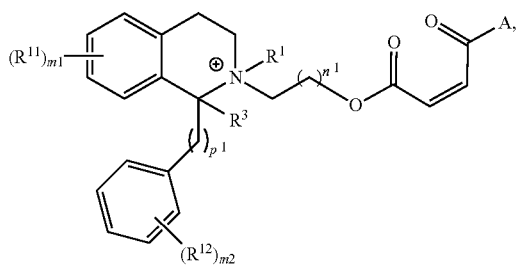

(XXXIV)

then, contacting the compound of formula (XXXIV), and a compound of formula (XXXV)

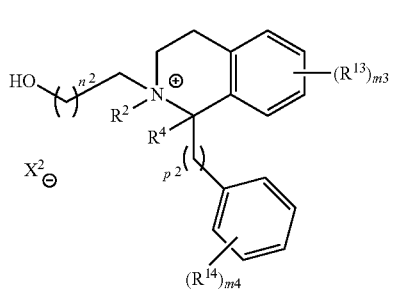

(XXXV)

under conditions suitable to bring about ester formation, to provide of formula (I)

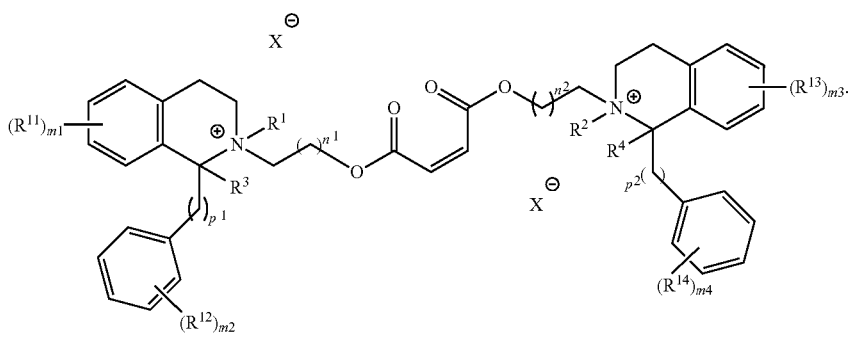

(I)

58. The method of claim 57 in which $R^{11}$ and $R^{12}$ are methoxy, m1 is 2, 3, or 4, and m2 is 2 or 3.

* * * * *

UNITED STATES PATENT AND TRADEMARK OFFICE
CERTIFICATE OF CORRECTION

| | |
|---|---|
| PATENT NO. | : 8,592,451 B2 |
| APPLICATION NO. | : 13/257214 |
| DATED | : November 26, 2013 |
| INVENTOR(S) | : John J. Savarese |

Page 1 of 1

It is certified that error appears in the above-identified patent and that said Letters Patent is hereby corrected as shown below:

In the Claims

In column 92, line 27, in Claim 2, delete "$R^{1,R2}$," and insert --$R^1$, $R^2$,--, therefor In column 112, line 33 (approx.), in Claim 57, after "provide", insert --a compound--, therefor Signed and Sealed this
Eleventh Day of March, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,592,451 B2 | Page 1 of 1 |
| APPLICATION NO. | : 13/257214 | |
| DATED | : November 26, 2013 | |
| INVENTOR(S) | : John J. Savarese | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 101 days.

Signed and Sealed this
Eleventh Day of August, 2015

Michelle K. Lee
*Director of the United States Patent and Trademark Office*